(12) United States Patent
Sheppeck et al.

(10) Patent No.: US 7,361,654 B2
(45) Date of Patent: Apr. 22, 2008

(54) SUBSTITUTED HETEROARYL AMIDE MODULATORS OF GLUCOCORTICOID RECEPTOR, AP-1, AND/OR NF-κB ACTIVITY AND USE THEREOF

(75) Inventors: James Sheppeck, Newtown, PA (US); T. G. Murali Dhar, Newtown, PA (US); Lidia Doweyko, Long Valley, NJ (US); John Gilmore, Yardley, PA (US); David Weinstein, East Windsor, NJ (US); Hai-Yun Xiao, Belle Mead, NJ (US); Bingwei V. Yang, Belle Mead, NJ (US); Arthur M. Doweyko, Long Valley, NJ (US)

(73) Assignee: Bristol-Myers Squibb Co., Princeton, NJ (US)

( * ) Notice: Subject to any disclaimer, the term of this patent is extended or adjusted under 35 U.S.C. 154(b) by 0 days.

(21) Appl. No.: 11/330,553

(22) Filed: Jan. 12, 2006

(65) Prior Publication Data

US 2006/0154973 A1    Jul. 13, 2006

Related U.S. Application Data

(60) Provisional application No. 60/643,509, filed on Jan. 13, 2005.

(51) Int. Cl.
| | |
|---|---|
| *A61K 31/5377* | (2006.01) |
| *A61K 31/506* | (2006.01) |
| *A61K 31/501* | (2006.01) |
| *A61K 31/497* | (2006.01) |
| *A61K 31/496* | (2006.01) |
| *A61K 31/4439* | (2006.01) |
| *A61K 31/427* | (2006.01) |
| *A61K 31/426* | (2006.01) |
| *A61K 31/4196* | (2006.01) |
| *A61K 31/4168* | (2006.01) |

(52) U.S. Cl. .............. 514/235.5; 514/252.13; 514/252.05; 514/253.1; 514/254.02; 514/256; 514/274; 514/340; 514/342; 514/371; 514/383; 514/398; 514/392; 544/111; 544/238; 544/298; 544/359; 546/268.1; 546/268.4; 548/190; 548/314.7; 548/332.5; 548/265.4; 548/233; 548/304.4

(58) Field of Classification Search ............. 548/190, 548/314.7, 332.5, 265.4, 233, 304.4; 546/268.1, 546/268.4; 544/111, 238, 298, 359; 514/371, 514/377, 396, 340, 235.5, 252.13, 274
See application file for complete search history.

(56) References Cited

U.S. PATENT DOCUMENTS

| | | | |
|---|---|---|---|
| 3,317,387 A | 5/1967 | Prichard | |
| 3,422,104 A | 1/1969 | Schröter et al. | |
| 3,517,073 A | 6/1970 | Fields | |
| 4,786,646 A | 11/1988 | Guthrie et al. | |
| 5,055,468 A | 10/1991 | Gray et al. | |
| 5,202,486 A | 4/1993 | Barrish et al. | |
| 5,332,820 A | 7/1994 | Duncia | |
| 5,409,932 A | 4/1995 | Schwenner et al. | |
| 5,411,960 A | 5/1995 | Schwenner et al. | |
| 5,455,248 A | 10/1995 | DeHaven-Hudkins et al. | |
| 5,514,683 A | 5/1996 | Kalindjian et al. | |
| 5,569,655 A | 10/1996 | Dority, Jr. et al. | |
| 5,616,780 A | 4/1997 | Pitteloud et al. | |

(Continued)

FOREIGN PATENT DOCUMENTS

CS          198 678          11/1982

(Continued)

OTHER PUBLICATIONS

Alibert, S. et al., "Synthesis and Effects on Chloroquine Susceptibility in *Plasmodium falciparum* of a Series of New Dihydroanthracene Derivatives", Journal of Medicinal Chemistry, vol. 45, No. 15, pp. 3195-3209 (2002).

(Continued)

*Primary Examiner*—Rebecca Anderson
*Assistant Examiner*—Jason M Nolan
(74) *Attorney, Agent, or Firm*—Laurelee A. Duncan

(57) ABSTRACT

The present invention relates to new class of non-steroidal compounds which are useful in treating diseases associated with modulation of the glucocorticoid receptor, AP-1, and/or NF-κB activity including obesity, diabetes, inflammatory- and immune-associated diseases, and have the structure

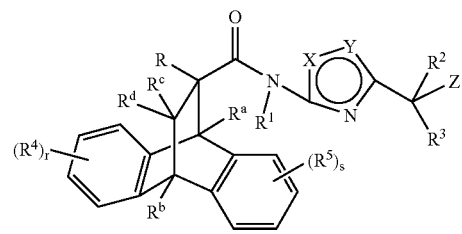

including all stereoisomers thereof, tautomers thereof, or a prodrug thereof, or a pharmaceutically acceptable salt thereof, wherein X is selected from N, O, and S; Y is N or $CR^6$; Z is a ring; and where R, $R^a$, $R^b$, $R^c$, $R^d$, $R^1$, $R^2$, $R^3$, $R^4$, and $R^5$ are as defined herein. Also provided are pharmaceutical compositions and methods of treating obesity, diabetes and inflammatory or immune associated diseases comprising such compounds.

14 Claims, No Drawings

U.S. PATENT DOCUMENTS

| | | |
|---|---|---|
| 6,214,915 B1 | 4/2001 | Avakian et al. |
| 6,262,059 B1 | 7/2001 | Pamukcu et al. |
| 6,291,679 B1 | 9/2001 | Mailliet et al. |
| 6,995,181 B2 | 2/2006 | Vaccaro et al. |
| 2005/0182110 A1 | 8/2005 | Yang |

FOREIGN PATENT DOCUMENTS

| | | |
|---|---|---|
| DE | 197 42 014 | 3/1999 |
| EP | 0 405 436 | 11/1995 |
| WO | WO 93/16982 | 9/1993 |
| WO | WO 94/00421 | 1/1994 |
| WO | WO 95/05359 | 2/1995 |
| WO | WO 95/15947 | 6/1995 |
| WO | WO 99/15493 | 4/1999 |
| WO | WO 02/051851 | 7/2002 |
| WO | WO 03/062241 | 7/2003 |
| WO | WO 03/101932 | 12/2003 |
| WO | WO 03/104195 | 12/2003 |
| WO | WO 04/000869 | 12/2003 |
| WO | WO 2004/005229 | 1/2004 |
| WO | WO 2004/009017 | 1/2004 |
| WO | WO 2005/070207 | 8/2005 |
| WO | WO 2005/072729 | 8/2005 |
| WO | WO 2005/072732 | 8/2005 |
| WO | WO 2005/073221 | 8/2005 |
| ZA | 681802 | 3/1968 |

OTHER PUBLICATIONS

Baldwin, Jr., A.S., "The transcription factor NF-κB and human disease", The Journal of Clinical Investigation, vol. 107, No. 1, pp. 3-6 (2001).

Bradsher, C.K. et al., "Acridizinium Ion Chemistry. II. The Diels-Alder Reaction", Journal of the American Chemical Society, vol. 80, pp. 933-934 (1958).

Bradsher, C.K. et al., "Addition of Dienophiles to the Acridizinium Ion. III. Evidence for a Two-Step Reaction", The Journal of Organic Chemistry, vol. 34, No. 6, pp. 1700-1702 (1969).

Bradsher, C.K. et al., "Cationic Polar Cycloaddition of Cyclopropenes", J. Org. Chem., vol. 44, No. 8, pp. 1199-1202 (1979).

Bradsher, C.K. et al., "Possible Role of Charge-Transfer Complexes in Cationic Polar Cycloaddition", J. Org. Chem., vol. 43, No. 5, pp. 822-827 (1978).

Bradsher, C.K. et al., "Stereoselectivity Due to Electrostatic Repulsion in the Polar Cycloaddition of the Acridizinium Ion", J. Het. Chem., vol. 10, pp. 1031-1033 (1973).

Bradsher, C.K. et al., "Steric Effects in Some Cycloaddition Reactions", Journal of the American Chemical Society, vol. 99, No. 8, pp. 2588-2591 (1977).

Bradsher, C.K. et al., "The Nature of the Addition of Dienophiles to the Acridizinium Ion", The Journal of Organic Chemistry, vol. 33, No. 2, pp. 519-523 (1968).

Burke, J.R., "Targeting IκB kinase for the treatment of inflammatory and other disorders", Current Opinion in Drug Discovery & Development, vol. 6, No. 5, pp. 720-728 (2003).

Burnham, W.S. et al., "6,11-Dihydroacridizinium Derivatives Having a 6,11-Etheno Bridge", J. Org. Chem., vol. 37, No. 3, pp. 355-358 (1972).

Butler, D.N. et al., "Chemistry of Proximal π-Bond Systems. Part I. Synthesis of Vicinal Exocyclic Dimethylene Hydrocarbons", Canadian Journal of Chemistry, vol. 50, pp. 795-802 (1972).

Caldenhoven, E. et al., "Negative Cross-Talk between ReIA and the Glucocorticoid Receptor: A Possible Mechanism for the Antiinflammatory Action of Glucocorticoids", Molecular Endocrinology, vol. 9, No. 4, pp. 401-412 (1995).

Chakravarti, D. et al., "Role of CBP/P300 in nuclear receptor signalling", Nature, vol. 383, pp. 99-103, (1996).

Compounds (by Registry Number) with no references in the Chemical Abstracts file: 500280-08-0, 496959-82-1, 332907-97-8, 331751-07-6, 331427-65-7, 312317-98-9, 312315-55-2, 311331-77-8.

Diamond, M.I. et al., "Transcription Factor Interactions: Selectors of Positive or Negative Regulation from a Single DNA Element", Science, vol. 249, pp. 1266-1272 (1990).

El-Zanfally, S. et al., "Reactions of Aminopyridines with some Inner Anhydrides", Egypt J. Pharm. Sci., vol. 17, No. 3, pp. 53-62 (1976).

Fields, D.L., "A Novel Synthesis of 2-Naphthols, Phenanthrols, Anthracenes, and Other Polycyclic Aromatic Products", J. Org. Chem., vol. 36, No. 20, pp. 3002-3005 (1971).

Fields, D.L. et al., "Azonia Polycyclic Quinones, o-Diazo-Oxides and Related Products", J. Het. Chem., vol. 7, pp. 91-97 (1970).

Fields, D.L. et al., "Cleavage Reactions of Bicyclic Ketones Derived from Azoniaanthracene-Ketene Acetal Adducts", J. Org. Chem., vol. 36, No. 6, pp. 1870-1875 (1970).

Fields, D.L. et al., "Diels-Alder Reactions Involving Azonia Polycyclic Aromatic Compounds and Nucleophilic Dienophiles", J. Org. Chem., vol. 33, No. 1, pp. 390-395 (1968).

Fields, D.L. et al., "Overcrowded Molecules. I. Substituted 8-*tert*-Butyl-1-(2-pyridyl)naphthalenes, Including a Thermodynamically Stable Ketonic Tautomer", J. Org. Chem., vol. 36, No. 20, pp. 2986-2990 (1971).

Fields, D.L. et al., "Overcrowded Molecules. II. 4,5-Bis(2-pyridyl)phenanthrene-3,6-diols", J. Org. Chem., vol. 36, No. 20, pp. 2991-2995 (1971).

Fields, D.L. et al., "Overcrowded Molecules. III. 13,14-Bis(2-pyridyl)pentaphene and Related Compounds", J. Org. Chem., vol. 36, No. 20, pp. 2995-3001 (1971).

Firestein, G.S. et al., "Signal Transduction and Transcription Factors in Rheumatic Disease", Arthritis & Rheumatism, vol. 42, No. 4, pp. 609-621 (1999).

Hart, H. et al., "1,4,5,8,9-pentamethylanthracene, Synthesis and Protonation", Tetrahedron Letters, vol. 16, No. 52, pp. 4639-4642 (1975).

Jackson, R.W. et al., "Benzobicyclooctanes as Novel Inhibitors of TNF-α Signaling", Bioorganic & Medicinal Chemistry Letters, vol. 12, pp. 1093-1097 (2002).

Jonat, C. et al., "Antitumor Promotion and Antiinflammation: Down-Modulation of AP-1 (Fos/Jun) Activity by Glucocorticoid Hormone", Cell, vol. 62, pp. 1189-1204 (1990).

Kamei, Y. et al., "A CBP Integrator Complex Mediates Transcriptional Activation and AP-1 Inhibition by Nuclear Receptors", Cell, vol. 85, pp. 403-414 (1996).

Kotha, S. et al., "Synthesis of highly constrained unusual α-amino acid derivative by the Diels-Alder approach", Indian Journal of Chemistry, vol. 41B, pp. 2330-2332 (2002).

Manning, A.M. et al., "Targeting JNK for Therapeutic Benefit: From Junk to Gold", Nature Reviews Drug Discovery, vol. 2, pp. 554-565 (2003).

Miesfeld, R. et al., "Characterization of a steroid hormone receptor gene and mRNA in wild-type and mutant cells", Nature, vol. 312, 779-781 (1984).

Parham, M.E. et al., "The Cycloaddition of the Acridizinium Ion with Norbornene Derivatives", J. Org. Chem., vol. 37, No. 3, pp. 358-362 (1972).

Peltz, G., "Transcription factors in immune-mediated disease", Current Opinion in Biotechnology, vol. 8, pp. 467-473 (1997).

Pradines, B. et al., "In Vitro Increase in Chloroquine Accumulation Induced by Dihydroethano- and Ethenoanthracene Derivatives in *Plasmodium falciparum*-Parasitized Erythrocytes", Antimicrobial Agents and Chemotherapy, vol. 46, No. 7, pp. 2061-2068 (2002).

Prostakov, N.S. et al., "Hydrogenation and halogenation of 6-phenyl-5-azabenzo[f]fluoranthene and reduction of its adducts with acrylonitrile", Khimiya Geterotsiklicheskikh Soedinenii, vol. 2, pp. 233-235 (1982), abstract only.

Reichardt, H.M. et al., "DNA Binding of the Glucocorticoid Receptor Is Not Essential for Survival", Cell, vol. 93, pp. 531-541 (1998).

Reichardt, H.M. et al., "Repression of inflammatory responses in the absence of DNA binding by the glucocorticoid receptor", The EMBO Journal, vol. 20, No. 24, pp. 7168-7173 (2001).

Weinberger, C. et al., "Domain structure of human glucocorticoid receptor and its relationship to the v-*erb-A* oncogene product", Nature, vol. 318, pp. 670-672 (1985).

Weinberger, C. et al., "Identification of Human Glucocorticoid Receptor Complementary DNA Clones by Epitope Selection", Science, vol. 228, pp. 740-742 (1985).

Westerman, I.J. et al., "Rates of Addition of Styrene to 9-Substituted Acridizinium Ions", J. Org. Chem., vol. 36, No. 7, pp. 969-970 (1971).

Westerman, I.J. et al., "Regiochemistry of Polar Cycloaddition. Validity of the Electrophilic Addition Model", J. Org. Chem., vol. 43, No. 15, pp. 3002-3006 (1978).

Westerman, I.J. et al., "Stereochemistry of Cationic Polar Cycloaddition", J. Org. Chem., vol. 44, No. 5, pp. 727-733 (1979).

Yang-Yen, H.-F. et al., "Transcriptional Interference between c-Jun and the Glucocorticoid Receptor: Mutual Inhibition of DNA Binding Due to Direct Protein-Protein Interaction", Cell, vol. 62, pp. 1205-1215 (1990).

SUBSTITUTED HETEROARYL AMIDE MODULATORS OF GLUCOCORTICOID RECEPTOR, AP-1, AND/OR NF-κB ACTIVITY AND USE THEREOF

This application claims the benefit of priority from U.S. Provisional Application Ser. No. 60/643,509, filed Jan. 13, 2005, the entirety of which is incorporated herein by reference.

FIELD OF THE INVENTION

The present invention relates to new class of non-steroidal compounds which are particularly effective modulators of the glucocorticoid receptor, AP-1, and/or NF-κB activity and thus are useful in treating diseases such as obesity, diabetes and inflammatory or immune associated diseases, and to a method for using such compounds to treat these and related diseases.

BACKGROUND OF THE INVENTION

The transcription factors NF-κB and AP-1 are involved in regulating the expression of a number of genes involved in mediating inflammatory and immune responses. NF-κB regulates the transcription of genes including TNF-α, IL-1, IL-2, IL-6, adhesion molecules (such as E-selectin) and chemokines (such as Rantes), among others. AP-1 regulates the production of the cytokines TNF-α, IL-1, IL-2, as well as, matrix metalloproteases. Drug therapies targeting TNF-α, a gene whose expression is regulated by both NF-κB and AP-1, have been shown to be highly efficacious in several inflammatory human diseases including rheumatoid arthritis and Crohn's disease. Accordingly, NF-κB and AP-1 play key roles in the initiation and perpetuation of inflammatory and immunological disorders. See Baldwin, A S, *Journal of Clin. Investigation,* 107, 3 (2001); Firestein, G. S., and Manning, A. M., *Arthritis and Rheumatism,* 42, 609 (1999); and Peltz, G., *Curr. Opin, in Biotech.* 8, 467 (1997).

There are many signaling molecules (kinases and phosphatases) upstream of AP-1 and NF-κB which are potential therapeutic drug targets. The kinase JNK plays an essential role in regulating the phosphorylation and subsequent activation of c-jun, one of the subunits which constitute the AP-1 complex (fos/c-jun). Compounds which inhibit JNK have been shown to be efficacious in animal models of inflammatory disease. See Manning A M and Davis R J, *Nature Rev. Drug Disc.,* V. 2, 554 (2003). A kinase critical to the activation of NF-κB is the IκB kinase (IKK). This kinase plays a key role in the phosphorylation of IκB. Once IκB is phosphorylated it undergoes degradation leading to the release of NF-κB which can translocate into the nucleus and activate the transcription of the genes described above. An inhibitor of IKK, BMS-345541, has been shown to be efficacious in animal models of inflammatory disease. See Burke J R., *Curr Opin Drug Discov Devel.,* September; 6(5), 720-8, (2003).

In addition to inhibiting signaling cascades involved in the activation of NF-κB and AP-1, the glucocorticoid receptor has been shown to inhibit the activity of NF-κB and AP-1 via direct physical interactions. The glucocorticoid receptor (GR) is a member of the nuclear hormone receptor family of transcription factors, and a member of the steroid hormone family of transcription factors. Affinity labeling of the glucocorticoid receptor protein allowed the production of antibodies against the receptor which facilitated cloning the glucocorticoid receptors. For results in humans see Weinberger, et al., *Science* 228, 640-742, (1985); Weinberger, et al., *Nature,* 318, 670-672 (1986) and for results in rats see Miesfeld, R., *Nature,* 312, 779-781, (1985).

Glucocorticoids which interact with GR have been used for over 50 years to treat inflammatory diseases. It has been clearly shown that glucocorticoids exert their anti-inflammatory activity via the inhibition by GR of the transcription factors NF-κB and AP-1. This inhibition is termed transrepression. It has been shown that the primary mechanism for inhibition of these transcription factors by GR is via a direct physical interaction. This interaction alters the transcription factor complex and inhibits the ability of NF-κB and AP-1 to stimulate transcription. See Jonat, C., et al., *Cell,* 62, 1189 (1990); Yang-Yen, H. F., et al,. *Cell,* 62, 1205 (1990); Diamond, M. I. et al., *Science* 249, 1266 (1990); and Caldenhoven, E. et al., *Mol. Endocrinol.,* 9, 401 (1995). Other mechanisms such as sequestration of co-activators by GR have also been proposed. See Kamer Y, et al., *Cell,* 85, 403 (1996); and Chakravarti, D. et al., *Nature,* 383, 99 (1996).

In addition to causing transrepression, the interaction of a glucocorticoid with GR can cause GR to induce transcription of certain genes. This induction of transcription is termed transactivation. Transactivation requires dimerization of GR and binding to a glucocorticoid response element (GRE).

Recent studies using a transgenic GR dimerization defective mouse which cannot bind DNA have shown that the transactivation (DNA binding) activities of GR could be separated from the transrepressive (non-DNA binding) effect of GR. These studies also indicate that many of the side effects of glucocorticoid therapy are due to the ability of GR to induce transcription of various genes involved in metabolism, whereas, transrepression, which does not require DNA binding leads to suppression of inflammation. See Tuckermann, J. et al., *Cell,* 93, 531 (1998) and Reichardt, H M, *EMBO J.,* 20, 7168 (2001).

PCT application WO 2004/009017 published Jan. 29, 2004, assigned to Applicant and incorporated herein in its entirety, describes substituted bicyclooctanes useful in treating diseases such as obesity, diabetes and inflammatory or immune associated diseases.

Compounds that modulate AP-1 and/or NF-κB activity would be useful as such compounds would be useful in the treatment of inflammatory and immune diseases and disorders such as osteoarthritis, rheumatoid arthritis, multiple sclerosis, asthma, inflammatory bowel disease, transplant rejection and graft vs. host disease.

Also, with respect to the glucocorticoid receptor pathway, it is known that glucocorticoids are potent anti-inflammatory agents, however their systemic use is limited by side effects. Compounds that retain the anti-inflammatory efficacy of glucocorticoids while minimizing the side effects such as diabetes, osteoporosis and glaucoma would be of great benefit to a very large number of patients with inflammatory diseases.

Additionally concerning GR, the art is in need of compounds that antagonize transactivation. Such compounds may be useful in treating metabolic diseases associated with increased levels of glucocorticoid, such as diabetes, osteoporosis and glaucoma.

Additionally concerning GR, the art is in need of compounds that cause transactivation. Such compounds may be useful in treating metabolic diseases associated with a deficiency in glucocorticoid. Such diseases include Addison's disease.

Also, there is a need for new compounds with improved activity compared with known modulators of GR, AP-1, and/or NF-κB activity. It is also desirable and preferable to find compounds with advantageous and improved characteristics in one or more categories, which may be, but are not limited to, the following: (a) pharmaceutical properties; (b) dosage requirements; (c) factors which decrease blood concentration peak-to-trough characteristics; (d) factors that increase the concentration of active drug at the receptor; (e) factors that decrease the liability for clinical drug-drug interactions; (f) factors that decrease the potential for adverse side-effects; (g) factors that improve manufacturing costs or feasibility and (h) factors leading to desirable physical characteristics, such as a desirable balance of hydrophilic and lipophilic properties.

DESCRIPTION OF THE INVENTION

In accordance with the present invention, compounds are provided having the structure of formula (I):

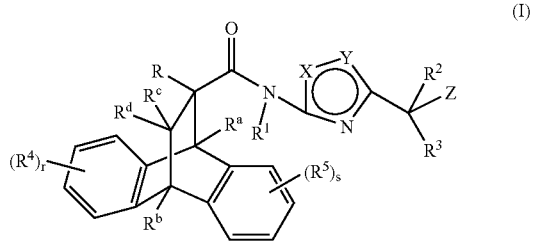

or a stereoisomer thereof, or a tautomer thereof, or a pharmaceutically acceptable salt thereof, wherein:

X is selected from N, NH, O, and S;

Y is N, NH, or $CR^6$;

R is hydrogen, cyano, hydroxy, alkyl, alkenyl, alkynyl, alkoxy, aryl, arylalkyl, aryloxy, heteroaryl, cycloheteroalkyl, heteroarylalkyl, cycloheteroalkylalkyl, cycloalkyl, cycloalkylalkyl, cyanoalkyl, aminoalkyl, hydroxyalkyl, aryloxyalkyl, or hydroxyaryl;

Z is a cycloalkyl, cycloalkenyl, heterocycloalkyl, aryl, or heteroaryl ring;

$R^1$ is hydrogen or $C_{1-4}$alkyl;

$R^2$ and $R^3$ are independently at each occurrence hydrogen, halogen, hydroxy, alkyl, alkenyl, alkynyl, alkoxy, cyano, nitro, $NR^eR^f$, or CHO, provided that if Y is $CR^6$ and X is S, then $R^2$ and $R^3$ are not both methyl;

or $R^2$ and $R^3$ combine to form =O or a double bond, wherein the double bond is substituted by hydrogen, aryl, alkyl, alkenyl, alkynyl, alkoxy, amino, substituted amino, alkoxyalkyl, alkylaminoalkyl, dialkylaminoalkyl, heteroaryl, cycloheteroalkyl, heteroarylalkyl, cycloheteroalkylalkyl, cycloalkyl, or cycloalkylalkyl;

$R^4$ and $R^5$ are independently at each occurence hydrogen, alkyl, aryl, cycloalkyl, heteroaryl, or cycloheteroalkyl;

$R^6$ is hydrogen, halogen, hydroxy, alkyl, alkenyl, alkynyl, alkoxy, aryl, aryloxy, heteroaryl, cycloheteroalkyl, heteroarylalkyl, cycloheteroalkylalkyl, cyano, heteroarylaminocarboyl, cycloheteroalkylcarbonyl, cyanoalkyl, alkylaminoalkyl, hydroxyalkyl, hydroxyaryl, aryloxyalkyl, nitro, $NR^eR^f$, CHO, $CO_2$alkyl, alkyloxyalkyl, $CONR^eR^f$, $CH_2NR^eR^f$, $CO_2H$, $CH_2OH$, $CH_2NHC(O)R^eR^f$, $NHCOR^g$, $NHCONR^eR^f$, $NHSO_pR^g$, $—SO_2NR^eR^f$, $NR^eSO_2NR^eR^f$, or $NR^eSO_pR^g$;

$R^a$ and $R^b$ are independently selected from hydrogen, halogen, hydroxy, alkyl, alkenyl, alkynyl, alkoxy, aryl, aryloxy, heteroaryl, cycloheteroalkyl, heteroarylalkyl, cycloheteroalkylalkyl, cyano, heteroarylaminocarboyl, cycloheteroalkylcarbonyl, cyanoalkyl, alkylaminoalkyl, hydroxyalkyl, hydroxyaryl, aryloxyalkyl, alkyloxyalkyl, nitro, $NR^eR^f$, CHO, $CO_2$alkyl, $CONR^eR^f$, $CH_2NR^eR^f$, $CO_2H$, $CH_2OH$, $CH_2NR^eR^f$, $NHCOR^g$, $NHCONR^eR^f$, and $NHSO_2R^g$;

$R^c$ and $R^d$ are independently selected from hydrogen, alkyl, alkenyl, alkynyl, alkoxy, $NR^eR^f$, aryl, hydroxy, aryloxy, heteroaryl, cycloheteroalkyl, heteroarylalkyl, cycloheteroalkylalkyl, hydroxyaryl, and aryloxyalkyl;

$R^e$ and $R^f$ are independently at each occurrence selected from hydrogen, aryl, alkyl, alkenyl, alkynyl, alkoxy, amino, substituted amino, alkoxyalkyl, alkylaminoalkyl, dialkylaminoalkyl, heteroaryl, cycloheteroalkyl, heteroarylalkyl, cycloheteroalkylalkyl, cycloalkyl, and cycloalkylalkyl, provided $R^e$ and $R^f$ are not both alkoxy or amino;

or $R^e$ and $R^f$ at each occurrence can be taken together with the nitrogen to which they are attached to form a 5-, 6- or 7-membered heteroaryl or cycloheteroalkyl ring which contains 1, 2 or 3 hetero atoms which can be N, O or S;

$R^g$ and $R^i$ independently at each occurrence are selected from hydrogen, aryl, alkyl, alkenyl, alkynyl, alkoxy, amino, substituted amino, alkoxyalkyl, alkylaminoalkyl, dialkylaminoalkyl, heteroaryl, cycloheteroalkyl, heteroarylalkyl, cycloheteroalkylalkyl, cycloalkyl, and cycloalkylalkyl;

p is 0, 1 or 2;

r is 0, 1 or 2; and s is 0, 1 or 2.

Whether or not specifically listed, all compounds of the present invention include prodrugs and solvates thereof (including prodrug esters), as well as stereoisomers thereof, tautomers thereof, or pharmaceutically acceptable salts thereof. Aspects of preferred compounds include those described in numbered paragraphs 1-12, listed immediately below.

1. Compounds within the scope of formula (I), as defined above, including all stereoisomers thereof, tautomers thereof, or a pharmaceutically acceptable salt thereof, wherein:

Z is a cycloalkyl, cycloalkenyl, heterocycloalkyl, aryl, or heteroaryl ring where each ring is substituted by 0-4 $R^7$ and 0-1 $R^8$;

$R^6$ is hydrogen, halogen, hydroxy, $C_{1-4}$alkyl, trifluoromethyl, $C_{1-4}$alkoxy, —$C(O)NR^eR^f$, nitro, or cyano;

$R^7$ and $R^8$ are independently at each occurrence hydrogen, halogen, hydroxy, alkyl, alkenyl, alkynyl, alkoxy, aryl, aryloxy, heteroaryl, cycloheteroalkyl, heteroarylalkyl, cycloheteroalkylalkyl, cyano, heteroarylaminocarboyl, cycloheteroalkylcarbonyl, cyanoalkyl, alkylaminoalkyl, hydroxyalkyl, hydroxyaryl, aryloxyalkyl, alkoxyalkyl, nitro, oxo, —$O(CH_2)_vR^h$, $NR^eR^f$, CHO, $CO_2$alkyl, $CONR^eR^f$, $CH_2NR^eR^f$, $CO_2H$, $CH_2OH$, $CH_2NHC(O)R^eR^f$, $NR^gCOR^i$, $NR^gCONR^gSO_pR^i$, —$SO_2NR^eR^f$, $NR^gSO_2NR^eR^f$, or $NR^gSO_pR^i$;

or $R^7$ and $R^8$ located on adjacent atoms can be taken together to form an optionally substituted cycloalkyl, aryl, heteroaryl, or cycloheteroalkyl ring;

$R^h$ is selected from aminocarbonyl, $O(CH_2)_zO(CH2)_yR^i$, alkylamino, heterocycloalkyl, heteroaryl, and aryl; and v, y and z are independently at each occurrence selected from 0, 1 and 2.

2. Compounds within the scope of paragraph 1, as defined above, having the structure

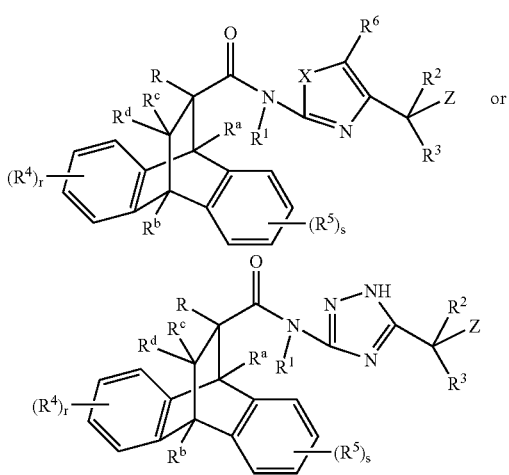

or a stereoisomer thereof, or a tautomer thereof, or a pharmaceutically acceptable salt thereof, wherein:

R is H or alkyl;

$R^a$ and $R^b$ are independently selected from H, $C_{1-4}$alkyl, OH, CN, $NO_2$, $NH_2$, CHO, $CO_2$alkyl, $CONR^eR^f$, and $CH_2NR^gR^h$; and $R^c$ and $R^d$ are independently selected from H, halogen, OH, CN, $NO_2$, $NH_2$, CHO, $CO_2$alkyl, $CONR^eR^f$ and $CH_2NR^eR^1$.

3. Compounds within the scope of formula (I), as defined above, including all stereoisomers thereof, tautomers thereof, or a pharmaceutically acceptable salt thereof, wherein:

R is H or $C_{1-4}$alkyl; and $R^c$ and $R^d$ are H.

4. Compounds within the scope of formula (I), as defined above, including all stereoisomers thereof, tautomers thereof, or a pharmaceutically acceptable salt thereof, wherein:

$R^a$ is selected from H and $NO_2$; and $R^b$ is selected from H, $CH_3$, Cl, Br, $NH_2$, CN, and $NO_2$.

5. Compounds within the scope of formula (I), as defined above, including all stereoisomers thereof, tautomers thereof, or a pharmaceutically acceptable salt thereof, wherein X is NH or S.

6. Compounds within the scope of formula (I), as defined above, including all stereoisomers and tautomers thereof, or a prodrug ester thereof, or a pharmaceutically acceptable salt thereof, wherein Z is a heterocycloalkyl, aryl, or heteroaryl ring, each ring substituted by 0-4 $R^7$ and 0-1 $R^8$.

7. Compounds within the scope of numbered paragraph 6, including stereoisomers thereof, tautomers thereof, or a pharmaceutically acceptable salt thereof, wherein:

Z is a phenyl, naphthyl, pyrimidyl, pyridinyl, pyridazinyl, piperazinyl, thiophenyl, thiazolyl, isoxazolyl, or imidazolyl ring;

$R^6$ is hydrogen;

$R^7$ and $R^8$ are independently at each occurrence:

(a) hydrogen, bromo, chloro, fluoro, $C_{1-4}$alkyl, arylalkyl, $OR^{11}$, oxo, $NO_2$, cyano, $NH_2$, —$NHC_{1-4}$alkyl, —$N(C_{1-4}alkyl)_2$, $SO_2C_{1-4}$alkyl, —$NHC(O)C_{1-4}$alkyl, —$C(O)N(C_{1-4}alkyl)_2$, —$C(O)NH(C_{1-4}alkyl)$, —$C(O)NH_2$, $CO_2H$, —$CO_2(C_{1-4}alkyl)$, or arylalkyl; or (b) a phenyl, naphthyl, pyrazolyl, pyrimidinyl, pyridinyl, isoxazolyl, indolyl, or morpholinyl ring; each of which is optionally further substituted by 1-3 $R^{13}$; or (c) $R^7$ and $R^8$ located on adjacent atoms can be taken together to form a dioxole or phenyl ring, where each ring is optionally further substituted;

$R^{11}$ at each occurrence is selected from hydrogen, $C_{1-4}$alkyl, $(CH_2)_vC(O)NH_2$, $(CH_2)_v$heteroaryl, $(CH_2)_vO(CH_2)_vO(CH_2)_zOR^{12}$, $(CH_2)_vN(C_{1-4}alkyl)_2$, $(CH_2)_v$heterocycloalkyl, and $(CH_2)_v$phenyl;

$R^{12}$ is hydrogen or $C_{1-4}$alkyl; and $R^{13}$ is halogen, oxo, $NH_2$, hydroxy, $C_{1-4}$alkyl, $C_{1-4}$alkoxy, —$(CH_2)$aryl, or heterocycloalkyl.

8. Compounds within the scope of numbered paragraphs 6 and 7, as defined above, including all stereoisomers thereof, tautomers thereof, or a pharmaceutically acceptable salt thereof, wherein Z is selected from:

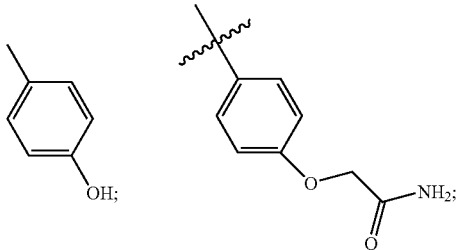

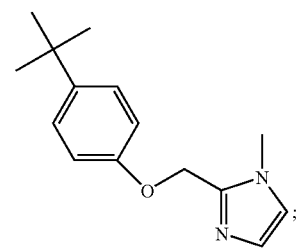

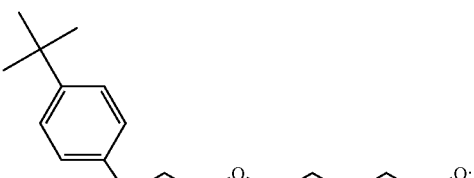

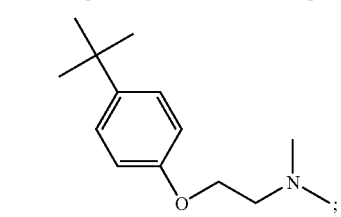

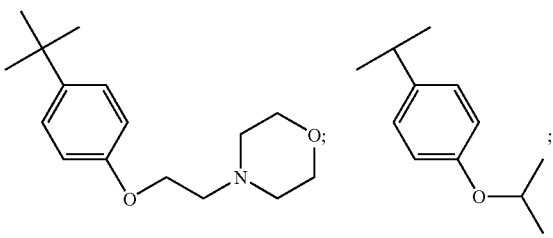

-continued
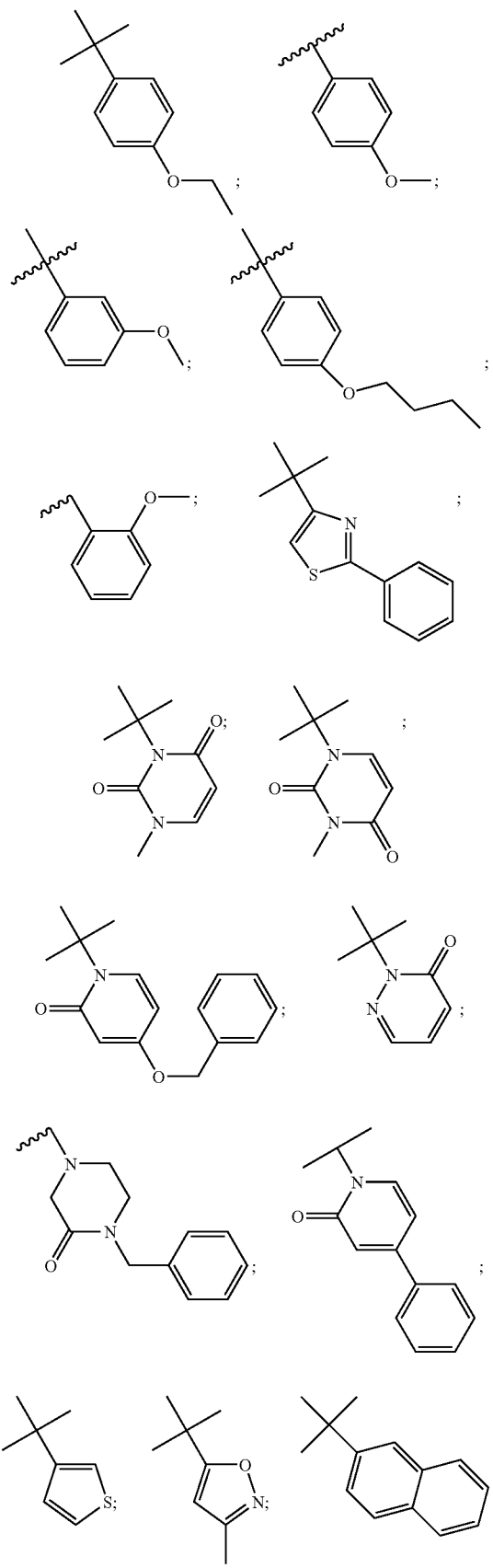
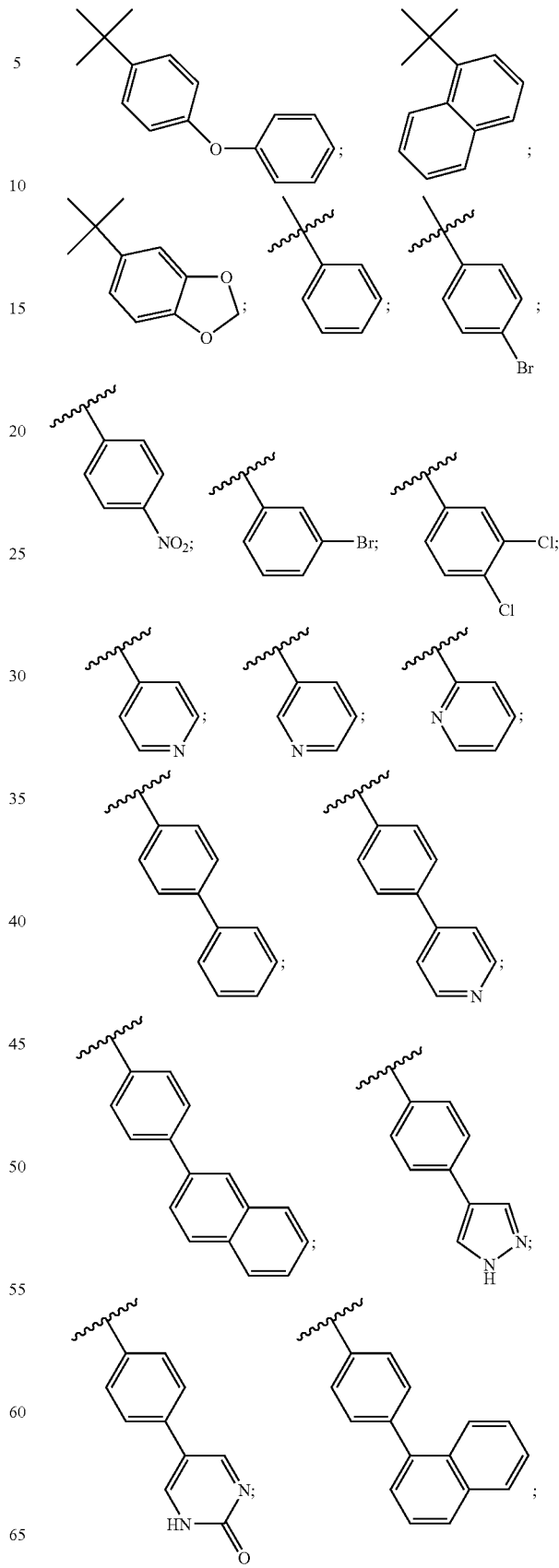

-continued
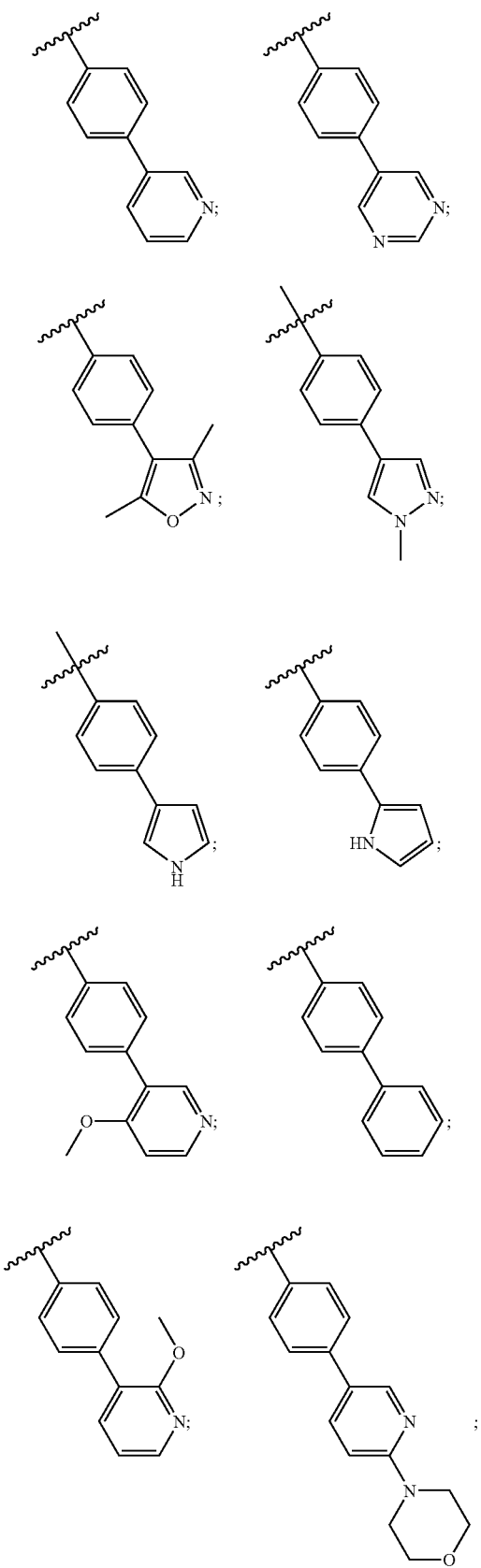
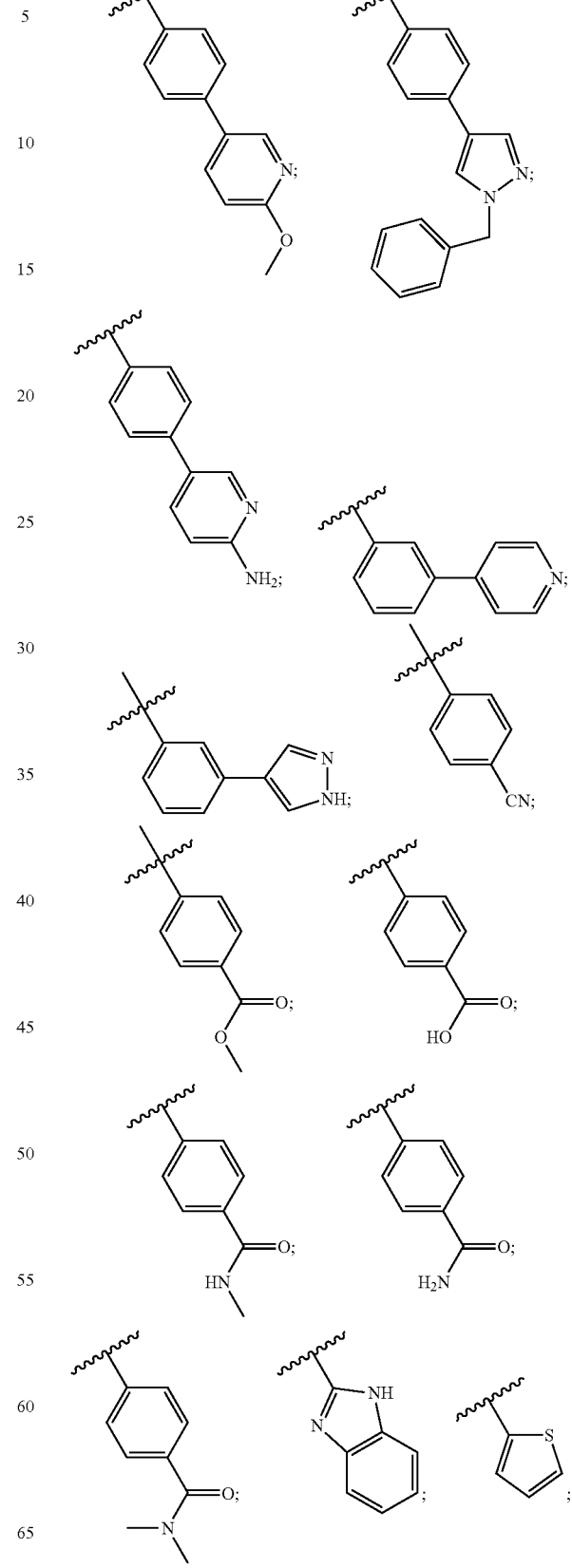

-continued

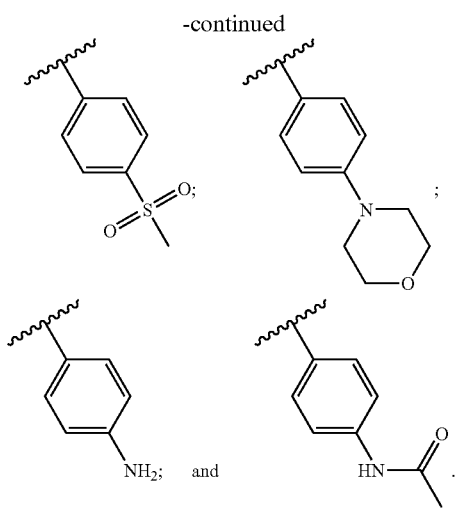

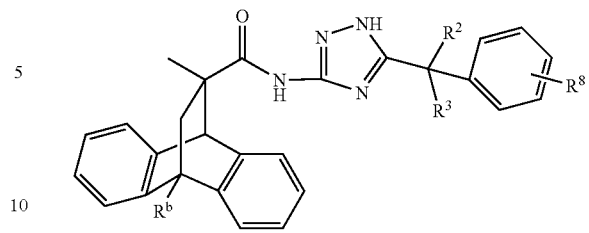

9. Compounds within the scope of formula (I), as defined above, including all stereoisomers thereof, tautomers thereof, or a pharmaceutically acceptable salt thereof, wherein:

$R^2$ is hydrogen, halogen, or hydroxy; and $R^3$ is hydrogen, halogen, hydroxy, alkyl, alkenyl, alkynyl, alkoxy, cyano, nitro, $NR^eR^f$, or CHO;

or $R^2$ and $R^3$ combine to form =O or a double bond, wherein the double bond is substituted by hydrogen, aryl, alkyl, alkenyl, alkynyl, alkoxy, amino, substituted amino, alkoxyalkyl, alkylaminoalkyl, dialkylaminoalkyl, heteroaryl, heterocycloalkyl, heteroarylalkyl, heterocycloalkylalkyl, cycloalkyl, or cycloalkylalkyl.

10. Compounds within the scope of formula (I), as defined above, including all stereoisomers thereof, tautomers thereof, or a pharmaceutically acceptable salt thereof, wherein:

$R^2$ and $R^3$ are, independently, hydrogen, halogen, or hydroxy;

or $R^2$ and $R^3$ combine to form =O.

11. Compounds within the scope of numbered paragraph 5, as defined above, having the formula:

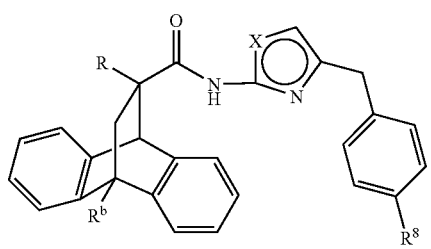

including all stereoisomers thereof, tautomers thereof, or a pharmaceutically acceptable salt thereof, wherein:

R is $C_{1-4}$alkyl;

$R^8$ is $C_{1-4}$alkoxy; halogen, pyrimidine, isoxazole, pyrazole, or pyridine, where the $C_{1-4}$alkoxy; halogen, pyrimidine, isoxazole, pyrazole, or pyridine, groups are substituted by hydrogen, morpholinyl, $C_{1-4}$alkoxy, or $C_{1-4}$alkyl; and $R^b$ is selected from H, $CH_3$, Cl, Br, and CN.

12. Compounds within the scope of numbered paragraph 2, as defined above, having the formula:

including all stereoisomers thereof, or a pharmaceutically acceptable salt thereof, wherein:

$R^2$ and $R^3$ are independently hydrogen, halogen, hydroxy, alkyl, alkenyl, alkynyl, alkoxy, cyano, nitro, $NR^eR^f$, or CHO;

or $R^2$ and $R^3$ combine to form =O or a double bond, wherein the double bond is substituted by hydrogen, aryl, alkyl, alkenyl, alkynyl, alkoxy, amino, substituted amino, alkoxyalkyl, alkylaminoalkyl, dialkylaminoalkyl, heteroaryl, heterocycloalkyl, heteroarylalkyl, heterocycloalkylalkyl, cycloalkyl, or cycloalkylalkyl; and $R^b$ is selected from H, $CH_3$, Cl, Br, $NO_2$, and CN.

Individual or groups of variable definitions of the above-described preferred aspects may replace related variables of other aspects to form other preferred aspects of the present invention.

In another aspect of the present invention, pharmaceutical compositions are provided that are useful in treating endocrine disorders, rheumatic disorders, collagen diseases, dermatologic disease, allergic disease, ophthalmic disease, respiratory disease, hematologic disease, gastrointestinal disease, inflammatory disease, autoimmune disease, diabetes, obesity, and neoplastic disease, as well as other uses as described herein, which includes a therapeutically effective amount (depending upon use) of a compound of formula I of the invention and a pharmaceutically acceptable carrier.

In still another aspect, the present invention provides a method of treating endocrine disorders, rheumatic disorders, collagen diseases, dermatologic disease, allergic disease, ophthalmic disease, respiratory disease, hematologic disease, gastrointestinal disease, inflammatory disease, autoimmune disease, diabetes, obesity, and neoplastic disease, diseases that are associated with the expression product of a gene whose transcription is stimulated or repressed by glucocorticoid receptors, or a method of treating a disease associated with AP-1- and/or NF-κB-induced transcription, or a method for preventing, inhibiting onset of or treating a disease associated with AP-1 and/or NF-κB dependent gene expression, wherein the disease or disorder is associated with the expression of a gene under the regulatory control of AP-1 and/or NF-κB, including inflammatory and immune diseases and disorders as described hereinafter, which includes the step of administering a therapeutically effective amount of a compound of formula I of the invention to a patient in need of treatment.

Another aspect of the present involves a method for treating a disease associated with the expression product of a gene whose transcription is stimulated or repressed by glucocorticoid receptors, or a method of treating a disease associated with AP-1- and/or NF-κB-induced transcription, or a method for preventing, inhibiting onset of or treating a disease associated with AP-1 and/or NF-κB dependent gene expression, wherein the disease is associated with the expression of a gene under the regulatory control of AP-1 and/or NF-κβ, such as inflammatory and immune disorders, cancer and tumor disorders, such as solid tumors, lymphomas and leukemia, and fungal infections such as mycosis fungoides.

The term "disease associated with GR transactivation," as used herein, refers to a disease associated with the transcription product of a gene whose transcription is transactivated by a GR. Such diseases include, but are not limited to: osteoporosis, diabetes, glaucoma, muscle loss, facial swelling, personality changes, hypertension, obesity, depression, and AIDS, the condition of wound healing, primary or secondary andrenocortical insufficiency, and Addison's disease.

The term "treat", "treating", or "treatment," in all grammatical forms, as used herein refers to the prevention, reduction, or amelioration, partial or complete alleviation, or cure of a disease, disorder, or condition, wherein prevention indicates treatment of a person at risk for developing a disease.

The terms "glucocorticoid receptor" and "GR," as used herein, refer either to a member of the nuclear hormone receptor family of transcription factors which bind glucocorticoids and either stimulate or repress transcription, or to GR-beta. These terms, as used herein, refer to glucocorticoid receptor from any source, including but not limited to: human glucocorticoid receptor as disclosed in Weinberger, et al. *Science* 228, pp. 640-742, (1985), and in Weinberger, et al. *Nature,* 318, pp. 670-672 (1986); rat glucocorticoid receptor as disclosed in Miesfeld, R. *Nature,* 312, pp. 779-781 (1985); mouse glucocortoid receptor as disclosed in Danielson, M. et al. *EMBO J.,* 5, 2513; sheep glucocorticoid receptor as disclosed in Yang, K., et al. *J. Mol. Endocrinol.* 8, pp. 173-180 (1992); marmoset glucocortoid receptor as disclosed in Brandon, D. D., et al, *J. Mol. Endocrinol.* 7, pp. 89-96 (1991); and human GR-beta as disclosed in Hollenberg, S M. et al. *Nature,* 318, 635, 1985, Bamberger, C. M. et al. *J. Clin Invest.* 95, 2435 (1995).

The term, "disease associated with AP-1-dependent gene expression," as used herein, refers to a disease associated with the expression product of a gene under the regulatory control of AP-1. Such diseases include, but are not limited to: inflammatory and immune diseases and disorders; cancer and tumor disorders, such as solid tumors, lymphomas and leukemia; and fungal infections such as mycosis fungoides.

The term "inflammatory or immune associated diseases or disorders" is used herein to encompass any condition, disease, or disorder that has an inflammatory or immune component, including, but not limited to, each of the following conditions: transplant rejection (e.g., kidney, liver, heart, lung, pancreas (e.g., islet cells), bone marrow, cornea, small bowel, skin allografts, skin homografts (such as employed in burn treatment), heart valve xenografts, serum sickness, and graft vs. host disease, autoimmune diseases, such as rheumatoid arthritis, psoriatic arthritis, multiple sclerosis, Type I and Type II diabetes, juvenile diabetes, obesity, asthma, inflammatory bowel disease (such as Crohn's disease and ulcerative colitis), pyoderma gangrenum, lupus (systemic lupus erythematosis), myasthenia gravis, psoriasis, dermatitis, dermatomyositis; eczema, seborrhoea, pulmonary inflammation, eye uveitis, hepatitis, Grave's disease, Hashimoto's thyroiditis, autoimmune thyroiditis, Behcet's or Sjorgen's syndrome (dry eyes/mouth), pernicious or immunohaemolytic anaemia, atherosclerosis, Addison's disease (autoimmune disease of the adrenal glands), idiopathic adrenal insufficiency, autoimmune polyglandular disease (also known as autoimmune polyglandular syndrome), glomerulonephritis, scleroderma, morphea, lichen planus, viteligo (depigmentation of the skin), alopecia areata, autoimmune alopecia, autoimmune hypopituatarism, Guillain-Barre syndrome, and alveolitis; T-cell mediated hypersensitivity diseases, including contact hypersensitivity, delayed-type hypersensitivity, contact dermatitis (including that due to poison ivy), uticaria, skin allergies, respiratory allergies (hayfever, allergic rhinitis) and gluten-sensitive enteropathy (Celiac disease); inflammatory diseases such as osteoarthritis, acute pancreatitis, chronic pancreatitis, acute respiratory distress syndrome, Sezary's syndrome and vascular diseases which have an inflammatory and or a proliferatory component such as restenosis, stenosis and artherosclerosis. Inflammatory or immune associated diseases or disorders also includes, but is not limited to: endocrine disorders, rheumatic disorders, collagen diseases, dermatologic disease, allergic disease, ophthalmic disease, respiratory disease, hematologic disease, gastrointestinal disease, inflammatory disease, autoimmune disease, congenital adrenal hyperplasia, nonsuppurative thyroiditis, hypercalcemia associated with cancer, juvenile rheumatoid arthritis, Ankylosing spondylitis, acute and subacute bursitis, acute nonspecific tenosynovitis, acute gouty arthritis, post-traumatic osteoarthritis, synovitis of osteoarthritis, epicondylitis, acute rheumatic carditis, pemphigus, bullous dermatitis herpetiformis, severe erythema multiforme, exfoliative dermatitis, seborrheic dermatitis, seasonal or perennial allergic rhinitis, bronchial asthma, contact dermatitis, atopic dermatitis, drug hypersensitivity reactions, allergic conjunctivitis, keratitis, herpes zoster ophthalmicus, iritis and iridocyclitis, chorioretinitis, optic neuritis, symptomatic sarcoidosis, fulminating or disseminated pulmonary tuberculosis chemotherapy, idiopathic thrombocytopenic purpura in adults, secondary thrombocytopenia in adults, acquired (autoimmune) hemolytic anemia, leukemias and lymphomas in adults, acute leukemia of childhood, regional enteritis, autoimmune vasculitis, multiple sclerosis, chronic obstructive pulmonary disease, solid organ transplant rejection, sepsis. Preferred treatments include treatment of transplant rejection, rheumatoid arthritis, psoriatic arthritis, multiple sclerosis, Type 1 diabetes, asthma, inflammatory bowel disease, systemic lupus erythematosis, psoriasis and chronic pulmonary disease.

In addition, in accordance with the present invention a method of treating a disease associated with AP-1-induced or NF-κB-induced transcription is provided wherein a compound of formula I of the invention is administered to a patient in need of treatment in a therapeutically effective amount to induce NHR transrepression of the AP-1-induced or NF-κB-induced transcription, thereby treating the disease.

Other therapeutic agents, such as those described hereafter, may be employed with the compounds of the invention in the present methods. In the methods of the present invention, such other therapeutic agent(s) may be administered prior to, simultaneously with or following the administration of the compound(s) of the present invention.

In a particular embodiment, the compounds of the present invention are useful for the treatment of the aforementioned exemplary disorders irrespective of their etiology, for example, for the treatment of transplant rejection, rheumatoid arthritis, inflammatory bowel disease, and viral infections.

Methods of Preparation

The compounds of the present invention may be synthesized by many methods available to those skilled in the art of organic chemistry. General synthetic schemes, in accordance with the present invention, for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Additionally, the various steps in the synthesis may be performed in an alternate sequence in order to give the desired compound or compounds. Examples of compounds of the present invention prepared by methods described in the general schemes are given in the preparations and examples section set out hereinafter.

As illustrated below, compounds of Formula I are generally synthesized by the formation of the amide from the "core" acid and the "side chain" amine.

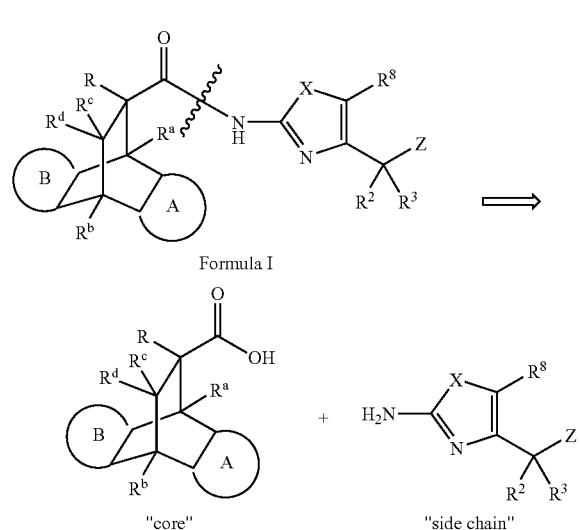

Synthesis of the core acid is described in co-pending application U.S. Ser. No. 10/621,909, which is incorporated by reference in its entirety.

There are many methods for synthesizing various side chain amines known to one skilled in the art of organic synthesis. Scheme 1 illustrates a number of classic methods for synthesizing reactive intermediates 1-6 which are then used to form heteroaryl amines 7 and 8.

SCHEME 1

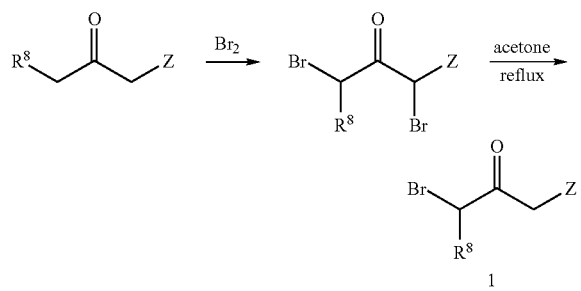

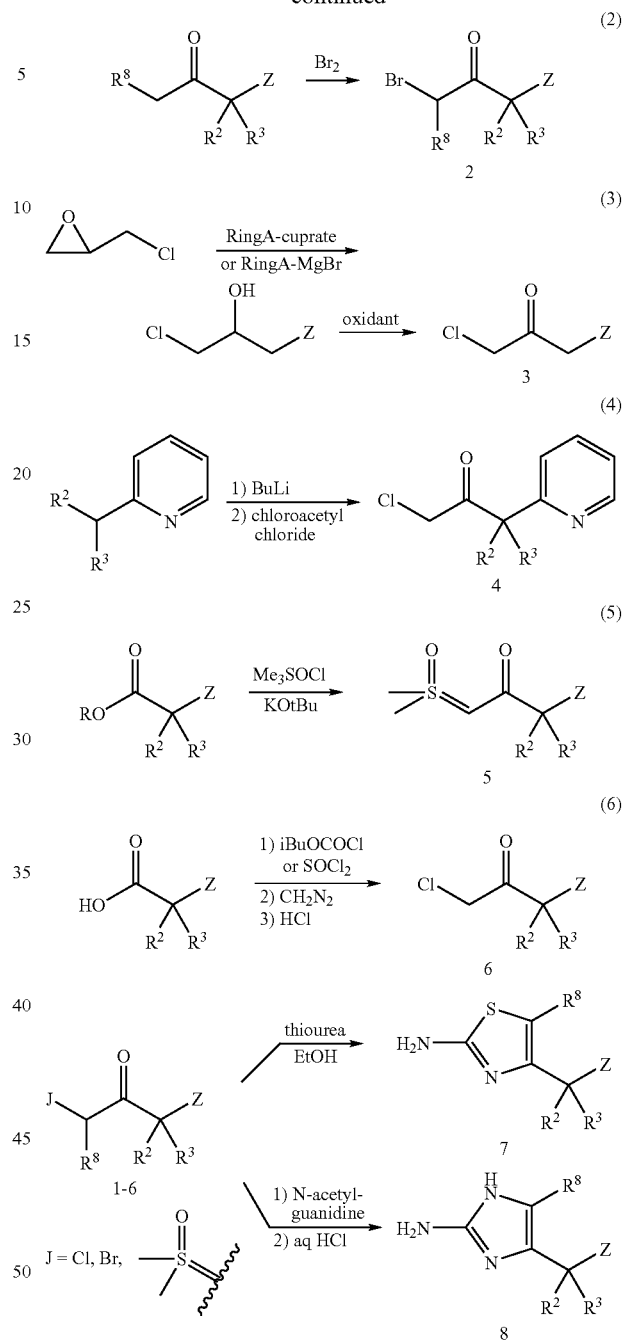

Reaction (1) shows typical conditions for brominating alpha to a ketone. In this specific case, bromination occurs first at the benzylic position and then at the desired R8-substituted position. Using the procedure of Chi et al (*Org. Lett.* 2003, 5, 411-414), dibromination followed by debromination with acetone yields the desired alpha-bromoketone 1. Reaction (2) is the same transformation as reaction (1) but when the methylene adjacent to Z is substituted, bromination occurs selectively or exclusively at the desired position to give structure 2. Reaction (3) is a summary of the method of Takano (*Heterocycles* 1989, 29, 1861-1864; also see Zhao et al *Bioorg. Med. Chem. Lett.* 1998, 6, 2531-2539) which describes the use of cuprates to open epichlorohydrin to form chlorohydrins. It should be noted that Grignard reagents themselves open epoxides either in the presence or absence of copper salts (see, Mazzocchi et al *Synth Commun.* 1986, 309-312; *Eur. J. Med. Chem.* 1979, 14, 165-170). Oxidation of the chlorohydrin using Dess-Martin periodinane or other suitable oxidant yields the desired chloromethylketone 3. Another method of forming chloromethylketones is shown in reaction (4). Lithiation of activated methyl groups using butyllithium followed by reaction with chloroacetylchloride (or ethyl chloroacetate, *Khim. Geterot. Soed.* 1986, 6, 802-809) directly provides the chloromethylketone 4 intermediate. Reaction (5) shows the method of Nugent et al (*J. Org. Chem.* 2004, 69, 1629-1633) which uses dimethylsulfoxonium methylide to nucleophilically add to esters forming reactive β-keto sulfur ylides 5. Lastly, a widely used acid homologation procedure shown in reaction (6) involves the conversion of a carboxylic acid to a mixed anhydride (or acid chloride) followed by treatment with diazomethane and then HCl to form the chloromethylketone 6.

Scheme 1 also shows that reactive intermediates 1-6 can be treated with thiourea with or without added acid to yield the desired substituted 2-aminothiazoles 7. Synthesis of substituted 2-aminoimidazoles 8 is best accomplished using the procedure of Little and Webber (*J. Org. Chem.* 1994, 59, 7299-7305) using N-acetylguanidine as the nucleophile followed by acid hydrolysis of the acetyl group.

Alternate syntheses of 2-aminoimidazoles are listed in Scheme 2.

As described in Scheme 2, reaction (1), an aminomethylketone is condensed with cyanamide to form an intermediate guanidinomethylketone which undergoes dehydration upon treatment with HCl (see, Lancini and Lazzari, *J. Het. Chem.* 1966, 3, 152-154) to form compound 9. Aminomethyl ketones can be synthesized from the reactive intermediates 1-6 (Scheme 1) using standard procedures known to one skilled in the art. Reaction (2) details the procedure of Home et al (*Tetrahedron. Lett.* 1993, 34, 6981-6984) to make substituted 2-aminoimidazoles. Briefly, commercially available 2-aminoimidazole reacts with aldehydes to form hydroxyalkylaminoimidazoles which are conveniently protected in situ with a CBZ group in situ to facilitate purification. Catalytic hydrogenation of this intermediate under mild conditions first reduces the CBZ group to give the hydroxyalkylaminoimidazoles 10. Prolonged hydrogenation under stronger conditions reduces the benzylic hydroxyl group to give compound 9. If the intermediate hydroxyalkylaminoimidazole is first oxidized (using Dess-Martin periodinane for example) and then treated with under mild hydrogenation conditions, the 2-amino-4-ketoimidazole compound 11 is formed.

Scheme 3 illustrates several additional synthetic transformations for the preparation of substituted 2-aminothiazoles.

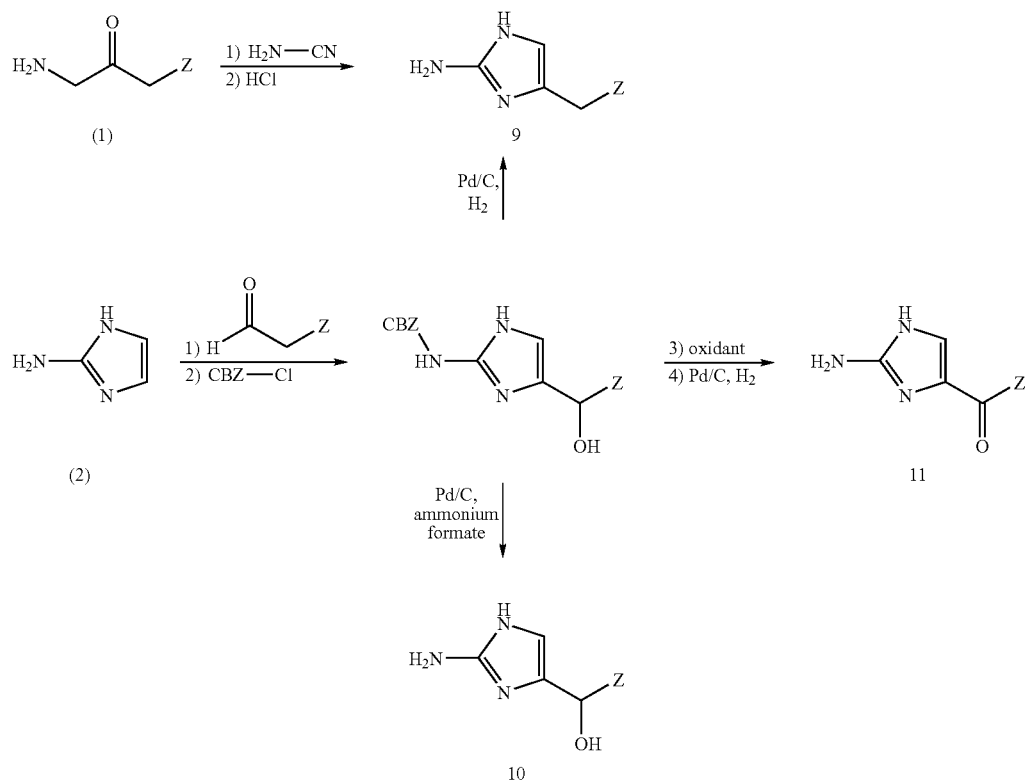

SCHEME 3

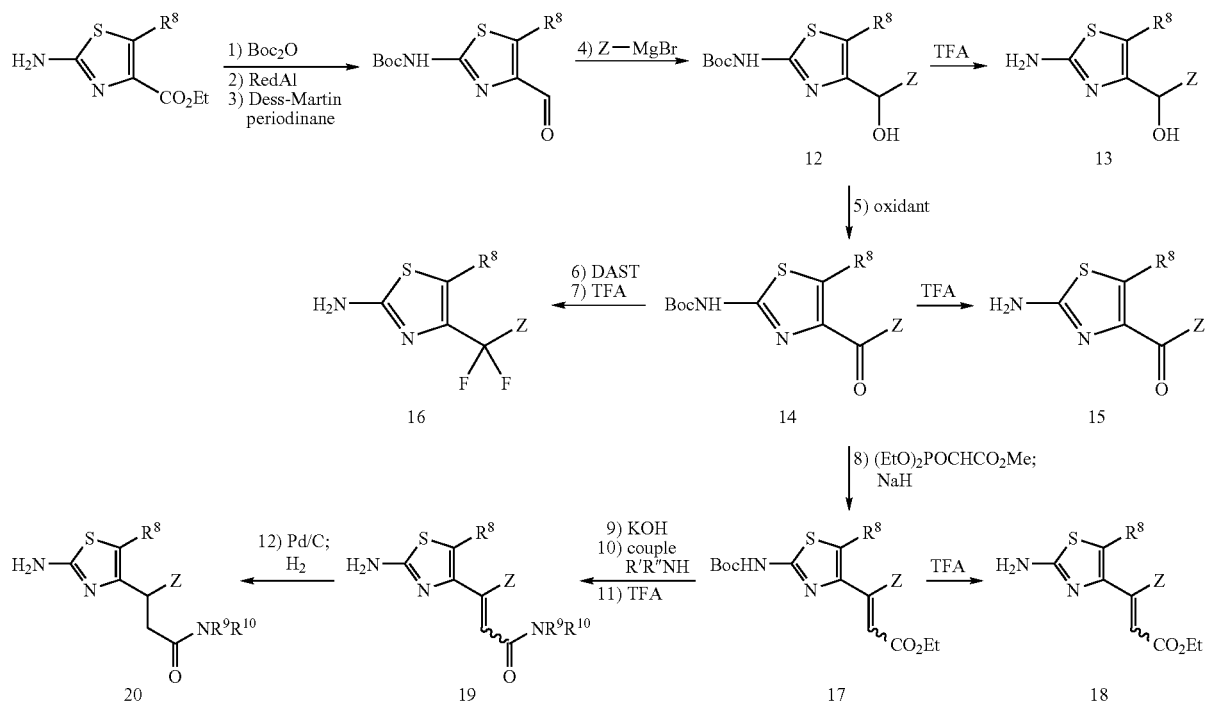

Starting from commercially available 2-aminothiazole-4-carboxylic ester, the amino group is protected using Boc anhydride. The ester moiety is reduced with RedAl. Oxidation of the resultant alcohol with Dess-Martin periodinane gives the aldehyde which can undergo reactions with organometallic reagents such as Grignard reagents to give compound 12. TFA deprotection of 12 gives amine 13 which is ready for coupling to different core acids to make compounds of Formula I. Alternatively, oxidation of intermediate 12 gives the keto compound 14 that can either be deprotected to give compound 15 or fluoridated using DAST and deprotected to give compound 16. Compound 14 may also be homologated using a Homer-Wadsworth-Emmons procedure to give the α,β-unsaturated ester 17. Ester 17 can be deprotected with TFA to give compound 18, the ester converted using standard procedures to amide 19, and lastly reduced to amide 20.

As shown in Scheme 4, compounds 7-11, 13, 15, 16, 18, 19, and 20 may be coupled to the core carboxylic acids to form compounds of Formula I.

SCHEME 4

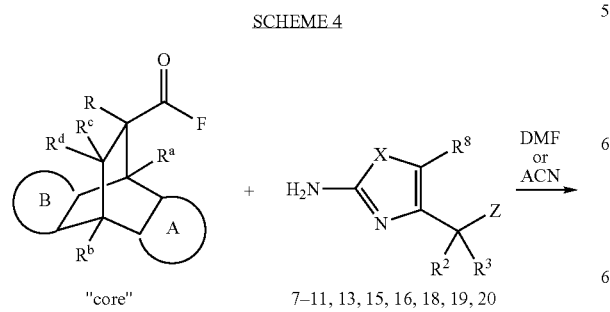

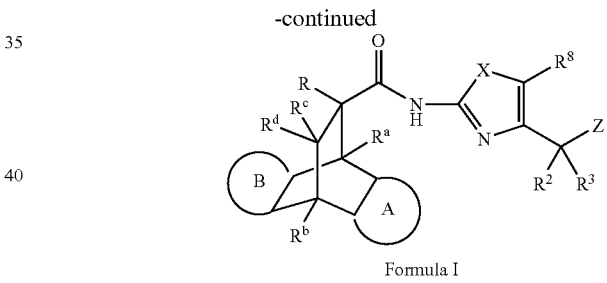

Formula I

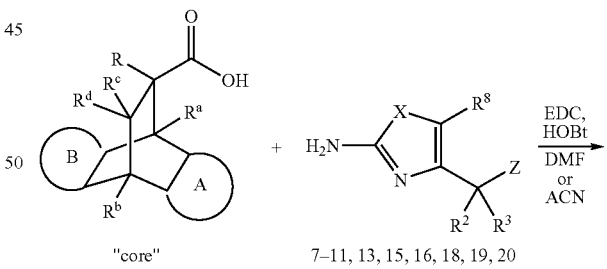

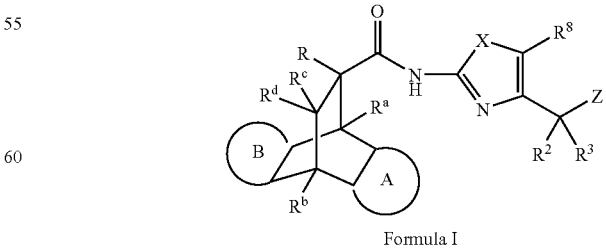

Formula I

The coupling may proceed via the use of preactivated cores such as acid fluorides, or the acids may be coupled in situ using well-established peptide coupling reagents such as carbodiimide reagents mixed with hydroxybenzothiazole (or other methods described in Chamberlin et al *Chem Rev* 1997, 97, 2243-2266).

Alternatively, compounds of Formula I may also be synthesized by coupling an intermediate substituted 2-aminothiazole or 2-aminoimidazole first and then using additional chemistry to elaborate the substitution on the side chain as shown in Scheme 5.

Starting with the bromobenzyl side chain 21, this compound can be further elaborated to compounds of Formula I using: (1) a Suzuki reaction to form biaryl systems via compound 22, (2) Buchwald aminations to form amines via compound 23, or (3) palladium-mediated cyanation to form the nitrile 24. Compound 24 can be hydrolyzed to the carboxylic acid 25 and coupled to amines using standard peptide coupling reagents to form amides 26. Alternatively, the nitrile of compound 24 can be reduced to an aminom-

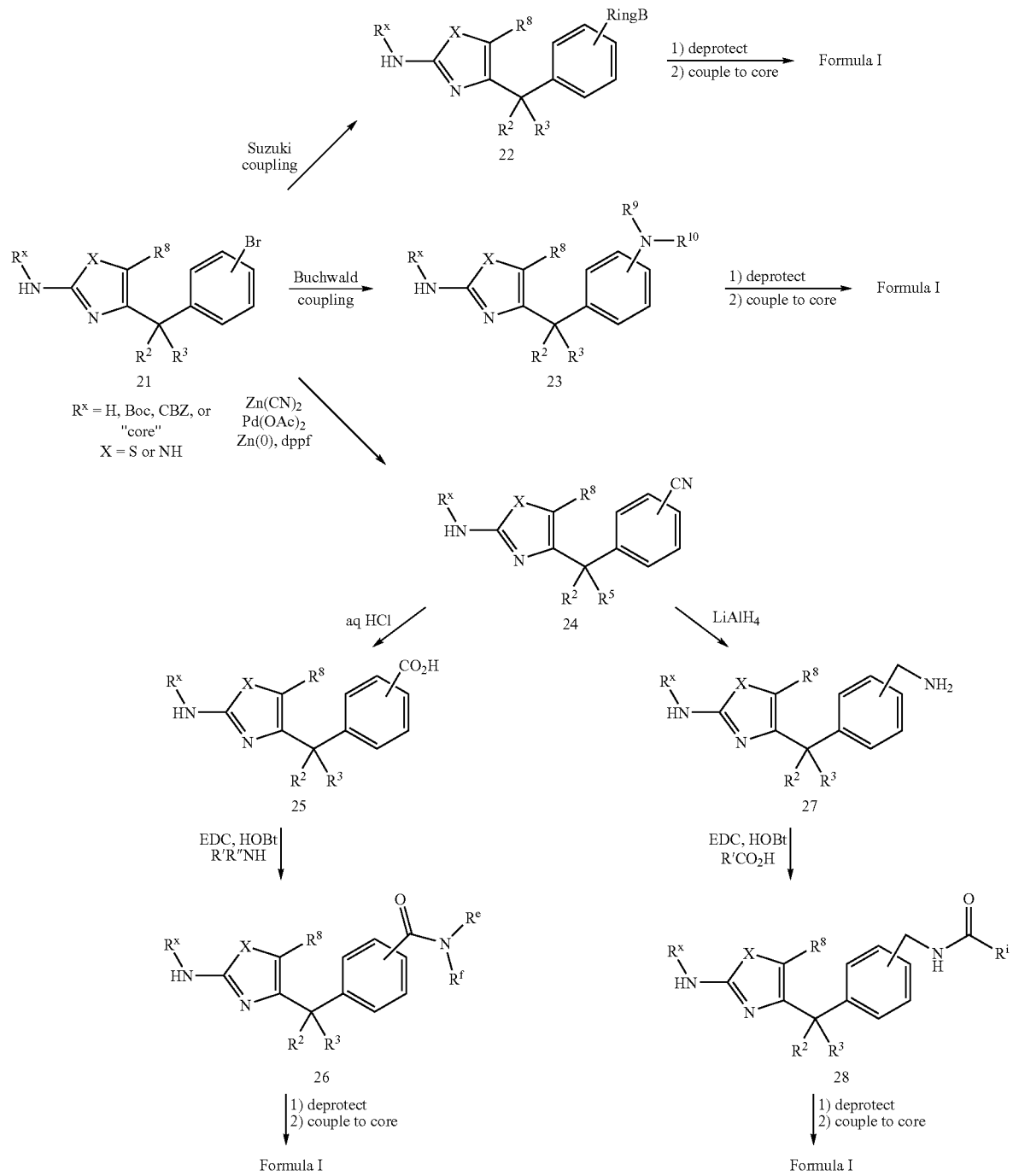

ethyl compound 27 and subsequently functionalized by acylation with acid chlorides, sulfonyl chlorides, isocyanates, and the like to form amides, sulfonamides, and ureas respectively of the structure 28. When the Rx group is CBZ, it can be removed by hydrogenation to give the free amine which may be coupled to the core molecule. When the Rx group is Boc, it can be removed with trifluoroacetic acid to give the free amine which may be coupled to the core molecule.

Scheme 6 depicts additional examples of side chain amine elaboration.

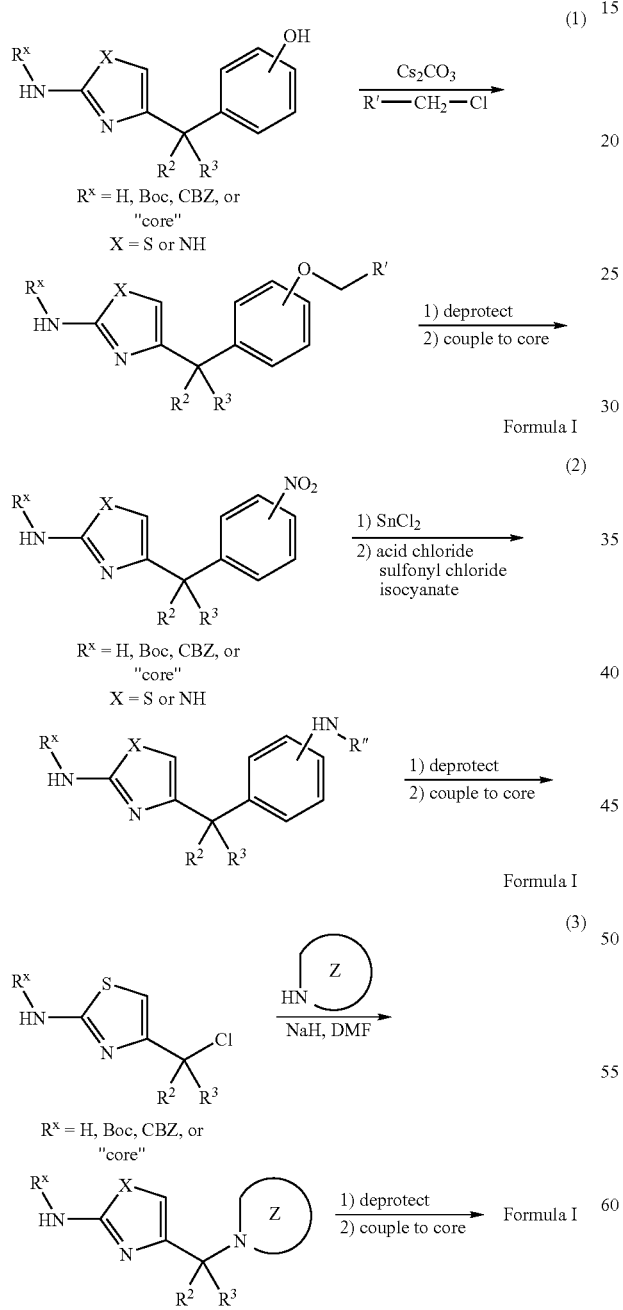

Reaction (1) illustrates a number of diverse side chains that can be synthesized from a phenol. Using standard alkylative conditions (e.g. $Cs_2CO_3$ and alkyl chloride in polar solvent) or Mitsunobu conditions (the phenol, alkyl alcohol, diethylazodicarboxylate, and triphenylphosphine), phenols can be converted efficiently into ethers. Reaction (2) shows how a nitro group can be reduced with tin (II) chloride and then coupled with acid chlorides, sulfonyl chlorides, or isocyanates to form amides, sulfonamides, and ureas respectively. Reaction (3) shows how a 2-amido-4-chloromethylthiazole or N-protected variants can be reacted with heterocyclic nitrogen-bearing nucleophiles to provide heterocyclic derivatives at the 4-position of the thiazole. When the 2-amino group is protected by a Boc or CBZ protecting group, it can be removed and the free amino coupled to the core acid to give compounds of Formula I.

DEFINITION OF TERMS

Unless otherwise indicated, the term "lower alkyl", "alkyl" or "alk" as employed herein alone or as part of another group includes both straight and branched chain hydrocarbons, containing 1 to 20 carbons, preferably 1 to 10 carbons, more preferably 1 to 8 carbons, in the normal chain, and may optionally include an oxygen or nitrogen in the normal chain. Accordingly, the term "lower alkyl", "alkyl" or "alk" includes groups such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including 1 to 4 substituents such as halo, for example F, Br, Cl or I, alkoxy, aryl, aryloxy, aryl(aryl) or diaryl, arylalkyl, arylalkyloxy, alkenyl, cycloalkyl, cycloalkylalkyl, cycloalkylalkyloxy, amino, hydroxy, hydroxyalkyl, acyl, heteroaryl, heteroaryloxy, HO—N=, cycloheteroalkyl, alkyloxycarbonyl, alkoxyoximyl, arylheteroaryl, arylalkoxycarbonyl, heteroarylalkyl, heteroarylalkoxy, aryloxyalkyl, aryloxyaryl, alkylamido, alkanoylamino, hydroxyalkyl(alkyl)amino carbonyl, arylcarbonylamino, nitro, cyano, thiol, haloalkyl, trihaloalkyl and/or alkylthio as well as other substituents listed below for aryl.

Unless otherwise indicated, the term "cycloalkyl" as employed herein alone or as part of another group includes saturated cyclic hydrocarbon groups containing 1 to 3 rings, including monocyclicalkyl, bicyclicalkyl and tricyclicalkyl, containing a total of 3 to 20 carbons forming the rings, preferably 3 to 10 carbons, forming the ring and which may be fused to 1 or 2 aromatic rings (defined below). Accordingly, the term "cycloalkyl" includes groups such as cyclopropyl, cyclobutyl, cyclopentyl, cyclohexyl, cycloheptyl, cyclooctyl, cyclodecyl and cyclododecyl, cyclohexenyl,

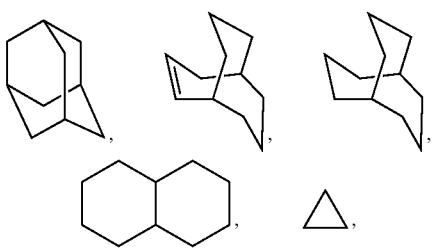

and the like as well as such groups including 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, amino, nitro, cyano, thiol and/or alkylthio and/or any of the substituents for alkyl.

The term "cycloalkenyl" as employed herein alone or as part of another group refers to cyclic hydrocarbons containing 3 to 12 carbons, preferably 5 to 10 carbons and 1 or 2 double bonds. Exemplary cycloalkenyl groups include cyclopentenyl, cyclohexenyl, cycloheptenyl, cyclooctenyl, cyclohexadienyl, and cycloheptadienyl, which may be optionally substituted as defined for cycloalkyl.

The term "cycloalkylene" as employed herein refers to a "cycloalkyl" group which includes free bonds and thus is a linking group such as

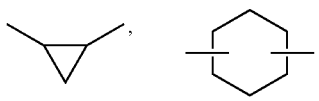

and the like, and may optionally be substituted as defined above for "cycloalkyl".

The term "alkanoyl" as used herein alone or as part of another group refers to alkyl linked to a carbonyl group.

Unless otherwise indicated, the term "lower alkenyl" or "alkenyl" as used herein by itself or as part of another group refers to straight or branched chain radicals of 2 to 20 carbons, preferably 2 to 12 carbons, and more preferably 1 to 8 carbons in the normal chain, which include one to six double bonds in the normal chain, and may optionally include an oxygen or nitrogen in the normal chain. Accordingly, the term "lower alkenyl" or "alkenyl" includes groups such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like as well as such groups including 1 to 4 substituents such as halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonylamino, nitro, cyano, thiol, alkylthio and/or any of the substituents for alkyl set out herein.

Unless otherwise indicated, the term "lower alkynyl" or "alkynyl" as used herein by itself or as part of another group refers to straight or branched chain radicals of 2 to 20 carbons, preferably 2 to 12 carbons and more preferably 2 to 8 carbons in the normal chain, which include one triple bond in the normal chain, and may optionally include an oxygen or nitrogen in the normal chain. Accordingly, the term "lower alkynyl" or "alkynyl" includes groups such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like as well as such groups including 1 to 4 substituents such as halogen, haloalkyl, alkyl, alkoxy, alkenyl, alkynyl, aryl, arylalkyl, cycloalkyl, amino, heteroaryl, cycloheteroalkyl, hydroxy, alkanoylamino, alkylamido, arylcarbonylamino, nitro, cyano, thiol, and/or alkylthio, and/or any of the substituents for alkyl set out herein.

The terms "arylalkenyl" and "arylalkynyl" as used alone or as part of another group refer to alkenyl and alkynyl groups as described above having an aryl substituent.

Where alkyl groups as defined above have single bonds for attachment to other groups at two different carbon atoms, they are termed "alkylene" groups and may optionally be substituted as defined above for "alkyl".

Where alkenyl groups as defined above and alkynyl groups as defined above, respectively, have single bonds for attachment at two different carbon atoms, they are termed "alkenylene groups" and "alkynylene groups", respectively, and may optionally be substituted as defined above for "alkenyl" and "alkynyl".

$(CH_2)_p$ and $(CH2)_q$, includes alkylene, allenyl, alkenylene or alkynylene groups, as defined herein, each of which may optionally include an oxygen or nitrogen in the normal chain, which may optionally include 1, 2, or 3 substituents which include alkyl, alkenyl, halogen, cyano, hydroxy, alkoxy, amino, thioalkyl, keto, $C_3$-$C_6$ cycloalkyl, alkylcarbonylamino or alkylcarbonyloxy; the alkyl substituent may be an alkylene moiety of 1 to 4 carbons which may be attached to one or two carbons in the $(CH_2)_p$ or $(CH2)_q$ group to form a cycloalkyl group therewith.

Examples of $(CH_2)_p$, $(CH_2)_q$, alkylene, alkenylene and alkynylene include

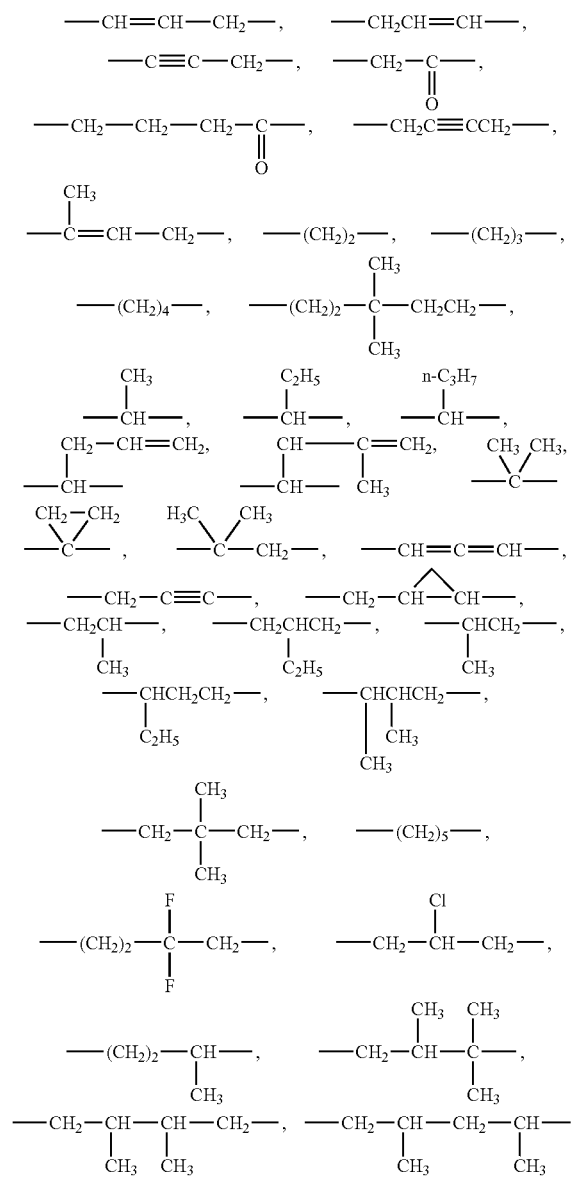

-continued

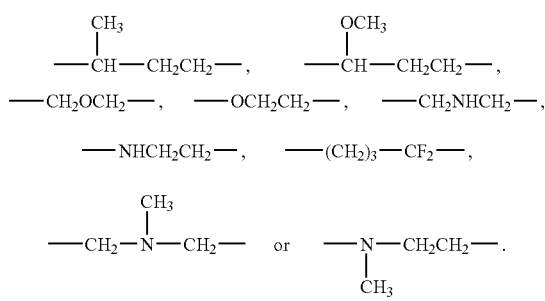

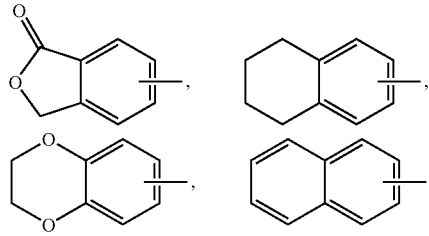

The term "halogen" or "halo" as used herein alone or as part of another group (e.g. $CF_3$ is a haloalkyl group) refers to chlorine, bromine, fluorine, and iodine, with chlorine fluorine or bromine being preferred.

The term "metal ion" refers to alkali metal ions such as sodium, potassium or lithium and alkaline earth metal ions such as magnesium and calcium, as well as zinc and aluminum.

Unless otherwise indicated, the term "aryl", as employed herein alone or as part of another group refers to monocyclic and bicyclic aromatic groups containing 6 to 10 carbons in the ring portion (such as phenyl or naphthyl including 1-naphthyl and 2-naphthyl) and may optionally include one to three additional rings fused to a carbocyclic ring or a heterocyclic ring (such as aryl, cycloalkyl, heteroaryl or cycloheteroalkyl rings. Accordingly, the term "aryl" includes, for example

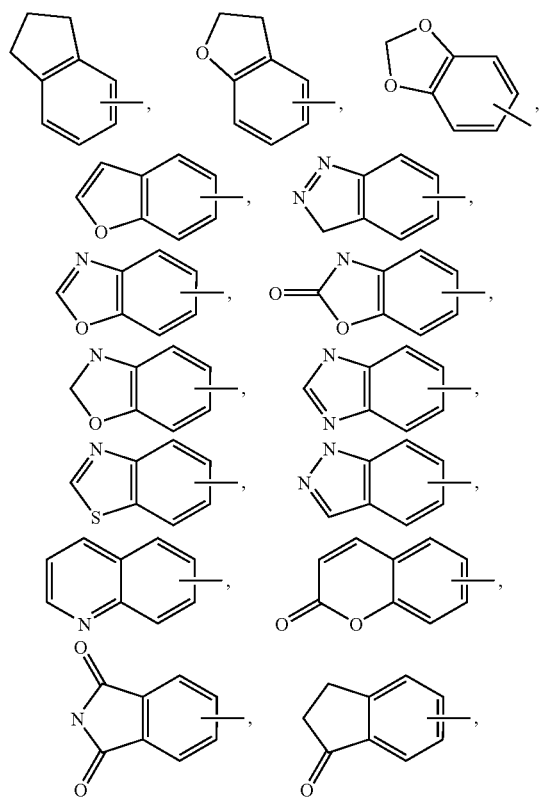

and may be optionally substituted through available carbon atoms with 1, 2, or 3 groups selected from hydrogen, halo, haloalkyl, alkyl, haloalkyl, alkoxy, haloalkoxy, alkenyl, trifluoromethyl, trifluoromethoxy, alkynyl, cycloalkyl-alkyl, cycloheteroalkyl, cycloheteroalkylalkyl, aryl, heteroaryl, arylalkyl, aryloxy, aryloxyalkyl, arylalkoxy, alkoxycarbonyl, arylcarbonyl, arylalkenyl, aminocarbonylaryl, arylthio, arylsulfmyl, arylazo, heteroarylalkyl, heteroarylalkenyl, heteroarylheteroaryl, heteroaryloxy, hydroxy, nitro, cyano, amino, substituted amino wherein the amino includes 1 or 2 substituents (substituents are described in definition for substituted amino, below), thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfmyl, arylsulfmylalkyl, arylsulfonylamino or arylsulfonaminocarbonyl, carboxy, cycloalkyl, arylalkoxy, aryloxycarbonyl, cycloalkylaminocarbonyl, cycloalkylalkylaminocarbonyl, alkoxycarbonylalkyl, alkoxyalkylaminocarbonyl, heteroarylaminocarbonyl, heteroarylalkylaminocarbonyl, arylalkylaminocarbonyl, N-hydroxyalkyl(N-alkyl)aminocarbonyl, cycloheteroalkylaminocarbonyl, cycloheteroalkylalkylaminocarbonyl, N-aryl(N-alkyl)aminocarbonyl, N-arylalkyl(N-cyanoalkyl)aminocarbonyl, dialkylaminoalkylaminocarbonyl, dialkylaminocarbonyl, alkyl-, arylalkyl- or aryl-cycloheteroalkylaminocarbonyl, N-dialkylaminoalkyl(N-alkyl or N-arylalkyl)aminocarbonyl, N-heteroarylalkyl(N-alkyl)aminocarbonyl, N-arylalkyl(N-alkyl)aminocarbonyl, N-dialkylamino(N-arylalkyl)aminocarbonyl, N-hydroxyalkyl(N-arylalkyl)aminocarbonyl, aminoalkyloxycarbonyl, cycloheteroalkylcarbonyl, N=N=N, alkylsulfonyl, aminosulfonyl, heteroarylaminosulfonyl, and/or any of the substituents for alkyl set out herein.

Unless otherwise indicated, the term "lower alkoxy", "alkoxy", "aryloxy" or "aralkoxy" as employed herein alone or as part of another group includes any of the above alkyl, aralkyl or aryl groups linked to an oxygen atom.

Unless otherwise indicated, the term "substituted amino" as employed herein alone or as part of another group refers to amino substituted with one or two substituents, which may be the same or different, such as alkyl, aryl, arylalkyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl or thioalkyl. These substituents may optionally be further substituted with a carboxylic acid and/or any of the substituents for alkyl as set out above. In addition, the amino substituents may be taken together with the nitrogen atom to which they are attached to form 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, 1-pyrrolidinyl, 1-piperidinyl, or 1-azepinyl, optionally substituted with alkyl, alkoxy, alkylthio, halo, trifluoromethyl or hydroxy.

Unless otherwise indicated, the term "lower alkylthio", alkylthio", "arylthio" or "aralkylthio" as employed herein alone or as part of another group includes any of the above alkyl, aralkyl or aryl groups linked to a sulfur atom.

Unless otherwise indicated, the term "lower alkylamino", "alkylamino", "acylamino", sulfonylamino, "arylamino", or "arylalkylamino" as employed herein alone or as part of another group includes any of the above alkyl, aryl or arylalkyl groups linked to a nitrogen atom.

Unless otherwise indicated, the term "acyl" as employed herein by itself or part of another group, as defined herein, refers to an organic radical linked to a carbonyl

group; examples of acyl groups include any of the R groups attached to a carbonyl, such as alkanoyl, alkenoyl, aroyl, aralkanoyl, heteroaroyl, cycloalkanoyl, cycloheteroalkanoyl and the like.

Unless otherwise indicated, the term "lower alkylamino", "alkylamino", "acylamino", "arylamino", or "arylalkylamino" as employed herein alone or as part of another group includes any of the above alkyl, aryl or arylalkyl acyl groups linked to a nitrogen atom. The term "acylamino", for example, includes the group —NHC(O)alkyl.

Unless otherwise indicated, the term "cycloheteroalkyl" as used herein alone or as part of another group refers to a 5-, 6- or 7-membered saturated or partially unsaturated ring which includes 1 to 2 hetero atoms such as nitrogen, oxygen and/or sulfur, linked through a carbon atom or a heteroatom, where possible, optionally via the linker $(CH_2)_p$ (where p is 0, 1, 2 or 3), such as

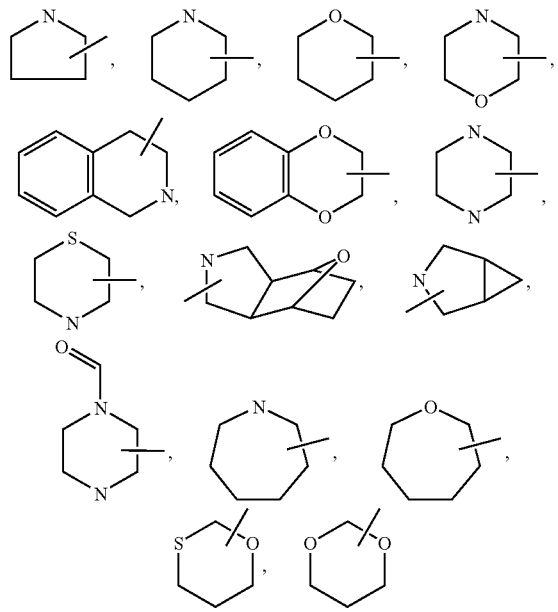

and the like. The above groups may include 1 to 4 substituents such as alkyl, halo, oxo and/or any of of the substituents for alkyl or aryl set out herein. In addition, any of the cycloheteroalkyl rings can be fused to a cycloalkyl, aryl, heteroaryl or cycloheteroalkyl ring.

Unless otherwise indicated, the term "heteroaryl" as used herein alone or as part of another group refers to a 5-, 6- or 7-membered aromatic ring which includes 1, 2, 3 or 4 hetero atoms such as nitrogen, oxygen or sulfur,and such rings fused to an aryl, cycloalkyl, heteroaryl or cycloheteroalkyl ring (e.g. benzothiophenyl, indolyl), and includes possible N-oxides, linked through a carbon atom or a heteroatom, where possible, optionally via the linker $(CH_2)_q$ (where q is 0, 1, 2 or 3). The heteroaryl group may optionally include 1 to 4 substituents such as any of the substituents for alkyl or aryl set out above. Examples of heteroaryl groups include the following:

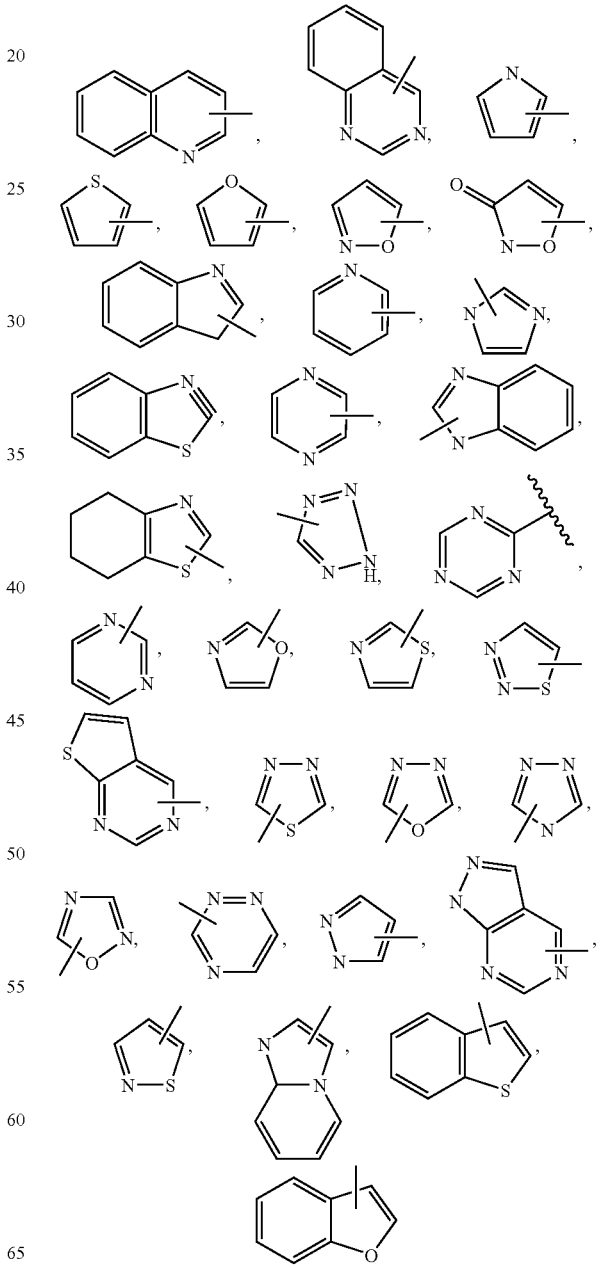

and the like.

Examples of A rings and B rings include, but are not limited to any of the 6-membered heteroaryl groups as defined above, 6-membered cycloheteroalkyl groups as defined above, and 6-membered aryl groups as defined above.

The term "cycloheteroalkylalkyl" as used herein alone or as part of another group refers to cycloheteroalkyl groups as defined above linked through a C atom or heteroatom to a $(CH_2)_p$ chain.

The term "heteroarylalkyl" or "heteroarylalkenyl" as used herein alone or as part of another group refers to a heteroaryl group as defined above linked through a C atom or heteroatom to a $-(CH_2)_q-$ chain, alkylene or alkenylene as defined above.

The term "polyhaloalkyl" as used herein refers to an "alkyl" group as defined above which includes from 2 to 9, preferably from 2 to 5, halo substituents, such as F or Cl, preferably F, such as $CF_3CH_2$, $CF_3$ or $CF_3CF_2CH_2$.

The term "polyhaloalkyloxy" as used herein refers to an "alkoxy" or "alkyloxy" group as defined above which includes from 2 to 9, preferably from 2 to 5, halo substituents, such as F or Cl, preferably F, such as $CF_3CH_2O$, $CF_3O$ or $CF_3CF_2CH_2O$.

The use of a circle in a ring of a chemical structures denotes an aromatic system. Accordingly the group

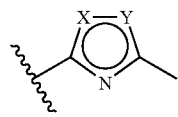

is a five-membered aromatic ring system, including tautomers where possible, containing nitrogen and variables X and Y. Where X is defined to be N, O, NH or S and Y is N, NH or $CR^6$, this includes ring system such as for example:

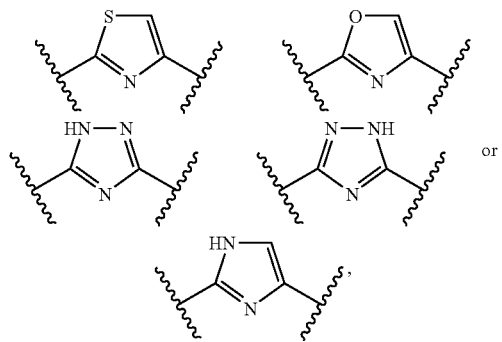

which are preferred embodiments of the variable "Z" in the present invention. More preferred are compounds where Z is the first, $4^{th}$ and $5^{th}$ structures drawn immediately above.

The term "prodrug" denotes a compound which, upon administration to a subject, undergoes chemical conversion by metabolic or chemical processes to yield a compound of the formula (I), and/or a salt and/or solvate thereof. For example, compounds containing a carboxy group can form physiologically hydrolyzable esters which serve as prodrugs by being hydrolyzed in the body to yield formula (I) compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula (I) include $C_{1-6}$alkylbenzyl, 4-methoxybenzyl, indanyl, phthalyl, methoxymethyl, $C_{1-6}$alkanoyloxy-$C_{1-6}$alkyl, e.g. acetoxymethyl, pivaloyloxymethyl or propionyloxymethyl, $C_{1-6}$alkoxycarbonyloxy-$C_{1-6}$alkyl, e.g. methoxycarbonyl-oxymethyl or ethoxycarbonyloxymethyl, glycyloxymethyl, phenylglycyloxymethyl, (5-methyl-2-oxo-1,3-dioxolen-4-yl)-methyl and other well known physiologically hydrolyzable esters used, for example, in the penicillin and cephalosporin arts. Such esters may be prepared by conventional techniques known in the art.

Prodrug ester examples include the following groups: (1-alkanoyloxy)alkyl such as,

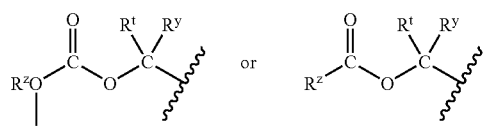

wherein $R^z$, $R^t$ and $R^y$ are H, alkyl, aryl or arylalkyl; however, $R^zO$ cannot be HO.

Examples of such prodrug esters include

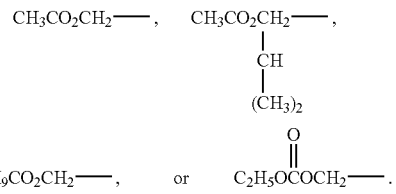

Other examples of suitable prodrug esters include

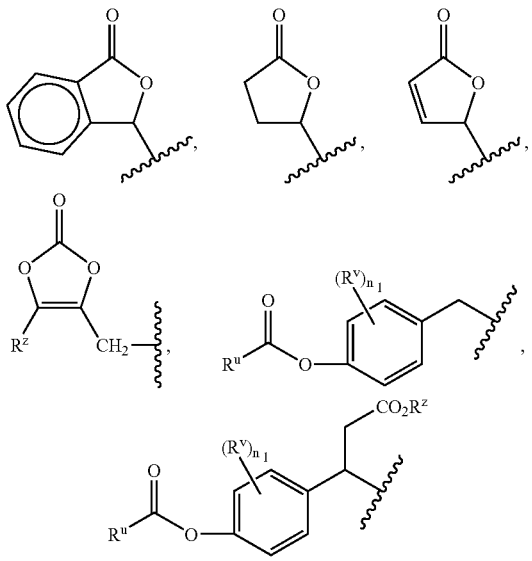

wherein $R^z$ can be H, alkyl (such as methyl or t-butyl), arylalkyl (such as benzyl) or aryl (such as phenyl); $R^v$ is H, alkyl, halogen or alkoxy, $R^u$ is alkyl, aryl, arylalkyl or alkoxyl, and $n_1$ is 0, 1 or 2.

For further examples of prodrug derivatives, see:
a) *Design of Prodrugs,* edited by H. Bundgaard, (Elsevier, 1985) and *Methods in Enzymology,* Vol. 112, pp. 309-396, edited by K. Widder, et al. (Academic Press, 1985);
b) *A Textbook of Drug Design and Development,* edited by Krosgaard-Larsen and H. Bundgaard, Chapter 5, "Design and Application of Prodrugs," by H. Bundgaard, pp. 113-191 (1991); and
c) H. Bundgaard, *Advanced Drug Delivery Reviews,* 8, 1-38 (1992).

The term "tautomer" refers to compounds of the formula (I) and salts thereof that may exist in their tautomeric form, in which hydrogen atoms are transposed to other parts of the molecules and the chemical bonds between the atoms of the molecules are consequently rearranged. It should be understood that the all tautomeric forms, insofar as they may exist, are included within the invention.

The terms pharmaceutically acceptable "salt" and "salts" refer to basic salts formed with inorganic and organic bases. Such salts include ammonium salts; alkali metal salts, such as lithium, sodium and potassium salts (which are preferred); alkaline earth metal salts, such as calcium and magnesium salts; salts with organic bases, such as amine like salts (e.g., dicyclohexylamine salt, benzathine, N-methyl-D-glucamine, and hydrabamine salts); and salts with amino acids like arginine, lysine and the like; and zwitterions, the so-called "inner salts". Nontoxic, pharmaceutically acceptable salts are preferred, although other salts are also useful, e.g., in isolating or purifying the product.

The term pharmaceutically acceptable "salt" and "salts" also includes acid addition salts. These are formed, for example, with strong inorganic acids, such as mineral acids, for example sulfuric acid, phosphoric acid or a hydrohalic acid such as HCl or HBr, with strong organic carboxylic acids, such as alkanecarboxylic acids of 1 to 4 carbon atoms which are unsubstituted or substituted, for example, by halogen, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as ($C_1$-$C_4$) alkyl or arylsulfonic acids which are unsubstituted or substituted, for example by halogen, for example methanesulfonic acid or p-toluenesulfonic acid.

Additionally, the instant inventive compounds may have trans and cis isomers and may contain one or more chiral centers, therefore existing in stereoisomeric (enantiomeric and diastereomeric) forms. The invention includes all such isomers, as well as mixtures of cis and trans isomers, mixtures of diastereomers and racemic mixtures of enantiomers (optical isomers). When no specific mention is made of the configuration (cis, trans or R or S) of a compound (or of an asymmetric carbon), then any one of the isomers or a mixture of more than one isomer is intended. The processes for preparation can use racemates or stereoisomers as starting materials. When stereoisomeric products are prepared, they can be separated by conventional methods for example, chromatographic or fractional crystallization. The inventive compounds may be in the free or solvate (e.g. hydrate) form.

Combinations

Where desired, the compounds of structure I may be used in combination with one or more other types of therapeutic agents such as immunosuppressants, anticancer agents, antiviral agents, anti-inflammatory agents, anti-fungal agents, antibiotics, anti-vascular hyperproliferation agents, anti-depressive agents, hypolipidemic agents or lipid-lowering agents or lipid modulating agents, antidiabetic agents, anti-obesity agents, antihypertensive agents, platelet aggregation inhibitors, and/or anti-osteoporosis agents, which may be administered orally in the same dosage form, in a separate oral dosage form or by injection.

The immunosuppressants which may be optionally employed in combination with compounds of formula I of the invention include cyclosporins, for example cyclosporin A, mycophenolate, interferon-beta, deoxyspergolin, FK-506 or Ant.-IL-2.

The anti-cancer agents which may be optionally employed in combination with compounds of formula I of the invention include azathiprine, 5-fluorouracil, cyclophosphamide, cisplatin, methotrexate, thiotepa, carboplatin, and the like.

The anti-viral agents which may be optionally employed in combination with compounds of formula I of the invention include abacavir, aciclovir, ganciclovir, zidanocin, vidarabine, and the like.

The anti-inflammatory agents which may be optionally employed in combination with compounds of formula I of the invention include non-steroidal anti-inflammatory drugs (NSAIDs) such as ibuprofen, cox-2 inhibitors such as celecoxib, rofecoxib, aspirin, naproxen, ketoprofen, diclofenac sodium, indomethacin, piroxicam, steroids such as prednisone, dexamethasone, hydrocortisone, triamcinolone diacetate, gold compounds, such as gold sodium thiomalate, TNF-α inhibitors such as tenidap, anti-TNF antibodies or soluble TNF receptor, and rapamycin (sirolimus or Rapamune) or derivatives thereof, infliximab (Remicade® Centocor, Inc.). CTLA-4Ig, LEA29Y, antibodies such as anti-ICAM-3, anti-IL-2 receptor (Anti-Tac), anti-CD45RB, anti-CD2, anti-CD3 (OKT-3), anti-CD4, anti-CD80, anti-CD86, monoclonal antibody OKT3, agents blocking the interaction between CD40 and CD154 (a.k.a. "gp39"), such as antibodies specific for CD40 and/or CD154, fusion proteins such as etanercept, fusion proteins constructed from CD40 and/or CD154gp39 (e.g. CD40Ig and CD8gp39), inhibitors, such as nuclear translocation inhibitors, of NF-kappa B function, such as deoxyspergualin (DSG).

The anti-fungal agents which may be optionally employed in combination with compounds of formula I of the invention include fluconazole, miconazole, amphotericin B, and the like.

The antibiotics which may be optionally employed in combination with compounds of formula I of the invention include penicillin, tetracycline, amoxicillin, ampicillin, erythromycin, doxycycline, vancomycin, minocycline, clindamycin or cefalexin.

The anti-vascular hyperproliferation agents which may be optionally employed with compounds of formula I of the invention include methotrexate, leflunomide, FK506 (tacrolimus, Prograf), The hypolipidemic agent or lipid-lowering agent or lipid modulating agents which may be optionally employed in combination with the compounds of formula I of the invention may include 1,2,3 or more MTP inhibitors, HMG CoA reductase inhibitors, squalene synthetase inhibitors, fibric acid derivatives, ACAT inhibitors, lipoxygenase inhibitors, cholesterol absorption inhibitors, ileal Na+/bile acid cotransporter inhibitors, upregulators of LDL receptor activity, bile acid sequestrants, and/or nicotinic acid and derivatives thereof.

MTP inhibitors employed herein include MTP inhibitors disclosed in U.S. Pat. Nos. 5,595,872, 5,739,135, 5,712,279, 5,760,246, 5,827,875, 5,885,983 and U.S. application Ser. No. 09/175,180 filed Oct. 20, 1998, now U.S. Pat. No. 5,962,440. Preferred are each of the preferred MTP inhibitors disclosed in each of the above patents and applications.

All of the above U.S. Patents and applications are incorporated herein by reference.

Most preferred MTP inhibitors to be employed in accordance with the present invention include preferred MTP inhibitors as set out in U.S. Pat. Nos. 5,739,135 and 5,712,279, and 5,760,246.

The most preferred MTP inhibitor is 9-[4-[4-[[2-(2,2,2-trifluoroethoxy)benzoyl]amino]-1-piperidinyl]butyl]-N-(2,2,2-trifluoroethyl)-9H-fluorene-9-carboxamide

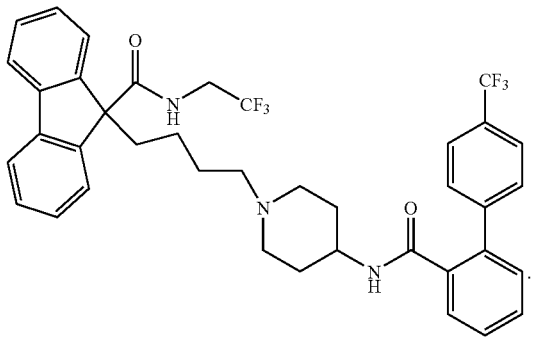

The hypolipidemic agent may be an HMG CoA reductase inhibitor which includes, but is not limited to, mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772, cerivastatin disclosed in U.S. Pat. Nos. 5,006,530 and 5,177,080, atorvastatin disclosed in U.S. Pat. Nos. 4,681,893, 5,273,995, 5,385,929 and 5,686,104, itavastatin (Nissan/Sankyo's nisvastatin (NK-104)) disclosed in U.S. Pat. No. 5,011,930, Shionogi-Astra/Zeneca visastatin (ZD-4522) disclosed in U.S. Pat. No. 5,260,440, and related statin compounds disclosed in U.S. Pat. No. 5,753,675, pyrazole analogs of mevalonolactone derivatives as disclosed in U.S. Pat. No. 4,613,610, indene analogs of mevalonolactone derivatives as disclosed in PCT application WO 86/03488, 6-[2-(substituted-pyrrol-1-yl)-alkyl)pyran-2-ones and derivatives thereof as disclosed in U.S. Pat. No. 4,647,576, Searle's SC-45355 (a 3-substituted pentanedioic acid derivative) dichloroacetate, imidazole analogs of mevalonolactone as disclosed in PCT application WO 86/07054, 3-carboxy-2-hydroxy-propane-phosphonic acid derivatives as disclosed in French Patent No. 2,596,393, 2,3-disubstituted pyrrole, furan and thiophene derivatives as disclosed in European Patent Application No. 0221025, naphthyl analogs of mevalonolactone as disclosed in U.S. Pat. No. 4,686,237, octahydronaphthalenes such as disclosed in U.S. Pat. No. 4,499,289, keto analogs of mevinolin (lovastatin) as disclosed in European Patent Application No. 0,142,146 A2, and quinoline and pyridine derivatives disclosed in U.S. Pat. Nos. 5,506,219 and 5,691,322.

In addition, phosphinic acid compounds useful in inhibiting HMG CoA reductase suitable for use herein are disclosed in GB 2205837.

The squalene synthetase inhibitors suitable for use herein include, but are not limited to, α-phosphono-sulfonates disclosed in U.S. Pat. No. 5,712,396, those disclosed by Biller et al, J. Med. Chem., 1988, Vol. 31, No. 10, pp 1869-1871, including isoprenoid(phosphinyl-methyl)phosphonates as well as other known squalene synthetase inhibitors, for example, as disclosed in U.S. Pat. Nos. 4,871,721 and 4,924,024 and in Biller, S. A., Neuenschwander, K., Ponpipom, M. M., and Poulter, C. D., Current Pharmaceutical Design, 2, 1-40 (1996).

In addition, other squalene synthetase inhibitors suitable for use herein include the terpenoid pyrophosphates disclosed by P. Ortiz de Montellano et al, J. Med. Chem., 1977, 20, 243-249, the farnesyl diphosphate analog A and presqualene pyrophosphate (PSQ-PP) analogs as disclosed by Corey and Volante, J. Am. Chem. Soc., 1976, 98, 1291-1293, phosphinylphosphonates reported by McClard, R. W. et al, J.A.C.S., 1987, 109, 5544 and cyclopropanes reported by Capson, T. L., PhD dissertation, June, 1987, Dept. Med. Chem. U of Utah, Abstract, Table of Contents, pp 16, 17, 40-43, 48-51, Summary.

Other hypolipidemic agents suitable for use herein include, but are not limited to, fibric acid derivatives, such as fenofibrate, gemfibrozil, clofibrate, bezafibrate, ciprofibrate, clinofibrate and the like, probucol, and related compounds as disclosed in U.S. Pat. No. 3,674,836, probucol and gemfibrozil being preferred, bile acid sequestrants such as cholestyramine, colestipol and DEAE-Sephadex (Secholex®, Policexide®) and cholestagel (Sankyo/Geltex), as well as lipostabil (Rhone-Poulenc), Eisai E-5050 (an N-substituted ethanolamine derivative), imanixil (HOE-402), tetrahydrolipstatin (THL), istigmastanylphos-phorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid (niacin), acipimox, acifran, neomycin, p-aminosalicylic acid, aspirin, poly(diallylmethylamine) derivatives such as disclosed in U.S. Pat. No. 4,759,923, quaternary amine poly(diallyldimethylammonium chloride) and ionenes such as disclosed in U.S. Pat. No. 4,027,009, and other known serum cholesterol lowering agents.

The hypolipidemic agent may be an ACAT inhibitor such as disclosed in, Drugs of the Future 24, 9-15 (1999), (Avasimibe); "The ACAT inhibitor, Cl-1011 is effective in the prevention and regression of aortic fatty streak area in hamsters", Nicolosi et al, Atherosclerosis (Shannon, Irel). (1998), 137(1), 77-85; "The pharmacological profile of FCE 27677: a novel ACAT inhibitor with potent hypolipidemic activity mediated by selective suppression of the hepatic secretion of ApoB100-containing lipoprotein", Ghiselli, Giancarlo, Cardiovasc. Drug Rev. (1998), 16(1), 16-30; "RP 73163: a bioavailable alkylsulfinyl-diphenylimidazole ACAT inhibitor", Smith, C., et al, Bioorg. Med. Chem. Lett. (1996), 6(1), 47-50; "ACAT inhibitors: physiologic mechanisms for hypolipidemic and anti-atherosclerotic activities in experimental animals", Krause et al, Editor(s): Ruffolo, Robert R., Jr.; Hollinger, Mannfred A., Inflammation: Mediators Pathways (1995), 173-98, Publisher: CRC, Boca Raton, Fla.; "ACAT inhibitors: potential anti-atherosclerotic agents", Sliskovic et al, Curr. Med. Chem. (1994), 1(3), 204-25; "Inhibitors of acyl-CoA:cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)methyl]ureas with enhanced hypocholesterolemic activity", Stout et al, Chemtracts: Org. Chem. (1995), 8(6), 359-62, or TS-962 (Taisho Pharmaceutical Co. Ltd).

The hypolipidemic agent may be an upregulator of LD2 receptor activity such as MD-700 (Taisho Pharmaceutical Co. Ltd) and LY295427 (Eli Lilly).

The hypolipidemic agent may be a cholesterol absorption inhibitor preferably Schering-Plough's ezetimibe (SCH58235) and SCH48461 as well as those disclosed in Atherosclerosis 115, 45-63 (1995) and J. Med. Chem. 41, 973 (1998).

The hypolipidemic agent may be an ileal Na$^+$/bile acid cotransporter inhibitor such as disclosed in Drugs of the Future, 24, 425-430 (1999).

The lipid-modulating agent may be a cholesteryl ester transfer protein (CETP) inhibitor such as Pfizer's CP 529, 414 (WO/0038722 and EP 818448) and Pharmacia's SC-744 and SC-795.

The ATP citrate lyase inhibitor which may be employed in the combination of the invention may include, for example, those disclosed in U.S. Pat. No. 5,447,954.

Preferred hypolipidemic agents are pravastatin, lovastatin, simvastatin, atorvastatin, fluvastatin, cerivastatin, itavastatin and visastatin and ZD-4522.

The above-mentioned U.S. Pat. Nos. are incorporated herein by reference. The amounts and dosages employed will be as indicated in the Physician's Desk Reference and/or in the patents set out above.

The compounds of formula I of the invention will be employed in a weight ratio to the hypolipidemic agent (were present), within the range from about 500:1 to about 1:500, preferably from about 100:1 to about 1:100.

The dose administered must be carefully adjusted according to age, weight and condition of the patient, as well as the route of administration, dosage form and regimen and the desired result.

The dosages and formulations for the hypolipidemic agent will be as disclosed in the various patents and applications discussed above.

The dosages and formulations for the other hypolipidemic agent to be employed, where applicable, will be as set out in the latest edition of the Physicians' Desk Reference.

For oral administration, a satisfactory result may be obtained employing the MTP inhibitor in an amount within the range of from about 0.01 mg to about 500 mg and preferably from about 0.1 mg to about 100 mg, one to four times daily.

A preferred oral dosage form, such as tablets or capsules, will contain the MTP inhibitor in an amount of from about 1 to about 500 mg, preferably from about 2 to about 400 mg, and more preferably from about 5 to about 250 mg, one to four times daily.

For oral administration, a satisfactory result may be obtained employing an HMG CoA reductase inhibitor, for example, pravastatin, lovastatin, simvastatin, atorvastatin, fluvastatin or cerivastatin in dosages employed as indicated in the Physician's Desk Reference, such as in an amount within the range of from about 1 to 2000 mg, and preferably from about 4 to about 200 mg.

The squalene synthetase inhibitor may be employed in dosages in an amount within the range of from about 10 mg to about 2000 mg and preferably from about 25 mg to about 200 mg.

A preferred oral dosage form, such as tablets or capsules, will contain the HMG CoA reductase inhibitor in an amount from about 0.1 to about 100 mg, preferably from about 0.5 to about 80 mg, and more preferably from about 1 to about 40 mg.

A preferred oral dosage form, such as tablets or capsules will contain the squalene synthetase inhibitor in an amount of from about 10 to about 500 mg, preferably from about 25 to about 200 mg.

The hypolipidemic agent may also be a lipoxygenase inhibitor including a 15-lipoxygenase (15-LO) inhibitor such as benzimidazole derivatives as disclosed in WO 97/12615, 15-LO inhibitors as disclosed in WO 97/12613, isothiazolones as disclosed in WO 96/38144, and 15-LO inhibitors as disclosed by Sendobry et al "Attenuation of diet-induced atherosclerosis in rabbits with a highly selective 15-lipoxygenase inhibitor lacking significant antioxidant properties", Brit. J. Pharmacology (1997) 120, 1199-1206, and Cornicelli et al, "15-Lipoxygenase and its Inhibition: A Novel Therapeutic Target for Vascular Disease", Current Pharmaceutical Design, 1999, 5, 11-20.

The compounds of formula I and the hypolipidemic agent may be employed together in the same oral dosage form or in separate oral dosage forms taken at the same time.

The compositions described above may be administered in the dosage forms as described above in single or divided doses of one to four times daily. It may be advisable to start a patient on a low dose combination and work up gradually to a high dose combination.

The preferred hypolipidemic agent is pravastatin, simvastatin, lovastatin, atorvastatin, fluvastatin or cerivastatin as well as niacin and/or cholestagel.

The other antidiabetic agent which may be optionally employed in combination with the compound of formula I may be 1,2,3 or more antidiabetic agents or antihyperglycemic agents including insulin secretagogues or insulin sensitizers, or other antidiabetic agents preferably having a mechanism of action different from the compounds of formula I of the invention, which may include biguanides, sulfonyl ureas, glucosidase inhibitors, PPAR γ agonists, such as thiazolidinediones, aP2 inhibitors, dipeptidyl peptidase IV (DP4) inhibitors, SGLT2 inhibitors, and/or meglitinides, as well as insulin, and/or glucagon-like peptide-1 (GLP-1).

The other antidiabetic agent may be an oral antihyperglycemic agent preferably a biguanide such as metformin or phenformin or salts thereof, preferably metformin HCl.

Where the antidiabetic agent is a biguanide, the compounds of structure I will be employed in a weight ratio to biguanide within the range from about 0.001:1 to about 10:1, preferably from about 0.01:1 to about 5:1.

The other antidiabetic agent may also preferably be a sulfonyl urea such as glyburide (also known as glibenclamide), glimepiride (disclosed in U.S. Pat. No. 4,379,785), glipizide, gliclazide or chlorpropamide, other known sulfonylureas or other antihyperglycemic agents which act on the ATP-dependent channel of the □-cells, with glyburide and glipizide being preferred, which may be administered in the same or in separate oral dosage forms.

The compounds of structure I will be employed in a weight ratio to the sulfonyl urea in the range from about 0.01:1 to about 100:1, preferably from about 0.02:1 to about 5:1.

The oral antidiabetic agent may also be a glucosidase inhibitor such as acarbose (disclosed in U.S. Pat. No. 4,904,769) or miglitol (disclosed in U.S. Pat. No. 4,639,436), which may be administered in the same or in a separate oral dosage forms.

The compounds of structure I will be employed in a weight ratio to the glucosidase inhibitor within the range from about 0.01:1 to about 100:1, preferably from about 0.05:1 to about 10:1.

The compounds of structure I may be employed in combination with a PPAR γ agonist such as a thiazolidinedione oral anti-diabetic agent or other insulin sensitizers (which has an insulin sensitivity effect in NIDDM patients) such as troglitazone (Warner-Lambert's Rezulin®, disclosed in U.S. Pat. No. 4,572,912), rosiglitazone (SKB), pioglitazone (Takeda), Mitsubishi's MCC-555 (disclosed in U.S. Pat. No. 5,594,016), Glaxo-Welcome's GL-262570, englitazone (CP-68722, Pfizer) or darglitazone (CP-86325, Pfizer, isaglitazone (MIT/J&J), JTT-501 (JPNT/P&U), L-895645 (Merck), R-119702 (Sankyo/WL), NN-2344 (Dr. Reddy/NN), or YM-440 (Yamanouchi), preferably rosiglitazone and pioglitazone.

The compounds of structure I will be employed in a weight ratio to the thiazolidinedione in an amount within the range from about 0.01:1 to about 100:1, preferably from about 0.05 to about 10:1.

The sulfonyl urea and thiazolidinedione in amounts of less than about 150 mg oral antidiabetic agent may be incorporated in a single tablet with the compounds of structure I.

The compounds of structure I may also be employed in combination with a antihyperglycemic agent such as insulin or with glucagon-like peptide-1 (GLP-1) such as GLP-1(1-36) amide, GLP-1(7-36) amide, GLP-1(7-37) (as disclosed in U.S. Pat. No. 5,614,492 to Habener, the disclosure of which is incorporated herein by reference), as well as AC2993 (Amylin) and LY-315902 (Lilly), which may be administered via injection, intranasal, inhalation or by transdermal or buccal devices.

Where present, metformin, the sulfonyl ureas, such as glyburide, glimepiride, glipyride, glipizide, chlorpropamide and gliclazide and the glucosidase inhibitors acarbose or miglitol or insulin (injectable, pulmonary, buccal, or oral) may be employed in formulations as described above and in amounts and dosing as indicated in the Physician's Desk Reference (PDR).

Where present, metformin or salt thereof may be employed in amounts within the range from about 500 to about 2000 mg per day which may be administered in single or divided doses one to four times daily.

Where present, the thiazolidinedione anti-diabetic agent may be employed in amounts within the range from about 0.01 to about 2000 mg/day which may be administered in single or divided doses one to four times per day.

Where present insulin may be employed in formulations, amounts and dosing as indicated by the Physician's Desk Reference.

Where present GLP-1 peptides may be administered in oral buccal formulations, by nasal administration or parenterally as described in U.S. Pat. No. 5,346,701 (TheraTech), U.S. Pat. Nos. 5,614,492 and 5,631,224 which are incorporated herein by reference.

The other antidiabetic agent may also be a PPAR α/γ dual agonist such as AR-HO39242 (Astra/Zeneca), GW-409544 (Glaxo-Wellcome), KRP297 (Kyorin Merck) as well as those disclosed by Murakami et al, "A Novel Insulin Sensitizer Acts As a Coligand for Peroxisome Proliferation-Activated Receptor Alpha (PPAR alpha) and PPAR gamma. Effect on PPAR alpha Activation on Abnormal Lipid Metabolism in Liver of Zucker Fatty Rats", Diabetes 47, 1841-1847 (1998).

The antidiabetic agent may be an SGLT2 inhibitor such as disclosed in U.S. application Ser. No. 09/679,027, filed Oct. 4, 2000 (attorney file LA49 NP), employing dosages as set out therein. Preferred are the compounds designated as preferred in the above application.

The antidiabetic agent may be an aP2 inhibitor such as disclosed in U.S. application Ser. No. 09/391,053, filed Sep. 7, 1999, and in U.S. application Ser. No. 09/519,079, filed Mar. 6, 2000 (attorney file LA27 NP), employing dosages as set out herein. Preferred are the compounds designated as preferred in the above application.

The antidiabetic agent may be a DP4 inhibitor such as disclosed in U.S. application Ser. No. 09/788,173 filed Feb. 16, 2001 (attorney file LA50), WO99/38501, WO99/46272, WO99/67279 (PROBIODRUG), WO99/67278 (PROBIODRUG), WO99/61431 (PROBIODRUG), NVP-DPP728A (1-[[[2-[(5-cyanopyridin-2-yl)amino]ethyl]amino]acetyl]-2-cyano-(S)-pyrrolidine) (Novartis) (preferred) as disclosed by Hughes et al, Biochemistry, 38(36), 11597-11603, 1999, TSL-225 (tryptophyl-1,2,3,4-tetrahydro-isoquinoline-3-carboxylic acid (disclosed by Yamada et al, Bioorg. & Med. Chem. Lett. 8 (1998) 1537-1540, 2-cyanopyrrolidides and 4-cyanopyrrolidides as disclosed by Ashworth et al, Bioorg. & Med. Chem. Lett., Vol. 6, No. 22, pp 1163-1166 and 2745-2748 (1996) employing dosages as set out in the above references.

The meglitinide which may optionally be employed in combination with the compound of formula I of the invention may be repaglinide, nateglinide (Novartis) or KAD1229 (PF/Kissei), with repaglinide being preferred.

The compound of formula I will be employed in a weight ratio to the meglitinide, PPAR γ agonist, PPAR α/γ dual agonist, aP2 inhibitor, DP4 inhibitor or SGLT2 inhibitor within the range from about 0.01:1 to about 100:1, preferably from about 0.05 to about 10:1.

The other type of therapeutic agent which may be optionally employed with a compound of formula I may be 1, 2, 3 or more of an anti-obesity agent including a beta 3 adrenergic agonist, a lipase inhibitor, a serotonin (and dopamine) reuptake inhibitor, an aP2 inhibitor, a thyroid receptor agonist and/or an anorectic agent.

The beta 3 adrenergic agonist which may be optionally employed in combination with a compound of formula I may be AJ9677 (Takeda/Dainippon), L750355 (Merck), or CP331648 (Pfizer) or other known beta 3 agonists as disclosed in U.S. Pat. Nos. 5,541,204, 5,770,615, 5,491,134, 5,776,983 and 5,488,064, with AJ9677, L750,355 and CP331648 being preferred.

The lipase inhibitor which may be optionally employed in combination with a compound of formula I may be or list at or ATL-962 (Alizyme), with orlistat being preferred.

The serotonin (and dopoamine) reuptake inhibitor which may be optionally employed in combination with a compound of formula I may be sibutramine, topiramate (Johnson & Johnson) or axokine (Regeneron), with sibutramine and topiramate being preferred.

The thyroid receptor agonist which may be optionally employed in combination with a compound of formula I may be a thyroid receptor ligand as disclosed in WO97/21993 (U. Cal SF), WO99/00353 (KaroBio), WO2000039077 (KaroBio, particularly in priority document GB98/28442), and U.S. Provisional Application 60/183,223 filed Feb. 17, 2000, with compounds of the KaroBio applications and the above U.S. provisional application being preferred.

The anorectic agent which may be optionally employed in combination with a compound of formula I may be dexamphetamine, phentermine, phenylpropanolamine or mazindol, with dexamphetamine being preferred.

The various anti-obesity agents described above may be employed in the same dosage form with the compound of formula I or in different dosage forms, in dosages and regimens as generally known in the art or in the PDR.

The antihypertensive agents which may be employed in combination with the compound of formula I of the invention include ACE inhibitors, angiotensin II receptor antagonists, NEP/ACE inhibitors, as well as calcium channel blockers, β-adrenergic blockers and other types of antihypertensive agents including diuretics.

The angiotensin converting enzyme inhibitor which may be employed herein includes those containing a mercapto (—S—) moiety such as substituted proline derivatives, such as any of those disclosed in U.S. Pat. No. 4,046,889 to Ondetti et al mentioned above, with captopril, that is, 1-[(2S)-3-mercapto-2-methylpropionyl]-L-proline, being preferred, and mercaptoacyl derivatives of substituted prolines such as any of those disclosed in U.S. Pat. No. 4,316,906 with zofenopril being preferred.

Other examples of mercapto containing ACE inhibitors that may be employed herein include rentiapril (fentiapril, Santen) disclosed in Clin. Exp. Pharmacol. Physiol. 10:131 (1983); as well as pivopril and YS980.

Other examples of angiotensin converting enzyme inhibitors which may be employed herein include any of those disclosed in U.S. Pat. No. 4,374,829 mentioned above, with N-(1-ethoxycarbonyl-3-phenylpropyl)-L-alanyl-L-proline, that is, enalapril, being preferred, any of the phosphonate substituted amino or imino acids or salts disclosed in U.S. Pat. No. 4,452,790 with (S)-1-[6-amino-2-[[hydroxy-(4-phenylbutyl)phosphinyl]oxy]-1-oxohexyl]-L-proline or (ceronapril) being preferred, phosphinylalkanoyl prolines disclosed in U.S. Pat. No. 4,168,267 mentioned above with fosinopril being preferred, any of the phosphinylalkanoyl substituted prolines disclosed in U.S. Pat. No. 4,337,201, and the phosphonamidates disclosed in U.S. Pat. No. 4,432,971 discussed above.

Other examples of ACE inhibitors that may be employed herein include Beecham's BRL 36,378 as disclosed in European Patent Application Nos. 80822 and 60668; Chugai's MC-838 disclosed in C.A. 102:72588v and Jap. J. Pharmacol. 40:373 (1986); Ciba-Geigy's CGS 14824 (3-([1-ethoxycarbonyl-3-phenyl-(1S)-propyl]amino)-2,3,4,5-tetrahydro-2-oxo-1-(3S)-benzazepine-1 acetic acid HCl) disclosed in U.K. Patent No. 2103614 and CGS 16,617 (3(S)-[[(1S)-5-amino-1-carboxypentyl]amino]-2,3,4,5-tetrahydro-2-oxo-1H-1-benzazepine-1-ethanoic acid) disclosed in U.S. Pat. No. 4,473,575; cetapril (alacepril, Dainippon) disclosed in Eur. Therap. Res. 39:671 (1986); 40:543 (1986); ramipril (Hoechsst) disclosed in Euro. Patent No. 79-022 and Curr. Ther. Res. 40:74 (1986); Ru 44570 (Hoechst) disclosed in Arzneimittelforschung 34:1254 (1985), cilazapril (Hoffman-LaRoche) disclosed in J. Cardiovasc. Pharmacol. 9:39 (1987); R 31-2201 (Hoffman-LaRoche) disclosed in FEBS Lett. 165:201 (1984); lisinopril (Merck), indalapril (delapril) disclosed in U.S. Pat. No. 4,385,051; indolapril (Schering) disclosed in J. Cardiovasc. Pharmacol. 5:643, 655 (1983), spirapril (Schering) disclosed in Acta. Pharmacol. Toxicol. 59 (Supp. 5):173 (1986); perindopril (Servier) disclosed in Eur. J. Clin. Pharmacol. 31:519 (1987); quinapril (Warner-Lambert) disclosed in U.S. Pat. No. 4,344,949 and CI925 (Warner-Lambert) ([3S-[2[R(*)R (*)]]3R(*)]-2-[2-[[1-(ethoxy-carbonyl)-3-phenylpropyl] amino]-1-oxopropyl]-1,2,3,4-tetrahydro-6,7-dimethoxy-3-isoquinolinecarboxylic acid HCl)disclosed in Pharmacologist 26:243, 266 (1984), WY-44221 (Wyeth) disclosed in J. Med. Chem. 26:394 (1983).

Preferred ACE inhibitors are captopril, fosinopril, enalapril, lisinopril, quinapril, benazepril, fentiapril, ramipril and moexipril.

NEP/ACE inhibitors may also be employed herein in that they possess neutral endopeptidase (NEP) inhibitory activity and angiotensin converting enzyme (ACE) inhibitory activity. Examples of NEP/ACE inhibitors suitable for use herein include those disclosed in U.S. Pat. Nos. 5,362,727, 5,366, 973, 5,225,401, 4,722,810, 5,223,516, 4,749,688, 5,552,397, 5,504,080, 5,612,359, 5,525,723, European Patent Application 0599,444, 0481,522, 0599,444, 0595,610, European Patent Application 0534363A2, 534,396 and 534,492, and European Patent Application 0629627A2.

Preferred are those NEP/ACE inhibitors and dosages thereof which are designated as preferred in the above patents/applications which U.S. Pat. Nos. are incorporated herein by reference; most preferred are omapatrilat, BMS 189,921 ([S-(R*,R*)]-hexahydro-6-[(2-mercapto-1-oxo-3-phenylpropyl)amino]-2,2-dimethyl-7-oxo-1H-azepine-1-acetic acid (gemopatrilat)) and CGS 30440.

The angiotensin II receptor antagonist (also referred to herein as angiotensin II antagonist or AII antagonist) suitable for use herein includes, but is not limited to, irbesartan, losartan, valsartan, candesartan, telmisartan, tasosartan or eprosartan, with irbesartan, losartan or valsartan being preferred.

A preferred oral dosage form, such as tablets or capsules, will contain the ACE inhibitor or AII antagonist in an amount within the range from abut 0.1 to about 500 mg, preferably from about 5 to about 200 mg and more preferably from about 10 to about 150 mg.

For parenteral administration, the ACE inhibitor, angiotensin II antagonist or NEP/ACE inhibitor will be employed in an amount within the range from about 0.005 mg/kg to about 10 mg/kg and preferably from about 0.01 mg/kg to about 1 mg/kg.

Where a drug is to be administered intravenously, it will be formulated in conventional vehicles, such as distilled water, saline, Ringer's solution or other conventional carriers.

It will be appreciated that preferred dosages of ACE inhibitor and AII antagonist as well as other antihypertensives disclosed herein will be as set out in the latest edition of the Physician's Desk Reference (PDR).

Other examples of preferred antihypertensive agents suitable for use herein include omapatrilat (Vanlev®) amlodipine besylate (Norvasc®), prazosin HCl (Minipress®), verapamil, nifedipine, nadolol, diltiazem, felodipine, nisoldipine, isradipine, nicardipine, atenolol, carvedilol, sotalol, terazosin, doxazosin, propranolol, and clonidine HCl (Catapres®).

Diuretics which may be employed in combination with compounds of formula I include hydrochlorothiazide, torasemide, furosemide, spironolactono, and indapamide.

Antiplatelet agents which may be employed in combination with compounds of formula I of the invention include aspirin, clopidogrel, ticlopidine, dipyridamole, abciximab, tirofiban, eptifibatide, anagrelide, and ifetroban, with clopidogrel and aspirin being preferred.

The antiplatelet drugs may be employed in amounts as indicated in the PDR. Ifetroban may be employed in amounts as set out in U.S. Pat. No. 5,100,889.

Antiosteoporosis agents suitable for use herein in combination with the compounds of formula I of the invention include parathyroid hormone or bisphosphonates, such as MK-217 (alendronate) (Fosamax®).

Dosages employed for the above drugs will be as set out in the Physician's Desk Reference.

Pharmaceutical Formulations

The pharmaceutical composition of the invention includes a pharmaceutically acceptable carrier, adjuvant or vehicle that may be administered to a subject, together with a compound of the present invention, and which does not destroy the pharmacological activity thereof. Pharmaceutically acceptable carriers, adjuvants and vehicles that may be used in the pharmaceutical compositions of the present invention include, but are not limited to, the following: ion exchangers, alumina, aluminum stearate, lecithin, self-emulsifying drug delivery systems ("SEDDS") such as d(-tocopherol polyethyleneglycol 1000 succinate), surfactants used in pharmaceutical dosage forms such as Tweens or other similar polymeric delivery matrices, serum proteins such as human serum albumin, buffer substances such as phosphates, glycine, sorbic acid, potassium sorbate, partial glyceride mixtures of saturated vegetable fatty acids, water, salts or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as $\alpha$-, $\beta$- and $\gamma$-cyclodextrin, or chemically modified derivatives such as hydroxyalkylcyclodextrins, including 2- and 3-hydroxypropyl-$\beta$-cyclodextrins, or other solubilized derivatives may also be used to enhance delivery of the modulators of the present invention.

The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of the invention may be administered by any suitable means, for example, orally, such as in the form of tablets, capsules, granules or powders; sublingually; buccally; parenterally, such as by subcutaneous, intravenous, intramuscular, or intrastemal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. The compounds of the invention may, for example, be administered in a form suitable for immediate release or extended release. Immediate release or extended release may be achieved by the use of suitable pharmaceutical compositions including the compounds of the invention, or, particularly in the case of extended release, by the use of devices such as subcutaneous implants or osmotic pumps. The compounds of the invention may also be administered liposomally.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The present compunds may also be delivered through the oral cavity by sublingual and/or buccal administration. Molded tablets, compressed tablets or freeze-dried tablets are exemplary forms which may be used. Exemplary compositions include those formulating the compound(s) of the invention with fast dissolving diluents such as mannitol, lactose, sucrose and/or cyclodextrins. Also included in such formulations may be high molecular weight excipients such as celluloses (Avicel) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid. The term "parenteral" as used herein includes subcutaneous, intracutaneous, intravenous, intramuscular, intraarticular, intraarterial, intrasynovial, intrastemal, intrathecal, intralesional and intracranial injection or infusion techniques.

Exemplary compositions for rectal administration include suppositories which may contain, for example, a suitable non-irritating excipient, such as cocoa butter, synthetic glyceride esters or polyethylene glycols, which are solid at ordinary temperatures, but liquify and/or dissolve in the rectal cavity to release the drug.

Exemplary compositions for topical administration include a topical carrier such as Plastibase (mineral oil gelled with polyethylene).

The effective amount of a compound of the present invention may be determined by one of ordinary skill in the art, and includes exemplary dosage amounts for an adult human of from about 0.1 to 500 mg/kg of body weight of active compound per day, or between 5 and 2000 mg per day which may be administered in a single dose or in the form of individual divided doses, such as from 1 to 5 times per day. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like.

A typical capsule for oral administration contains compounds of structure I (250 mg), lactose (75 mg) and magnesium stearate (15 mg). The mixture is passed through a 60 mesh sieve and packed into a No. 1 gelatin capsule.

A typical injectable preparation is produced by aseptically placing 250 mg of compounds of structure I into a vial, aseptically freeze-drying and sealing. For use, the contents of the vial are mixed with 2 mL of physiological saline, to produce an injectable preparation.

Compounds of the invention, including the compounds described in the examples hereof, have been tested in at least one of the assays described below and have glucocorticoid receptor (GR)/Dexamethasone (Dex) inhibition activity (>25% at 10 µM, preferably >95% at 10 µM) and/or AP-1 inhibition activity ($EC_{50}$ less than 15 µM).

Identical and/or similar assays are described in copending U.S. patent application Ser. No. 10/621,807, filed Jul. 18, 2002 which is incorporated herein in its entireity by reference.

GR (Dex) Binding Assay

In order to measure the binding of compounds to Site I on the glucocorticoid receptor a commercially available kit was used (Glucocorticoid receptor competitor assay kit, Panvera Co., Madison, Wis.). Briefly, a cell lysate containing recombinantly expressed human full-length glucocorticoid receptor was mixed with a fluorescently labeled glucocorticoid (4 nM FITC-dexamethasone) plus or minus test molecule. After one hour at room temperature, the fluorescence polarization (FP) of the samples were measured. The FP of a mixture of receptor, fluorescent probe (i.e. FITC-dexamethasone) and 1 mM dexamethasone represented background fluorescence or 100% inhibition, whereas, the FP of the mixture without dexamethasone was taken to be 100% binding. The percentage inhibition of test molecules were then compared to the sample with 1 mM dexamethasone and expressed as % relative binding activity with dexamethasone being 100% and no inhibition is 0%. Test molecules were analyzed in the concentration range from 0.1 nM to 40 µM.

Site I binding assays for any NHR (Nuclear Hormone Receptor) are conducted similarly to the above. An appropriate cell lysate or purified NHR is used as the source of the NHR. The fluorescent probe and unlabeled competitor are appropriate for the specific NHR, i.e. are ligands for the specific NHR.

Cellular Transrepressional Assay

To measure the ability of test molecules to inhibit AP-1 induced transcriptional activity we utilized an A549 cell which was stably transfected with a plasmid containing 7× AP-1 DNA binding sites (pAP-1-Luc plasmid, Stratagene Co. La Jolla, Calif.) followed by the gene for luciferase. Cells were activated with 10 ng/ml of phorbol myristic acid (PMA) plus or minus test molecules for 7 hours. After 7 hours a luciferase reagent was added to measure luciferase enzymatic activity in the cell. After a 10 minute incubation of luciferase reagent with cells, luminescence was measured in a TopCount luminescence counter. Repression of AP-1 activity was calculated as the percentage decrease in the signal induced by PMA alone. Test molecules were analyzed in the concentration range from 0.1 nM to 40 µM. $EC_{50}$s were determined by using standard curve fitting methods such as Excel fit (Microsoft Co.). An $EC_{50}$ is the test molecule concentration at which there is a 50% repression of the maximal inhibition of transcription, i.e. a 50% reduction of AP-1 activity.

Other reporters and cell lines also may be used in a cellular transrepressional assay. A similar assay is performed in which NF-κB activity is measured. A plasmid containing NF-κB DNA binding sites is used, such as pNF-κB-Luc, (Stratagene, LaJolla Calif.), and PMA or another stimulus, such as TNF-α or lipopolysaccharide, is used to activate the NF-κB pathway. NF-κB assays similar to that described in Yamamoto K., et al., *J Biol Chem* December 29;270(52): 31315-20 (1995) may be used.

The cellular transrepressional assays described above may be used to measure transrepression by any NHR. One of skill in the art will understand that assays may require the addition of components, such as a stimulus (eg. PMA, lipopolysaccharide, TNF-α, etc) which will induce transcription mediated by AP-1 or NF-κB. Additionally, AR mediated transrepression may be measured by the assay described in Palvimo J J, et al. *J Biol Chem* September 27;271(39):24151-6 (1996), and PR mediated transrepression may be measured by the assay described in Kalkhoven E., et al. *J Biol Chem* March 15;271(11):6217-24 (1996).

The following abbreviations are employed throughout the specification including the Preparations and Examples given below.

Ph=phenyl
Bn=benzyl
t-Bu=tertiary butyl
Me=methyl
Et=ethyl
TMS=trimethylsilyl
$TMSN_3$=trimethylsilyl azide
TBS=tert-butyldimethylsilyl
FMOC=fluorenylmethoxycarbonyl
Boc=tert-butoxycarbonyl
Cbz=carbobenzyloxy or carbobenzoxy or benzyloxycarbonyl
THF=tetrahydrofuran
$Et_2O$=diethyl ether
hex=hexanes
EtOAc=ethyl acetate
DMF=dimethyl formamide
MeOH=methanol
EtOH=ethanol
i-PrOH=isopropanol
DMSO=dimethyl sulfoxide
DME=1,2 dimethoxyethane
DCE=1,2 dichloroethane
HMPA=hexamethyl phosphoric triamide
HOAc or AcOH=acetic acid
TFA=trifluoroacetic acid
TFAA=trifluoroacetic anhydride
i-$Pr_2$NEt=diisopropylethylamine
$Et_3N$=triethylamine
NMM=N-methyl morpholine
DMAP=4-dimethylaminopyridine
$NaBH_4$=sodium borohydride
$NaBH(OAc)_3$=sodium triacetoxyborohydride
DIBALH=diisobutyl aluminum hydride
LAH or $LiAlH_4$=lithium aluminum hydride
n-BuLi=n-butyllithium
LDA=lithium diisopropylamide
Pd/C=palladium on carbon
$PtO_2$=platinum oxide KOH=potassium hydroxide
NaOH=sodium hydroxide
LiOH=lithium hydroxide
$K_2CO_3$=potassium carbonate
$NaHCO_3$=sodium bicarbonate
DBU=1,8-diazabicyclo[5.4.0]undec-7-ene
EDC (or EDC.HCl) or EDCI (or EDCI.HCl) or EDAC=3-ethyl-3'-(dimethylamino)propyl-carbodiimide hydrochloride (or 1-(3-dimethylaminopropyl)-3-ethylcarbodiimide hydrochloride)
HOBT or $HOBT.H_2O$=1-hydroxybenzotriazole hydrate
HOAT=1-Hydroxy-7-azabenzotriazole
BOP reagent=benzotriazol-1-yloxy-tris(dimethylamino)phosphonium hexafluorophosphate
$NaN(TMS)_2$=sodium hexamethyldisilazide or sodium bis(trimethylsilyl)amide
$Ph_3P$=triphenylphosphine
$Pd(OAc)_2$=Palladium acetate
$(Ph_3P)_4Pd^\circ$=tetrakis triphenylphosphine palladium
DEAD=diethyl azodicarboxylate
DIAD=diisopropyl azodicarboxylate
Cbz-Cl=benzyl chloroformate
CAN=ceric ammonium nitrate
SAX=Strong Anion Exchanger
SCX=Strong Cation Exchanger
Ar=argon
$N_2$=nitrogen
min=minute(s)
h or hr=hour(s)
L=liter
mL=milliliter
µL=microliter
g=gram(s)
mg=milligram(s)
mol=moles
mmol=millimole(s)
meq=milliequivalent
RT=room temperature
sat or sat'd=saturated
aq.=aqueous
TLC=thin layer chromatography
HPLC=high performance liquid chromatography
LC/MS=high performance liquid chromatography/mass spectrometry
MS or Mass Spec=mass spectrometry
NMR=nuclear magnetic resonance
NMR spectral data: s=singlet; d=doublet; m=multiplet; br=broad; t=triplet mp=melting point Preparations The preparations set out below are for the synthesis of reagents that were not obtained from commercial sources and were employed for the preparation of compounds of Formula I of the invention. All chemical structures in the tables and schemes are racemic unless specified otherwise.

The preparation of Cores A-I can be made via methods disclosed in patent application U.S. Ser. No. 10/621,909 filed Jul. 17, 2003, the entirety of which is included herein by reference.

Preparation of Carboxylic Acid Fluorides:

To a solution of 9-cyano-9,10-dihydro-11-methyl-9,10-ethanoanthracene-11-carboxylic acid (hereafter called Core A) (5.26 g, 18.2 mmol) and pyridine (2.2 mL, 27.0 mmol) in 10 mL of DCM was added a solution of cyanuric fluoride (2.14 g, 27.0 mmol) dropwise. After stirring 30 min, the reaction was diluted with 1N HCl, and extracted 2×DCM. The DCM extracts were dried over $MgSO_4$. The solution was filtered, concentrated by rotary evaporator to give 4.8 g (91%) of 9-cyano-9,10-dihydro-11-methyl-9,10-ethano-anthracene-11-carboxylic acid fluoride, Core B. MS found: $(M+H)^+$=292.

(a) To a solution of 9-nitro-9,10-dihydro-11-methyl-9,10-ethanoanthracene-11-carboxylic acid (hereafter called Core C) (500 mg, 1.6 mmol) and pyridine (0.25 mL, 3.0 mmol) in 10 mL of DCM was added a solution of cyanuric fluoride (400 mg, 3.0 mmol) dropwise. After stirring 30 min, the reaction was diluted with 1N HCl, and extracted 2×DCM. The DCM extracts were dried over $MgSO_4$. The solution was filtered, concentrated by rotary evaporator to give 482 mg (98%) of 9-nitro-9,10-dihydro-11-methyl-9,10-ethanoanthracene-11-carboxylic acid fluoride Core D. MS found: (M+H)$^+$=312.

General Coupling Method A:

To a solution of either Core B or Core D (0.12 mmol) in DMF or acetonitrile was added the 2-aminothiazole or 2-aminoimidazole compound (0.12-0.24 mmol) and the reaction was warmed in an 80 C oil bath for 4-16 hr. The reaction was diluted with water, acetonitrile, and some TFA and purified by HPLC to give the desired coupled product.

General Coupling Method B:

To a solution of either Core A or Core C (0.20 mmol) in either DMF or acetonitrile was added 1-hydroxybenzotriazole (28 mg, 0.20 mmol), triethylamine (21 mg, 0.40 mmol), and 1-[3-(dimethylamino)propyl]-3-ethylcarbodiimide hydrochloride (40 mg, 0.20 mmol). After stirring 10 min, the 2-aminothiazole or 2-aminoimidazole compound (0.20-0.40 mmol) was added and the reaction was warmed in an 80 C oil bath for 16 hr. The reaction was diluted with water, acetonitrile, and some TFA and purified by HPLC to give the desired coupled product.

The following Examples illustrate embodiments of the inventive compounds and starting materials, and are not intended to limit the scope of the claims.

EXAMPLES

Example 1

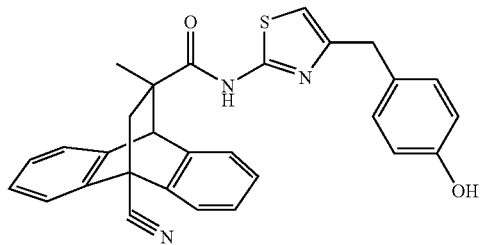

(a) To a solution of commercially available (4-bromophenoxy)-tert-butyldimethylsilane (21.7 g, 76 mmol) in 150 mL of dry THF was added sec-BuLi (76 mmol, 58 mL of 1.3 M in cyclohexane) over 10 min under N$_2$. After 1 hr, a suspension of CuCN in 100 mL dry THF was cooled to −78 C and added to the anion via cannula. The resulting suspension was warmed to 0 C, cooled back to −78 C, and treated with epichlorohydrin all at once. The reaction was stirred at −78 C for 30 min, warmed to −40 C for 1.5 hr, and was then warmed in an ice bath until the internal temperature was at 0 C for 15 min. The reaction was quenched with sat NH$_4$Cl, extracted 2×Et$_2$O, and the ethereal extracts were dried over MgSO$_4$. The solution was filtered, concentrated by rotary evaporator, and chromatographed on SiO$_2$ using 25% EtOAc in hexanes to give 8.35 g (75%) of a colorless oil 1a. $^1$H-NMR (400 MHz, CDCl$_3$): δ 7.08 (d, 2H), 6.79 (d, 2H), 4.0 (m, 1H), 3.59 (dd, 1H), 3.49 (dd, 1H), 2.83(d, 2H), 2.19 (br s, 1H), 0.98 (s, 9H), 0.19 (s, 6H).

(b) To a solution of 1a (8.14 g, 27.1 mmol) in 400 mL of DCM cooled to 0 C was added Dess Martin periodinane (11.49 g, 27.1 mmol) all at once. The reaction was allowed to warm to rt and was complete by TLC monitoring after 4 hr. The reaction was concentrated by rotary evaporator and the crude residue was purified on SiO$_2$ using DCM to give 7.37 g (91%) of pure chloromethylketone 1b as a yellow oil. This intermediate was taken up in 150 mL of EtOH and treated with a solution of thiourea (1.95 g, 24.7 mmol) in 50 mL EtOH. The reaction was concentrated in vacuo and a solid formed on standing to give pure 1c. $^1$H-NMR (400 MHz, CDCl$_3$): δ 9.0 (br s, 2H), 7.09 (d, 2H), 6.78 (d, 2H), 5.84 (s, 1H), 3.78 (s, 2H), 0.97 (s, 9H), 0.19 (s, 6H).

(c) To a solution of 1c (1.0 g, 3.11 mmol) in 15 mL warm THF was added tetrabutylammonium fluoride (4.05 mmol, 4.05 mL of 1 M solution in THF) at rt. The reaction was complete after 4 hr and the solvent removed by rotary evaporation. The product was extracted from sat NaHCO$_3$ with EtOAc×3. The organic layers were filtered and concentrated in vacuo to give 660 mg (100%) of an orange solid 1d. MS found: (M+H)$^+$=207.

(d) To a solution of Core B (2.5 g, 8.59 mmol) in 100 mL acetonitrile was added 1d (2.75 g, 8.59 mmol) and triethylamine (1.74 g, 17.2 mmol) and the reaction was heated to 80 C. After 6 hr, the reaction was extracted from dilute NaOH using EtOAc×2. The organic layers were combined, dried over MgSO$_4$, filtered, and concentrated. The crude residue was purified by HPLC to give 1.3 g (32%) of the desired Example 1. MS found: (M+H)$^+$=478.

General Phenol Alkylative Procedure A:

To a solution of 1d (25-80 mg, 0.08-0.26 mmol) in 2 mL DMF was added Cs$_2$CO$_3$ (2 equiv.) and stirred for 15 min. The alkyl halide (1.1 equiv.) was added all at once and the reaction was stirred at rt overnight. The reddish reaction was quenched with TFA/water and purified by HPLC if the analytical HPLC purity was <70%; otherwise the reaction was extracted from dilute NaHCO$_3$ using EtOAc×3, the combined organic layers were dried over MgSO$_4$, filtered, and concentrated by rotary evaporator. The product from either workup was coupled using General Coupling Method A to give the final products.

General Phenol Alkylative Procedure B:

To a solution of 1d (100 mg, 0.49 mmol) in 1 mL DMSO was added NaH (10 mg of 60% oil dispersed, 0.24 mmol) and stirred for 10 min. The alkyl halide (0.24 mmol) was added all at once and the reaction was stirred at rt for approx. 30 min and monitored by TLC. The reddish reaction was quenched with TFA/water and purified by HPLC. The product was coupled using General Coupling Method A to give the final products.

Example 2

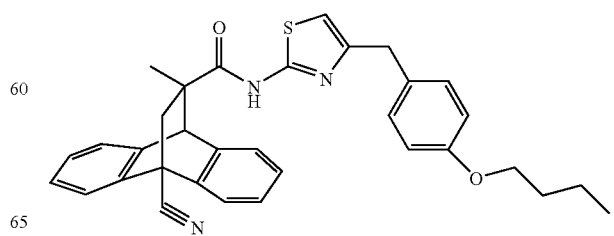

Example 2 was prepared using General Phenol Alkylative Procedure B and iodobutane to give 44 mg (70%) of intermediate ether. MS found: (M+H)$^+$=263. 30 mg (0.11 mmol) of this intermediate was coupled to Core B (25 mg, 0.08 mmol) using General Coupling Method A to give 24 mg (56%) of Example 2. MS found: (M+H)$^+$=534.

Example 3

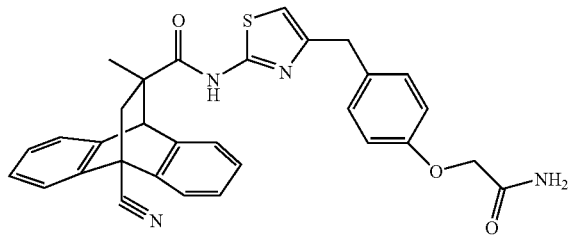

Example 3 was prepared using General Phenol Alkylative Procedure A and iodoacetamide to give 71 mg (69%) of intermediate ether. MS found: (M+H)$^+$=264. 34 mg (0.13 mmol) of this intermediate was coupled to Core B (40 mg, 0.13 mmol) using General Coupling Method A to give 44 mg (63%) of Example 3. MS found: (M+H)$^+$=535.

Example 4

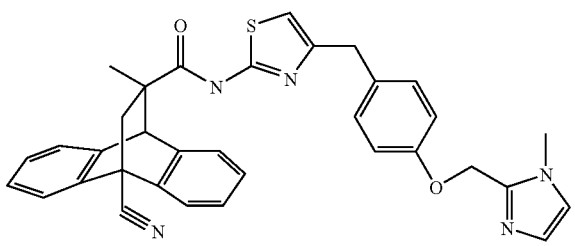

Example 4 was prepared using General Phenol Alkylative Procedure A and 2-(chloromethyl)-1-methyl-1H-imidazole hydrochloride to give the intermediate ether. MS found: (M+H)$^+$=301. All of this intermediate was coupled to Core B (30 mg, 0.10 mmol) using General Coupling Method A to give 47 mg (82%) of Example 4. MS found: (M+H)$^+$=572.

Example 5

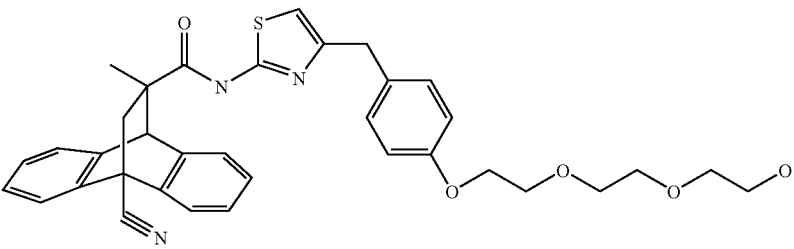

Example 5 was prepared using General Phenol Alkylative Procedure A and 2-[2-(2-chloroethoxy)ethoxy]ethanol to give the 55 mg (12%) of intermediate ether. MS found: (M+H)$^+$=339. All of this intermediate was coupled to Core B (50 mg, 0.16 mmol) using General Coupling Method A to give 10 mg (10%) of Example 5. MS found: (M+H)$^+$=610.

Example 6

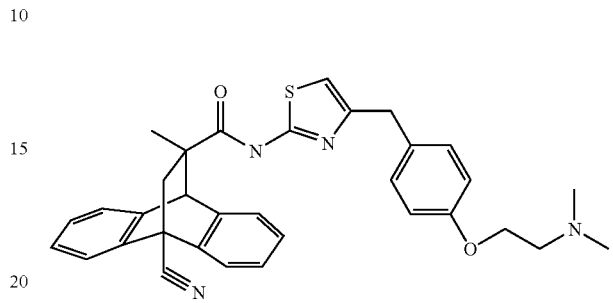

Example 6 was prepared using General Phenol Alkylative Procedure A and 2-(dimethylamino)ethyl chloride hydrochloride to give the intermediate ether. MS found: (M+H)$^+$=278. All of this intermediate was coupled to Core B (30 mg, 0.10 mmol) using General Coupling Method A to give 44 mg (10%) of Example 6 as a TFA salt. MS found: (M+H)$^+$=549.

Example 7

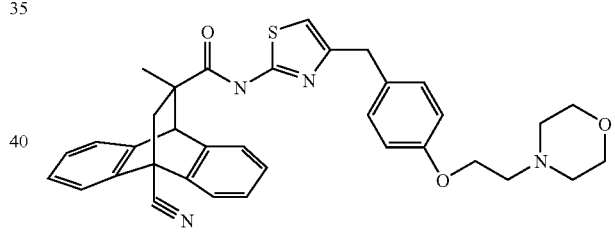

Example 7 was prepared using General Phenol Alkylative Procedure B and 2-(dimethylamino)ethyl chloride hydrochloride to give the intermediate ether. MS found: (M+H)$^+$=320. All of this intermediate was coupled to Core B (30 mg, 0.10 mmol) using General Coupling Method A to give 26 mg (37%) of Example 7 as a TFA salt. MS found: (M+H)$^+$=591.

Example 8

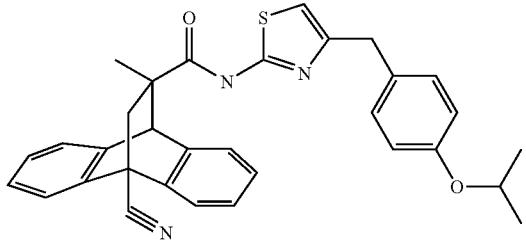

Example 8 was prepared using General Phenol Alkylative Procedure A and 2-iodopropane to give 44 mg (36%) of the intermediate ether. MS found: (M+H)⁺=249. 30 mg (0.12 mmol) of this intermediate was coupled to Core B (30 mg, 0.10 mmol) using General Coupling Method A to give 24 mg (48%) of Example 8. MS found: (M+H)⁺=520

Example 9

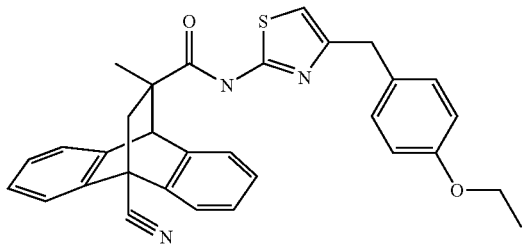

Example 9 was prepared using General Phenol Alkylative Procedure A and 2-iodoethane to give 32 mg (36%) of the intermediate ether. MS found: (M+H)⁺=235. 30 mg (0.13 mmol) of this intermediate was coupled to Core B (30 mg, 0.10 mmol) using General Coupling Method A to give 32 mg (66%) of Example 9. MS found: (M+H)⁺=506.

Example 10

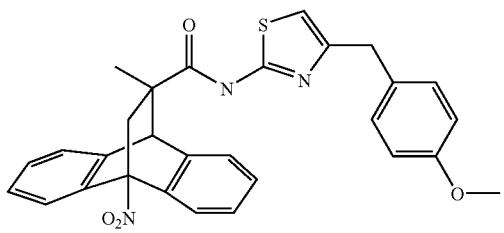

(a) Applying the method of Mazzocchi et al (*Synth. Commun.* 1986, 309-312) a cuprate was prepared from 4-methoxyphenylmagnesium bromide (20 mmol, 40 mL of 0.5 M THF solution) and CuBr (574 mg, 2.0 mmol) in 50 mL anhydrous ether. The cuprate was treated with epichlorohydrin (1.94 g, 21 mmol) and stirred at −40 C for 20 hr. The reaction was quenched with water, extracted 2×Et₂O, and the ethereal extracts were dried over MgSO₄. The solution was filtered, concentrated by rotary evaporator, and chromatographed on SiO₂ using 25% EtOAc in hexanes to give 888 mg (22%) of the chlorohydrin 10a as a yellow oil. ¹H-NMR (400 MHz, CDCl₃): δ 7.18 (d, 2H), 6.88 (d, 2H), 4.0 (m, 1H), 3.82 (s, 3H), 3.65 (dd, 1H), 3.52 (dd, 1H), 2.83 (d, 2H).

(b) Following the procedure of Example (1b), 10a (888 mg, 4.44 mmol) was subjected to the same Dess-Martin oxidation to form 762 mg (86%) of chloromethylketone 10b which underwent the Hantzch cyclization using thiourea to give 208 mg (80%) of the aminothiazole 10c which is a yellow solid. MS found: (M+H)⁺=221.

(c) Aminothiazole 10c (39 mg, 0.18 mmol) was coupled to Core C (53 mg, 0.17 mmol) using General Coupling Method B. Obtained 52 mg (57%) of Example 10. MS found: (M+H)⁺=512.

Example 11

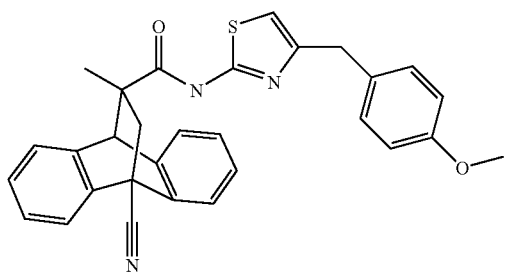

10c (73 mg, 0.33 mmol) was coupled to Core B (50 mg, 0.17 mmol) using General Coupling Method A in acetonitrile. Obtained 64 mg (73%) of Example 11. MS found: (M+H)⁺=492.

Example 12

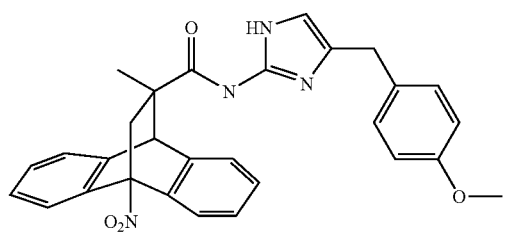

Following the procedure of Little and Webber (*J. Org. Chem.* 1994, 59, 7299-7305), a solution of N-acetylguanidine (470 mg, 4.6 mmol) was dissolved in 8 mL DMF and treated with compound 10b (460 mg, 2.3 mmol) in 2 ML DMF dropwise over 10 min. The reaction was stirred at rt overnight, concentrated in vacuo, treated with 10 mL 12 M HCl and heated to reflux for 2 hr. The reaction was cooled, filtered, and the supernatant was purified by HPLC to give 45 mg (11%) of the 2-aminoimidazole 12a. All of this intermediate was coupled to Core C (44 mg, 0.14 mmol) using General Coupling Method B. Obtained 16 mg (18%) of Example 12. MS found: (M+H)⁺=495.

Example 13

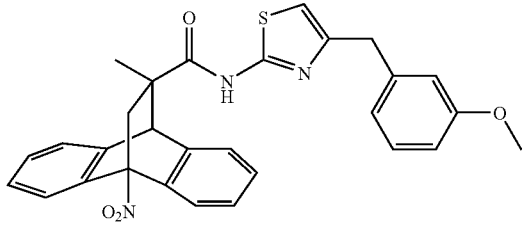

(a) Applying the method of Mazzocchi et al (*Synth. Commun.* 1986, 309-312) a cuprate was prepared from 3-methoxyphenylmagnesium bromide (20 mmol, 20 mL of 1.0 M THF solution) and CuBr (574 mg, 2.0 mmol) in 50 mL anhydrous ether. The cuprate was treated with epichlorohydrin (1.94 g, 21 mmol) and stirred at −78 C for 24 hr. The reaction was quenched with water, extracted 3×Et$_2$O, and the ethereal extracts were dried over MgSO$_4$. The solution was filtered, concentrated by rotary evaporator, and chromatographed on SiO$_2$ using 10% EtOAc in hexanes to give 476 mg (12%) of the chlorohydrin 13a as a yellow oil. $^1$H-NMR (400 MHz, CDCl$_3$): δ 7.10 (d, 1H), 6.68 (m, 3H), 3.91 (m, 1H), 3.65 (s, 3H), 3.47 (dd, 1H), 3.36 (dd, 1H), 2.71 (d, 2H), 2.05 (br s, 1H).

(b) Following the procedure of Example (1b), 13a (70 mg, 0.35 mmol) was subjected to the same Dess-Martin oxidation to form 68 mg (97%) of chloromethylketone 13b which underwent the Hantzch cyclization using thiourea to give 76 mg (100%) of the aminothiazole 13c. MS found: (M+H)$^+$=221.

(c) Aminothiazole 13c (39 mg, 0.18 mmol) was coupled to Core C (56 mg, 0.18 mmol) using General Coupling Method B. Obtained 16 mg (18%) of Example 13. MS found: (M+H)$^+$=512.

Example 14

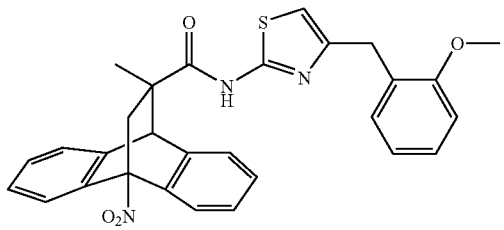

(a) Applying the method of Lipshutz et al (*J. Org. Chem.* 1984, 49, 3928-3938) a cuprate was prepared from 2-methoxyphenylmagnesium bromide (20 mmol, 20 mL of 1.0 M THF solution) and CuCN (896 mg, 10 mmol) in 100 mL anhydrous THF. The cuprate was treated with epichlorohydrin (1.85 g, 20 mmol) and stirred at −78 C for 18 hr. The reaction was quenched with sat NH$_4$Cl, extracted 3×EtOAc, and the organic extracts were dried over MgSO$_4$, filtered, and concentrated by rotary evaporator. The residue was chromatographed on SiO$_2$ using 25% EtOAc in hexanes to give 3.8 g (95%) of the chlorohydrin 14a. MS found: (M+H)$^+$=201.

(b) Following the procedure of Example (1b), 14a (1.7 g, 8.5 mmol) was subjected to the same Dess-Martin oxidation to give 1.4 g (27%) of chloromethylketone 14b which underwent the Hantzch cyclization using thiourea to give 451 mg (41%) of the aminothiazole 14c. MS found: (M+H)$^+$=221.

(c) Aminothiazole 14c was coupled to Core C (50 mg, 0.16 mmol) using General Coupling Method B. Obtained 39 mg (48%) of Example 14. MS found: (M+H)$^+$=512.

Example 15

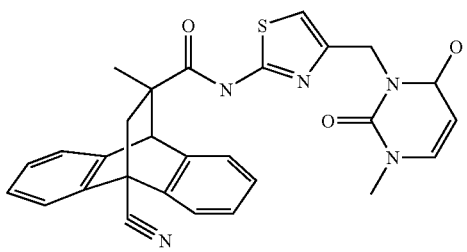

(a) To a solution of 3-methyluracil (25 mg, 0.2 mmol) in 0.2 mL DMSO was added NaH (8 mg 60% oil dispersed, 0.2 mmol). After H$_2$ evolution ceased, 2-amino-4-(chloromethyl)thiazole hydrochloride (15 mg, 0.08 mmol, prepared according to Sprague et al *J. Am. Chem. Soc.* 1946, 2155; 2158) in 0.2 mL DMSO was added and the reaction was stirred for 3 hr at rt. The reaction was purified directly by HPLC to give 16 mg (84%) of the N-substituted uracil 15a. MS found: (M+H)$^+$=239.

(b) Compound 15a (40 mg, 0.17 mmol) was coupled to Core B (32 mg, 0.11 mmol) using General Coupling Method A. Obtained 10 mg (18%) of Example 15. MS found: (M+H)$^+$=510.

Example 16

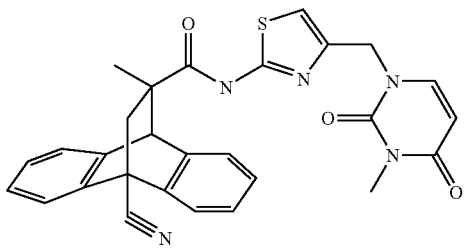

(a) To a solution of 1-methyluracil (105 mg, 0.83 mmol) in 1.2 mL DMSO was added NaH (33 mg 60% oil dispersed, 0.83 mmol). After H$_2$ evolution ceased, 2-amino-4-(chloromethyl)thiazole hydrochloride (62 mg, 0.33 mmol, prepared according to Sprague et al *J. Am. Chem. Soc.* 1946, 2155; 2158) was added and the reaction was stirred at rt overnight. The reaction was diluted with 4 mL water, treated with 0.5 mL TFA, and purified by HPLC to give 15 mg (19%) of the N-substituted uracil 16a. MS found: (M+H)$^+$=239.

(b) Compound 16a (15 mg, 0.06 mmol) was coupled to Core B (20 mg, 0.68 mmol) using General Coupling Method A. Obtained 7 mg (22%) of Example 16. MS found: (M+H)$^+$=510.

Example 17

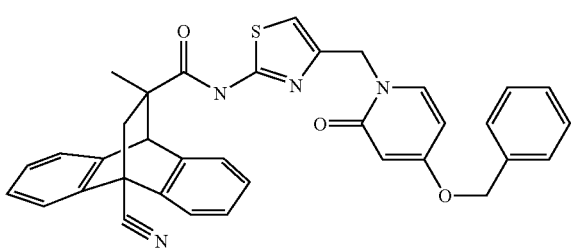

(a) To a solution of 4-benzyloxy-2-(1H)-pyridone (217 mg, 1.08 mmol) and Cs$_2$CO$_3$ (704 mg, 2.16 mmol) in 2 mL DMF was added a solution of 2-amino-4-(chloromethyl)thiazole hydrochloride (200 mg, 1.08 mmol, prepared according to Sprague et al *J. Am. Chem. Soc.* 1946, 2155; 2158) in 2 mL DMF dropwise over 5 min. The reaction was stirred at rt overnight, acidified with TFA, and purified by HPLC to give 51 mg (15%) of the N-substituted pyridone 17a that was contaminated with a small amount of the O-alkylated pyridone. MS found: (M+H)$^+$=314.

(b) Compound 17a (35 mg, 0.11 mmol) was coupled to Core B (35 mg, 0.12 mmol) using General Coupling Method A. Obtained 51 mg (79%) of Example 17. $^1$H-NMR (400 MHz, DMSO): δ 12.4 (s, 1H), 7.2-7.7 (m, 14H), 6.85 (s, 1H), 6.10 (dd, 1H), 5.95 (d, 1H), 5.10 (d, 4H), 5.05 (d, 1H), 3.20 (d, 1H), 1.78 (d, 1H), 1.14 (s, 3H).

Example 18

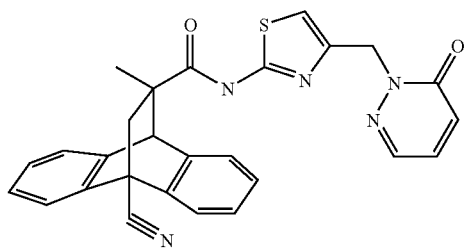

(a) 3(2H)-pyridazinone (104 mg, 1.08 mmol) and 2-amino-4-(chloromethyl)thiazole hydrochloride (200 mg, 1.08 mmol, prepared according to Sprague et al *J. Am. Chem. Soc.* 1946, 2155; 2158) were coupled using the same procedure as used for 17a to give 26 mg (12%) of the N-substituted pyridone 18a that was contaminated with a small amount of the O-alkylated pyridone. MS found: (M+H)$^+$=209.

(b) Compound 18a (24 mg, 0.11 mmol) was coupled to Core B (36 mg, 0.12 mmol) using General Coupling Method A. Obtained 32 mg (56%) of Example 18. MS found: (M+H)$^+$=480.

Example 19

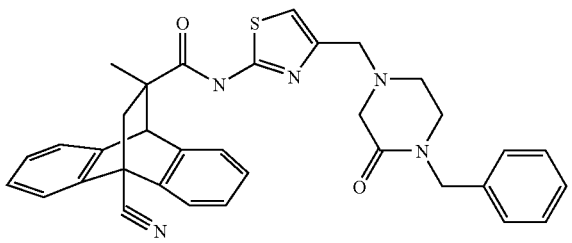

(a) 1-benzylpiperazin-2-one (100 mg, 0.53 mmol) and 2-amino-4-(chloromethyl)thiazole hydrochloride (98 mg, 0.53 mmol, prepared according to Sprague et al *J. Am. Chem. Soc.* 1946, 2155; 2158) were coupled using the same procedure as used for 17a except that K$_2$CO$_3$ (88 mg, 0.64 mmol) was used in place of Cs$_2$CO$_3$ to give 52 mg (24%) of the N-substituted piperazinone 19a as a TFA salt. MS found: (M+H)$^+$=303.

(b) Compound 19a (24 mg, 0.11 mmol) was coupled to Core B (36 mg, 0.12 mmol) using General Coupling Method A. Obtained 19 mg (32%) of Example 19. MS found: (M+H)$^+$=574.

Example 20

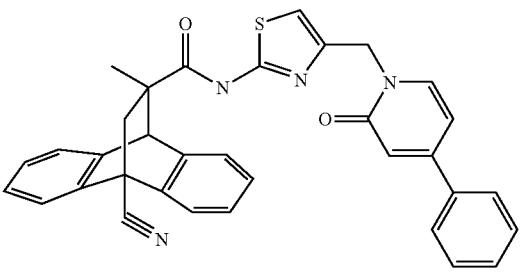

(a) 4-phenyl-2-1H-pyridone (200 mg, 1.17 mmol, prepared according to *J. Org. Chem.* 2002, 67, 4304-4308) and 2-amino-4-(chloromethyl)thiazole hydrochloride (217 mg, 1.17 mmol, prepared according to Sprague et al *J. Am. Chem. Soc.* 1946, 2155; 2158) were coupled using the same procedure as used for 17a to give 300 mg (91%) of the N-substituted piperazinone 20a. MS found: (M+H)$^+$=284.

(b) Compound 20a (33 mg, 0.11 mmol) was coupled to Core B (36 mg, 0.12 mmol) using General Coupling Method A. Obtained 17 mg (26%) of Example 20. MS found: (M+H)$^+$=555.

Example 21

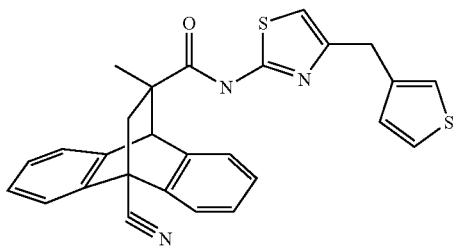

(a) Following the procedure of Nugent et al (*J. Org. Chem.* 2004, 69, 1629-1633) trimethylsulfoxonium iodide (7.04 g, 32 mmol) was suspended in 62 mL dry THF and treated with potassium tert-butoxide (32 mL 1.0 M, 32 mmol). The solution was refluxed under $N_2$ for 2 hr, cooled to rt, and treated with methyl thiophene-3-acetate (2.0 g, 12.8 mmol) and stirred for 48 hr. The reaction was quenched with water and extracted 3×EtOAc, the organic layers were dried over $MgSO_4$, filtered, and concentrated by rotary evaporator. The oily residue was taken up in 25 mL EtOAc and 5 mL hexane and after 2 hr, 1.1 g of yellow crystalline ylide 21a was isolated by filtration. MS found: $(M+H)^+=217$.

(b) Thiourea (183 mg, 2.3 mmol) was dissolved in 10 mL warm EtOH followed by ylide 21a (500 mg, 2.3 mmol), and finally HCl in dioxane (0.52 mL of 4.0 M, 2.08 mmol) dropwise over 10 min. The reaction was refluxed under $N_2$ for 5 min and then concentrated to a dark brown oil 21b. MS found: $(M+H)^+=197$.

(c) Compound 21b (25 mg, 0.13 mmol) was coupled to Core B (40 mg, 0.14 mmol) using General Coupling Method A. Obtained 15 mg (23%) of Example 21. MS found: $(M+H)^+=468$.

Example 22

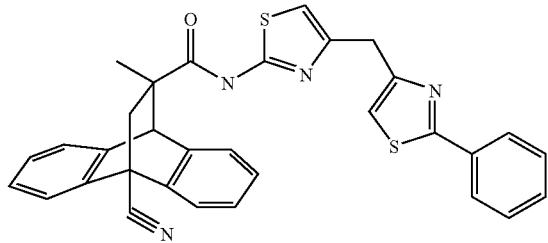

(a) Followed the exact procedure as used for Example 21. Starting with 2-(2-phenyl-1,3-thiazol-4-yl) acetic acid methyl ester (2.0 g, 8.58 mmol) and dimethylsulfoxonium methylide (32 mmol) to give the ylide 22a. MS found: $(M+H)^+=294$.

(b) Followed the same procedure as used for Example 21. Starting with 22a (500 mg, 1.71 mmol) and thiourea (135 mg, 1.73 mmol), and HCl in dioxane (0.38 mL of 4M, 1.52 mmol). The product was purified by HPLC to give 150 mg (32%) of aminothiazole 22b. MS found: $(M+H)^+=274$.

(c) Compound 22b (35 mg, 0.13 mmol) was coupled to Core B (40 mg, 0.14 mmol) using General Coupling Method A. Obtained 18 mg (24%) of Example 22. MS found: $(M+H)^+=468$.

Example 23

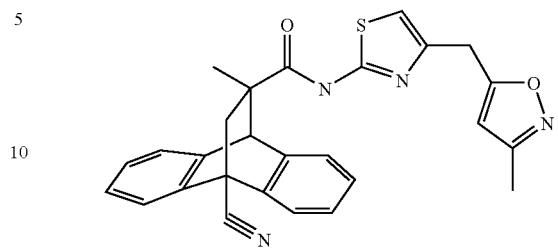

(a) Followed the exact procedure as used for Example 21. Starting with 3-methyl-5-isoxazole acetic acid methyl ester (2.5 g, 16.1 mmol) and dimethylsulfoxonium methylide (32 mmol) to give 1.17 g (34%) the ylide 23a. MS found: $(M+H)^+=216$.

(b) Followed the same procedure as used for Example 21 starting with 23a (500 mg, 2.56 mmol) and thiourea (200 mg, 2.56 mmol), and HCl in dioxane (0.58 mL of 4M, 2.3 mmol). The product was purified by HPLC to give aminothiazole 23b. MS found: $(M+H)^+=196$.

(c) Compound 23b (15 mg, 0.0.07 mmol) was coupled to Core B (27 mg, 0.09 mmol) using General Coupling Method A. Obtained 9 mg (28%) of Example 23. MS found: $(M+H)^+=467$.

Example 24

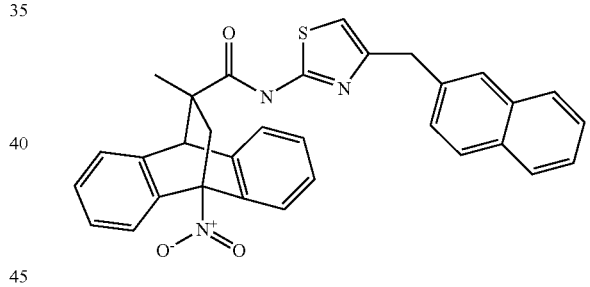

(a) Following the general method of Example 14, a cuprate was formed from 2-naphthyl magnesium bromide (20 mL of 0.5 M, 10 mmol) and CuCN (448 mg, 5.0 mmol) at −78 C and then treated with epichlorohydrin (1.85 g, 20 mmol) at −40 C and allowed to warm to rt overnight. The reaction was quenched with sat $NH_4Cl$, extracted 3×EtOAc, and the organic extracts were dried over $MgSO_4$, filtered, and concentrated by rotary evaporator. The residue was chromatographed on $SiO_2$ using 25% EtOAc in hexanes to give 1.05 g (48%) of the chlorohydrin 24a. MS found: $(M+H)^+=221$.

(b) Following the procedure of Example (1b), 24a (263 mg, 1.0 mmol) was subjected to the same Dess-Martin oxidation to give 245 mg (93%) of chloromethylketone 24b which underwent the Hantzch cyclization using thiourea to give 225 mg (100%) of the aminothiazole 14c. MS found: $(M+H)^+=241$.

(c) Aminothiazole 24c (77 mg, 0.32 mmol) was coupled to Core D (50 mg, 0.16 mmol) using General Coupling Method A. Obtained 44 mg (52%) of Example 24. MS found: $(M+H)^+=532$.

Example 25

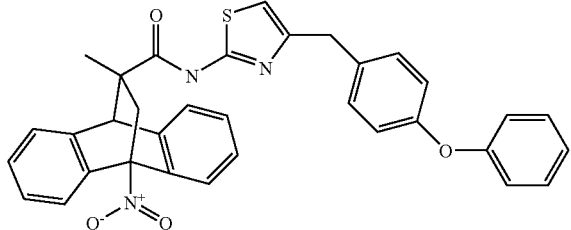

(a) Following the general method of Example 14, a cuprate was formed from 4-phenoxyphenyl magnesium bromide (10 mL of 0.5 M in THF, 5 mmol) and CuCN (224 mg, 2.5 mmol) at −78 C and then treated with epichlorohydrin (694 mg, 7.5 mmol) at −40 C and allowed to warm to rt overnight. The reaction was quenched with sat NH$_4$Cl, extracted 3×EtOAc, and the organic extracts were dried over MgSO$_4$, filtered, and concentrated by rotary evaporator. The residue was chromatographed on SiO$_2$ using 25% EtOAc in hexanes to give 650 mg (50%) of the chlorohydrin 25a. MS found: (M+H)$^+$=263.

(b) Following the procedure of Example (1b), 25a (150 mg, 0.68 mmol) was subjected to the same Dess-Martin oxidation to give chloromethylketone 25b which underwent the Hantzch cyclization using thiourea to give the aminothiazole 25c which was used without further purification. MS found: (M+H)$^+$=283.

(c) Aminothiazole 25c (90 mg, 0.32 mmol) was coupled to Core D (50 mg, 0.16 mmol) using General Coupling Method A. Obtained 36 mg (39%) of Example 25. MS found: (M+H)$^+$=574.

Example 26

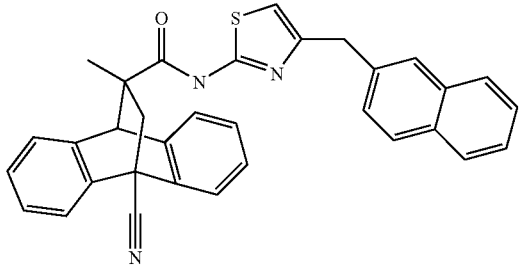

25c (60 mg, 0.25 mmol) was coupled to Core A (37 mg, 0.13 mmol) using General Coupling Method B in DMF. Obtained 31 mg (48%) of Example 26. MS found: (M+H)$^+$=512.

Example 27

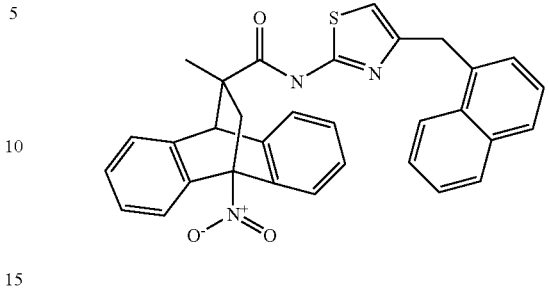

(a) To a solution of 1-bromonaphthalene (2.7 g, 13 mmol) in dry THF (120 mL) and cooled to −78 C was added n-BuLi (4 mL of 2.5 M, 10 mmol) dropwise. After stirring 30 min, epichlorohydrin (1.0 g, 13 mmol) was added all at once and the reaction was warmed to 0 C and stirred for 2 hr. The reaction was quenched with water, extracted 2×EtOAc, the combined organic layers were dried over MgSO$_4$, filtered, and concentrated by rotary evaporator. The residue was chromatographed on SiO$_2$ using 10% EtOAc in hexanes to give 1.08 g (42%) of the chlorohydrin 27a. $^1$H-NMR (400 MHz, CDCl$_3$): δ 7.99 (d, 1H), 7.81 (d, 1H), 7.70 (d, 1H), 7.44-7.49 (m, 2H), 7.31-7.37 (m, 2H), 4.13 (m, 1H), 3.43-3.55 (m, 2H), 3.22-3.28 (m, 2H).

(b) Following the procedure of Example (1b), 27a (350 mg, 1.33 mmol) was subjected to the same Dess-Martin oxidation to give chloromethylketone 27b (MS found: (M+H)$^+$=219) which underwent the Hantzch cyclization using thiourea (114 mg, 1.5 mmol) to give 310 mg (97%) of the aminothiazole 27c. MS found: (M+H)$^+$=283.

(c) Aminothiazole 27c (50 mg, 0.21 mmol) was coupled to Core D (30 mg, 0.096 mmol) using General Coupling Method A. Obtained 49 mg (96%) of Example 27. MS found: (M+H)$^+$=532.

Example 28

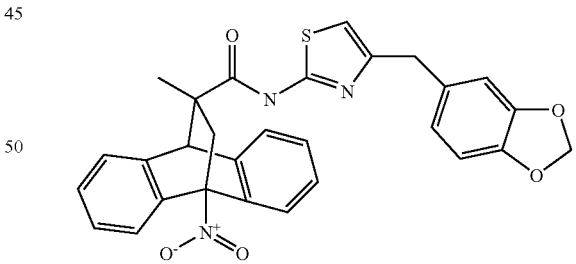

(a) Following the general method of Example 14, a cuprate was formed from 3,4-(methylenedioxy)phenyl magnesium bromide (10 mL of 1.0 M in THF, 10 mmol) and CuCN (448 mg, 5.0 mmol) at −40 C and after 1 h, treated with epichlorohydrin (1.39 mg, 15 mmol) at −40 C and allowed to warm to rt overnight. The reaction was quenched with sat NH$_4$Cl, extracted 3×EtOAc, and the organic extracts were dried over MgSO$_4$, filtered, and concentrated by rotary evaporator. The residue was chromatographed on SiO$_2$ using 90% EtOAc in hexanes to give 2.0 g (62%) of the chlorohydrin 28a. MS found: (M+H)$^+$=215.

(b) Following the procedure of Example (1b), 28a (500 mg, 2.33 mmol) was subjected to the same Dess-Martin oxidation to give chloromethylketone 28b which underwent the Hantzch cyclization using thiourea to give 240 mg (44%) of the aminothiazole 28c. MS found: (M+H)+=235.

(c) Aminothiazole 28c (46 mg, 0.20 mmol) was coupled to Core D (30 mg, 0.096 mmol) using General Coupling Method A. Obtained 30 mg (59%) of Example 28. MS found: (M+H)+=526.

Example 29

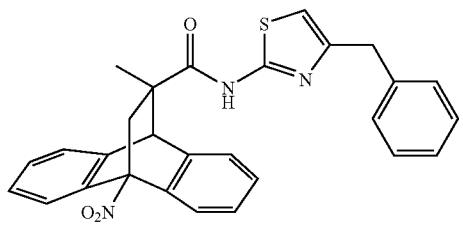

(a) To a solution of commercially available phenylacetone (13.2 g, 98.6 mmol) in 30 mL of acetic acid and 15 mL of 48% HBr was added a solution of bromine (34.7 g, 217 mmol) in 50 mL of acetic acid dropwise. After 4 hr, acetone (150 mL) was added and the reaction mixture was stirred for 3 d. The reaction was concentrated by rotary evaporator, diluted with brine, and extracted 2×DCM. The DCM extracts were dried over MgSO$_4$. The solution was filtered, concentrated by rotary evaporator, and chromatographed on SiO$_2$ using DCM to give 20.8 g (98%) of a dark oil 29a. $^1$H-NMR (400 MHz, CDCl$_3$): δ 7.08-7.25 (m, 5H), 3.82 (s, 2H), 3.78 (s, 2H).

(b) To a solution of 29a (2.2 g, 10 mmol) in 100 mL of EtOH was added thiourea (1.0 g, 13 mmol) all at once. The reaction was heated at reflux for 4 hr. The reaction was concentrated by rotary evaporator and the crude residue was purified on SiO$_2$ using 5% MeOH in EtOAc to give 1.8 g (95%) of pure 29b. MS found: (M+H)+=191.

(c) 29b (38 mg, 0.2 mmol) was coupled with Core C (50 mg, 0.16 mmol) using General Coupling Method B. The product was purified by HPLC to give 48 mg (50%) of the desired product 29. MS found: (M+H)+=482.

Example 30

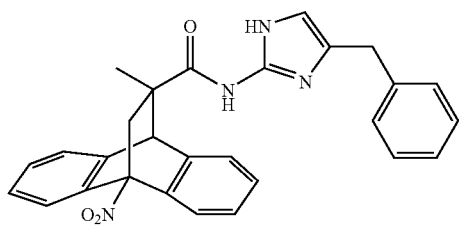

(a) A solution of 29a (5.0 g, 23.5 mmol) in 20 mL of DMF was added dropwise to a solution of commercially available acetylguanidine (4.8 g, 47 mmol) in 30 mL of DMF at 0 C. The reaction was allowed to slowly warm to rt and stirred for 24 hr. The reaction was diluted with brine and extracted 2×EtOAc. The EtOAc extracts were dried over MgSO$_4$. The solution was filtered, concentrated by rotary evaporator, and the residue was triturated with EtOAc/hexanes. The resulting solid was collected to give 320 mg (6%) of pure 30a. MS found: (M+H)+=216.

(b) 30a (32 mg, 0.15 mmol) was heated at 80 C in a solution of 1 mL of conc HCl and 2 mL of MeOH for 1 hr. The reaction mixture was concentrated by rotary evaporator to give a quantitative yield of 30b as the HCl salt.

(c) 30b (0.15 mmol) was coupled with Core C (50 mg, 0.16 mmol) using General Coupling Method B. The product was purified by HPLC to give 51 mg (73%) of the desired product 30. MS found: (M+H)+=445.

Example 31

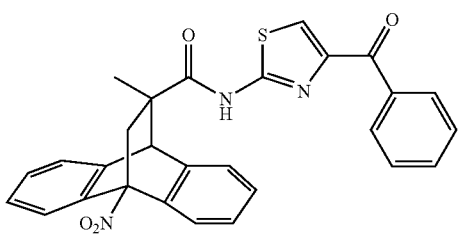

(a) To a solution of commercially available 1-phenyl-1,2-propanedione (3.3 g, 27.3 mmol) in 30 mL of was added a solution of bromine (34.7 g, 217 mmol) in 5 mL of CHCl$_3$ dropwise. The reaction was heated at reflux for 12 hr. The reaction was diluted with water and extracted 2×CHCl$_3$. The CHCl$_3$ extracts were dried over MgSO$_4$, filtered, and concentrated by rotary evaporator to give 5.0 g (100%) of a dark solid 52a. $^1$H-NMR (400 MHz, CDCl$_3$): δ 8.03 (d, 2H), 7.68 (t, 1H), 7.53 (dd, 2H), 4.4 (s, 2H).

(b) To a solution of 31a (1.5 g, 6.6 mmol) in 25 mL of EtOH was added thiourea (0.55 g, 7.2 mmol) all at once. The reaction was heated at reflux for 4 hr. The reaction was diluted with water and extracted 2×EtOAC. The EtOAc extracts were dried over MgSO$_4$, filtered, and concentrated by rotary evaporator to give 1.28 g (89%) of 31b. MS found: (M+H)+=205.

(c) 31b (38 mg, 0.2 mmol) was coupled with Core C (50 mg, 0.16 mmol) using General Coupling Method B. The product was purified by HPLC to give 48 mg (50%) of the desired product 31. MS found: (M+H)+=496.

Example 32

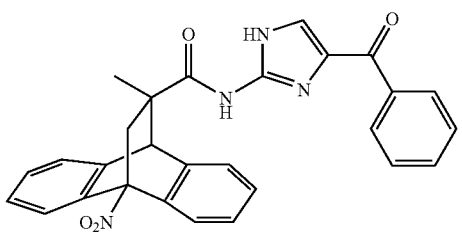

(a) A solution of 31a (1.0 g, 4.4 mmol) in 10 mL of DMF was added dropwise to a solution of commercially available acetylguanidine (0.89 g, 8.8 mmol) in 10 mL of DMF at 0 C. The reaction was allowed to slowly warm to rt and stirred for 24 hr. The reaction was diluted with brine and extracted 2×EtOAc. The EtOAc extracts were dried over MgSO$_4$. The solution was filtered, concentrated by rotary evaporator, and the residue was triturated with EtOAc/hexanes. The resulting solid was collected to give 60 mg (6%) of 32a. MS found: (M+H)$^+$=230.

(b) 32a (57 mg, 0.25 mmol) was heated at 80 C in a solution of 1 mL of conc HCl and 2 mL of MeOH for 1 hr. The reaction mixture was concentrated by rotary evaporator to give a quantitative yield of 32b as the HCl salt.

(c) 32 (0.15 mmol) was coupled with Core C (50 mg, 0.16 mmol) using General Coupling Method B. The product was purified by HPLC to give 9 mg (12%) of the desired product 32. MS found: (M+H)$^+$=479.

Example 33

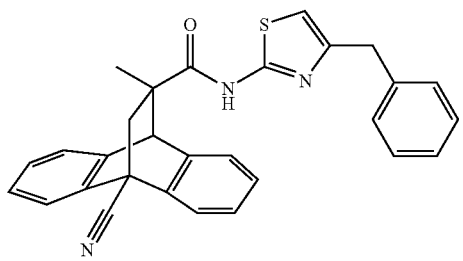

29b (38 mg, 0.2 mmol) was coupled with Core A (50 mg, 0.17 mmol) using General Coupling Method B. The product was purified by HPLC to give 48 mg (50%) of the desired product 33. MS found: (M+H)$^+$=462.

Example 34

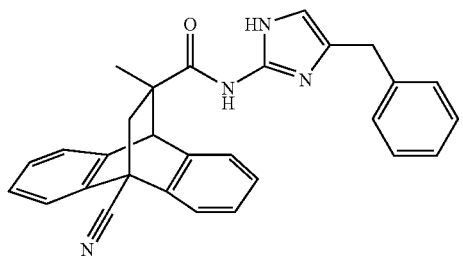

(a) 30a (43 mg, 0.2 mmol) was heated at 80 C in a solution of 1 mL of conc HCl and 2 mL of MeOH for 1 hr. The reaction mixture was concentrated by rotary evaporator to give a quantitative yield of 34a as the HCl salt.

(b) 34a (0.2 mmol) was coupled with Core C (50 mg, 0.16 mmol) using General Coupling Method B. The product was purified by HPLC to give 10 mg (13%) of the desired product 34. MS found: (M+H)$^+$=445.

Example 35

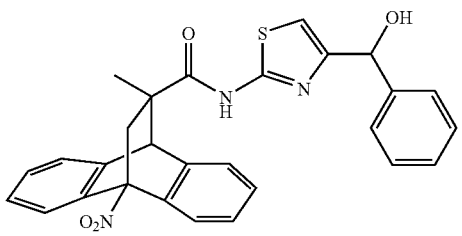

(a) 31b (41 mg, 0.2 mmol) was coupled with Core C (50 mg, 0.16 mmol) using General Coupling Method B. The product was purified by HPLC to give 72 mg (72%) of the desired product 35a. MS found: (M+H)$^+$=496.

(b) 35a was dissolved in 5 mL of MeOH and NaBH$_4$ (0.2 mmol) was added in one portion. Stirred for 1 hr then purified by HPLC to give 65 mg (90%) of desired product 35. MS found: (M+H)$^+$=498.

Example 36

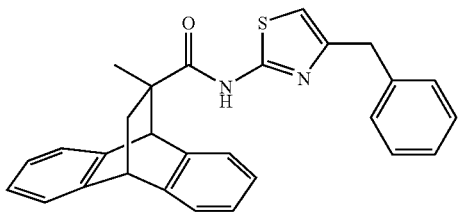

29b (36 mg, 0.19 mmol) was coupled with 9,10-dihydro-11-methyl-9,10-ethanoanthracene-11-carboxylic acid (50 mg, 0.19 mmol) using General Coupling Method B. The product was purified by HPLC to give 60 mg (73%) of the desired product 36. MS found: (M+H)$^+$=437.

Example 37

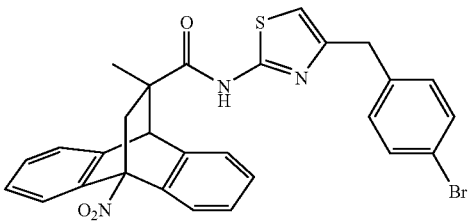

(a) To a solution of commercially available 4-bromophenylacetone (25 g, 117 mmol) in 30 mL of acetic acid and 15 mL of 48% HBr was added a solution of bromine (40 g, 217 mmol) in 50 mL of acetic acid. After 4 hr, acetone (150 mL) was added and the reaction mixture was stirred for 3 d. The reaction was concentrated by rotary evaporator, diluted with brine, and extracted 2×DCM. The DCM extracts were dried over MgSO$_4$. The solution was filtered, concentrated by rotary evaporator, and chromatographed on SiO$_2$ using DCM to give 20.8 g (98%) of a dark oil 37a. ¹H-NMR (400 MHz, CDCl₃): δ 7.49 (d, 2H), 7.12 (d, 2H), 3.94 (s, 2H), 3.92 (s, 2H).

(b) To a solution of 37a (116 mmol) in 200 mL of EtOH was added thiourea (9.0 g, 118 mmol) all at once. The reaction was heated at reflux for 4 hr. The reaction was concentrated by rotary evaporator and the crude residue was dissolved in EtOAc and extracted 3×1N HCl. The aqueous extracts were basified with 1N NaOH and then extracted 2×EtOAC. EtOAc extracts were dried over MgSO₄, and solid was triturated in 10% hexanes in EtOAc. Solid was collected and dried in vacuo to give 18 g (57%) of pure 37b. MS found: (M+H)⁺=270.

(c) 37b (107 mg, 0.4 mmol) was coupled with Core D (60 mg, 0.2 mmol) using General Coupling Method A. The product was chromatographed on SiO₂ using DCM to give 85 mg (76%) of a white solid 37. MS found: (M+H)⁺=561.

Example 38

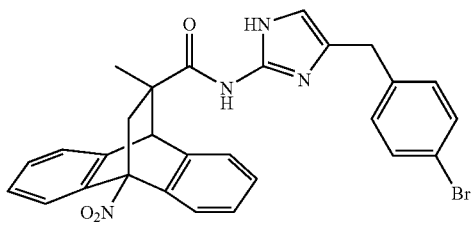

(a) A solution of 37a (50 mmol) in 50 mL of DMF was added dropwise to a solution of commercially available acetylguanidine (10.0 g, 47 mmol) in 100 mL of DMF at 0 C. The reaction was allowed to slowly warm to rt and stirred for 24 hr. The reaction was diluted with brine and extracted 2×EtOAc. The EtOAc extracts were dried over MgSO₄. The solution was filtered, concentrated by rotary evaporator, and the residue was triturated with EtOAc/hexanes. The resulting solid was collected to give 2.5 g (17%) of pure 38a MS found: (M)⁺=294.

(b) 38a (500 mg, 1.7 mmol) was heated at 80 C in a solution of 1 mL of conc HCl and 2 mL of MeOH for 1 hr. The reaction mixture was concentrated by rotary evaporator to give a quantitative yield of 38b as the HCl salt. MS found: (M)⁺=252.

(c) 38b (31 mg, 0.10 mmol) was coupled with Core C (58 mg, 0.20 mmol) using General Coupling Method B. The product was purified by HPLC to give 28 mg (52%) of the desired product 38. MS found: (M+H)⁺=544.

Example 39

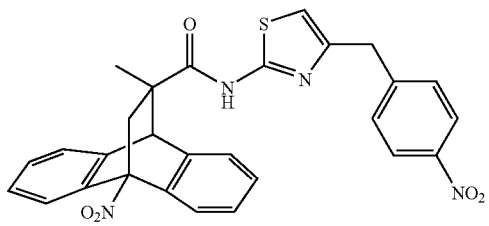

(a) To a solution of commercially available 4-nitrophenylacetone (5.0 g, 27.9 mmol) in 10 mL of acetic acid and 5 mL of 48% HBr was added a solution of bromine (8.95 g, 56 mmol) in 8 mL of acetic acid. After 4 hr, acetone (50 mL) was added and the reaction mixture was stirred for 1 d. The reaction was concentrated by rotary evaporator, diluted with brine, and extracted 2×DCM. The DCM extracts were dried over MgSO₄. The solution was filtered, concentrated by rotary evaporator, and chromatographed on SiO₂ using 50% hexanes in DCM to give 2.7 g (38%) of 39a. ¹H-NMR (400 MHz, CDCl₃): δ 8.13 (d, 2H), 7.33 (d, 2H), 3.88 (s, 2H), 3.78 (s, 2H).

(b) To a solution of 39a (103 mg, 0.4 mmol) in 10 mL of EtOH was added thiourea (30 mg, 0.4 mmol) all at once. The reaction was heated at reflux for 4 hr. The reaction was concentrated by rotary evaporator to give 120 mg (95%) of pure 39b as the HBr salt. MS found: (M+H)⁺=236.

(c) 39b (96 mg, 0.3 mmol) was coupled with Core C (62 mg, 0.20 mmol) using General Coupling Method B. The product was purified by HPLC to give 45 mg (43%) of the desired product 39. MS found: (M+H)⁺=527.

Example 40

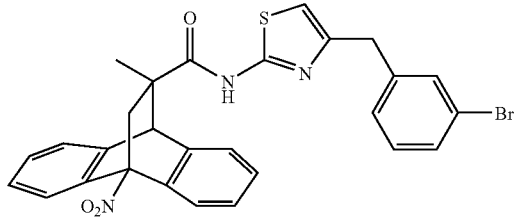

(a) To a solution of commercially available 3-bromophenylacetone (10.0 g, 47 mmol) in 15 mL of acetic acid and 8 mL of 48% HBr was added a solution of bromine (16 g, 100 mmol) in 15 mL of acetic acid dropwise. After 4 hr, acetone (100 mL) was added and the reaction mixture was stirred for 1 d. The reaction was concentrated by rotary evaporator, diluted with brine, and extracted 2×DCM. The DCM extracts were dried over MgSO₄. The solution was filtered, concentrated by rotary evaporator, and chromatographed on SiO₂ using 50% hexanes in DCM to give 40a. ¹H-NMR (400 MHz, CDCl₃): δ 7.39-7.42 (m, 2H), 7-20-7.23 (m, 2H), 3.94 (s, 2H), 3.92 (s, 2H).

(b) To a solution of 40a (47 mmol) in 100 mL of EtOH was added thiourea (3.57 g, 47 mmol) all at once. The reaction was heated at reflux for 4 hr. The reaction was diluted with EtOAc and washed with sat NaHCO₃. The EtOAc extracts were dried over MgSO₄ and concentrated by rotary evaporator to give 6.7 g (53%) of pure 40b. MS found: (M+H)⁺=270.

(c) 40b (96 mg, 0.3 mmol) was coupled with Core D (62 mg, 0.20 mmol) using General Coupling Method A. The product was purified by HPLC to give 45 mg (43%) of the desired product 40. MS found: (M+H)⁺=527.

Example 41

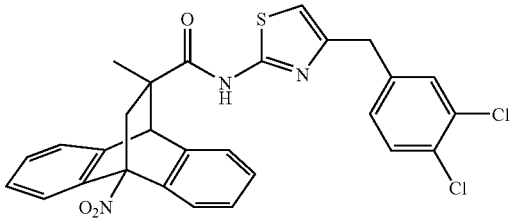

(a) To a solution of commercially available 3,4-dichlorophenylacetone (0.8 g, 3.94 mmol) in 10 mL of acetic acid and 5 mL of 48% HBr was added a solution of bromine (1.39 g, 8.7 mmol) in 5 mL of acetic acid dropwise. After 4 hr, acetone (50 mL) was added and the reaction mixture was stirred for 1 d. The reaction was concentrated by rotary evaporator, diluted with brine, and extracted 2×DCM. The DCM extracts were dried over $MgSO_4$. The solution was filtered, concentrated by rotary evaporator, and chromatographed on $SiO_2$ using 50% hexanes in DCM to give 41a. $^1$H-NMR (400 MHz, $CDCl_3$): δ 7.42 (d, 1H), 7.33 (d, 1H), 7.10 (m, 1H), 3.92 (s, 2H), 3.89 (s, 2H).

(b) To a solution of 41a (3.9 mmol) in 20 mL of EtOH was added thiourea (304 mg, 4.0 mmol) all at once. The reaction was heated at reflux for 4 hr. The reaction was diluted with EtOAc and washed with sat $NaHCO_3$. The EtOAc extracts were dried over $MgSO_4$ and concentrated by rotary evaporator to give 439 mg (43%) of pure 41b. MS found: $(M+H)^+=260$.

(c) 41b (83 mg, 0.32 mmol) was coupled with Core D (50 mg, 0.16 mmol) using General Coupling Method A. The product was purified by HPLC to give 53 mg (60%) of the desired product 41. MS found: $(M+H)^+=551$.

Example 42

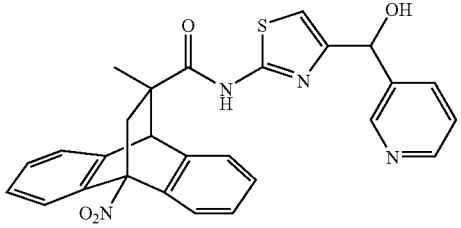

(a) To a solution of ethyl 2-[(tert-butoxycarbonyl)amino]thiazole-4-carboxylate (27.3 g, 100 mmol) prepared by the method of Kim and Kahn (*Synlett*, 1999, 8, 1239-1240) in 500 mL of THF at 0 C was added a solution of Red-Al in toluene (80 mL of 65 wt % solution) dropwise. The reaction mixture was stirred for 1 d and then quenched with water and 1N HCl. Extracted 2×EtOAc and the EtOAc extracts were dried over $MgSO_4$. The solution was filtered, concentrated by rotary evaporator, and chromatographed on $SiO_2$ using 33% hexanes in EtOAC to give 20.5 g (89%) of 2-[(tert-butoxycarbonyl)amino]-4-hydroxymethylthiazole 42a. $^1$H-NMR (400 MHz, $CDCl_3$): δ 6.98 (s, 1H), 4.81 (s, 2H), 1.81 (s, 9H).

(b) To a solution of 42a (10 g, 43.4 mmol) in 500 mL of DCM was added Dess Martin periodinane (30 g, 70.7 mmol) all at once. After 2 h, the reaction was concentrated by rotary evaporator, diluted with 1n NaOH, and extracted 3×EtOAc. The EtOAc extracts were dried over $MgSO_4$. The solution was filtered and concentrated by rotary evaporator to give 7.4 g (75%) of the yellow solid 2-[(tert-butoxycarbonyl)amino]thiazole-4-carboxaldehyde 42b. $^1$H-NMR (400 MHz, $CDCl_3$): δ 9.81 (s, 1H), 9.80 (bs, 1H), 7.73 (s, 1H), 1.47 (s, 9H).

(c) To a solution commercially available 3-iodopyridine (1.13 g, 5.5 mmol) in 15 mL of THF at 0 C was added a 2M solution of EtMgCl in THF (2.8 mL, 5.6 mmol) dropwise. After 1 h, added a solution of 42b (500 mg, 2.2 mmol) in 5 mL of THF. The reaction was allowed to warm to rt and stirred at for 1 hr. The reaction was quenched with water and extracted 2×EtOAC. The EtOAc extracts were dried over $MgSO_4$, concentrated by rotary evaporator, and chromatographed on $SiO_2$ using 50% hexanes in EtOAc then pure EtOAC to give 336 mg (50%) of 42c. MS found: $(M+H)^+=308$.

(d) 42c (60 mg, 0.20 mmol) was treated with 1 mL of 50% TFA in DCM for 1 h. The reaction was concentrated by rotary evaporator and then coupled with Core C 60 mg, 0.20 mmol) using General Coupling Method B. The product was purified by HPLC to give 33 mg (33%) of the desired product 42. MS found: $(M+H)^+=499$.

Example 43

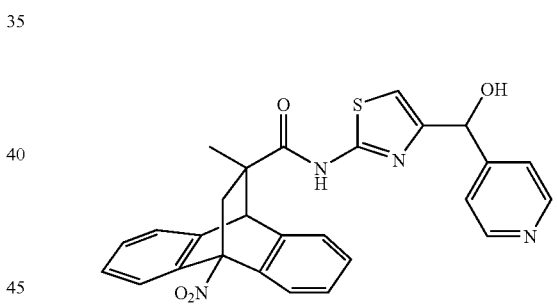

(a) To a solution commercially available 4-iodopyridine (0.82 g, 4.0 mmol) in 10 mL of THF at 0 C was added a 2M solution of EtMgCl in THF (2.0 mL, 4.0 mmol) dropwise. After 1 h, added a solution of 42b (456 mg, 2.0 mmol) in 5 mL of THF. The reaction was allowed to warm to rt and stirred at for 1 hr. The reaction was quenched with water and extracted 2×EtOAC. The EtOAc extracts were dried over $MgSO_4$, concentrated by rotary evaporator, and chromatographed on $SiO_2$ using 50% hexanes in EtOAc then pure EtOAC to give 138 mg (22%) of 43a. MS found: $(M+H)^+=308$.

(b) 43a (60 mg, 0.20 mmol) was treated with 1 mL of 50% TFA in DCM for 1 h. The reaction was concentrated by rotary evaporator and then coupled with Core C (60 mg, 0.20 mmol) using General Coupling Method B. The product was purified by HPLC to give 43 mg (43%) of the desired product 43. MS found: $(M+H)^+=499$.

Example 44

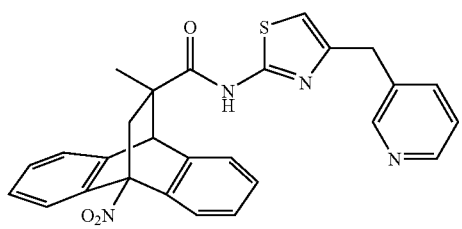

(a) To a solution of 42c (230 mg, 1.0 mmol) in 10 mL of THF and 5 mL of 1N HCl was added 10% Pd/C (3.0 g) all at once. The mixture was hydrogenated using a Parr apparatus at 50 psi of hydrogen overnight. Added more Pd/C (1.0 g) and repeated. The The reaction mixture was filtered and concentrated by rotary evaporator. The residue was dissolved in EtOAc and washed with sat NaHCO$_3$. The EtOAc extracts were dried over MgSO$_4$, filtered, concentrated by rotary evaporator, and chromatographed on SiO$_2$ using 50% hexanes in EtOAc then pure EtOAC to give 20 mg (7%) of 44a. MS found: (M+H)$^+$=292.

(b) 42c (20 mg, 0.07 mmol) was treated with 1 mL of 50% TFA in DCM for 1 h. The reaction was concentrated by rotary evaporator and then coupled with Core C (37 mg, 0.12 mmol) using General Coupling Method B. The product was purified by HPLC to give 22 mg (54%) of the desired product 44. MS found: (M+H)$^+$=483.

Example 45

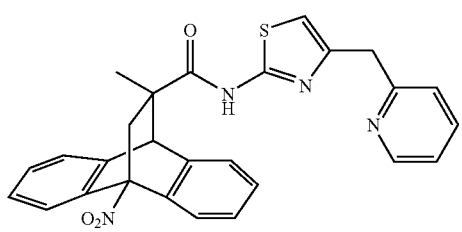

(a) To a solution of 1-chloro-3-(pyridine-2-yl)propan-2-one (200 mg, 1.18 mmol, prepared as detailed in *Chem. Heterocyclic Compounds*, 1986, 22, 633-639) in 10 mL of EtOH was added thiourea (90 mg, 1.18 mmol) all at once. The reaction was heated at reflux for 4 hr. The reaction was diluted with EtOAc and washed with sat NaHCO$_3$. The EtOAc extracts were dried over MgSO$_4$ and concentrated by rotary evaporator to give 190 g (84%) of pure aminothiazole 45a. MS found: (M+H)$^+$=192.

(b) 45a (61 mg, 0.32 mmol) was coupled with Core C (50 mg, 0.16 nunol) using General Coupling Method B. The product was purified by HPLC to give 35 mg (18%) of the desired product 45. MS found: (M+H)$^+$=483.

Example 46

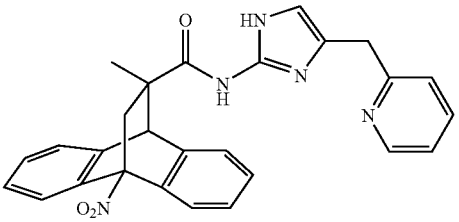

(a) A solution of 1-chloro-3-(pyridine-2-yl)propan-2-one (500 mg, 2.95 mmol, prepared as detailed in *Chem. Heterocyclic Compounds*, 1986, 22, 633-639) in 5 mL of DMF was added dropwise to a solution of commercially available acetylguanidine (606 mg, 6.0 mmol) in 5 mL of DMF at 0 C. The reaction was allowed to slowly warm to rt and stirred for 24 hr. The reaction was diluted with brine and extracted 2×EtOAc. The EtOAc extracts were dried over MgSO$_4$. The solution was filtered, concentrated by rotary evaporator, and the residue was purified by HPLC to give 77 mg (12%) of 46a. MS found: (M+H)$^+$=217.

(b) 46a (32 mg, 0.15 mmol) was heated at 80 C in a solution of 1 mL of conc HCl and 2 mL of MeOH for 1 hr. The reaction mixture was concentrated by rotary evaporator to give a quantitative yield of 45b as the HCl salt. MS found: (M+H)$^+$=175.

(c) 46b (35 mg, 0.16 mmol) was coupled with Core C (50 mg, 0.16 mmol) using General Coupling Method B. The product was purified by HPLC to give 1.1 mg (1.1%) of the desired product 46. MS found: (M+H)$^+$=445.

Example 47

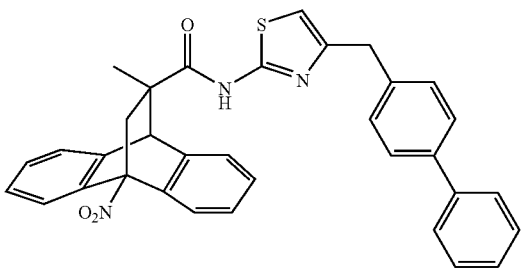

A Smith Process vial was charged with 37 (60 mg, 0.107 mmol), phenylboronic acid (26 mg, 0.21 mmol), tetrakis (triphenylphosphine)palladium(0) (12 mg, 0.01 mmol), 0.2 mL of 2M K$_2$CO$_3$, and 2.5 mL of DMF. The reaction mixture was degassed by bubbling nitrogen through for 15 min, then sealed and exposed to microwave irradiation for 30 min at 150 C. The reaction was cooled, filtered and purified by HPLC to give 6 mg of 47. MS found: (M+H)$^+$=558.

Example 48

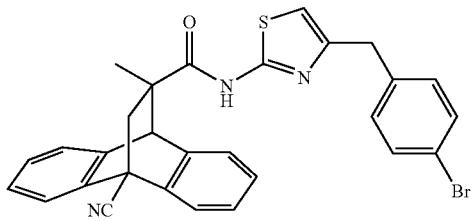

37b (2.0 g, 7.2 mmol) was coupled with Core B (2.1 mg, 7.4 mmol) using General Coupling Method A. The product was chromatographed on SiO$_2$ using 20% hexanes in DCM to give 1.8 g (46%) of 48. MS found: (M+H)$^+$=541.

Example 49

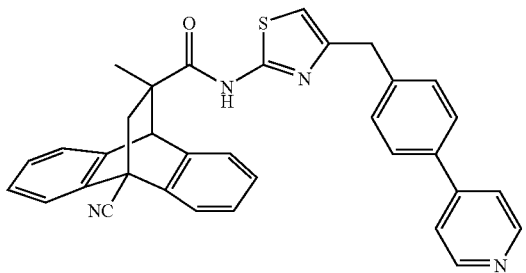

A Smith Process vial was charged with 48 (100 mg, 0.178 mmol), 4-pyridineboronic acid (72 mg, 0.35 mmol), tetrakis(triphenylphosphine)palladium(0) (21 mg, 0.018 mmol), 0.2 mL of 2M K$_2$CO$_3$, and 2.5 mL of DMF. The reaction mixture was degassed by bubbling nitrogen through for 15 min, then sealed and exposed to microwave irradiation for 30 min at 150 C. The reaction was cooled, filtered and purified by HPLC to give 6 mg of 49. MS found: (M+H)$^+$=539.

Example 50

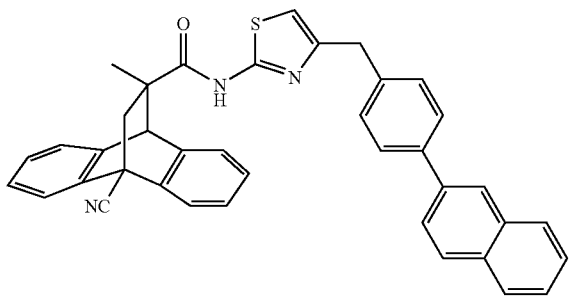

A Smith Process vial was charged with 48 (100 mg, 0.178 mmol), naphthalen-2-ylboronic acid (60 mg, 0.35 mmol), tetrakis(triphenylphosphine)palladium(0) (21 mg, 0.018 mmol), 0.2 mL of 2M K$_2$CO$_3$, and 2.5 mL of DMF. The reaction mixture was degassed by bubbling nitrogen through for 15 min, then sealed and exposed to microwave irradiation for 30 min at 150 C. The reaction was cooled, filtered and purified by HPLC to give 47 mg (45%) of 50. MS found: (M+H)$^+$=588.

Example 51

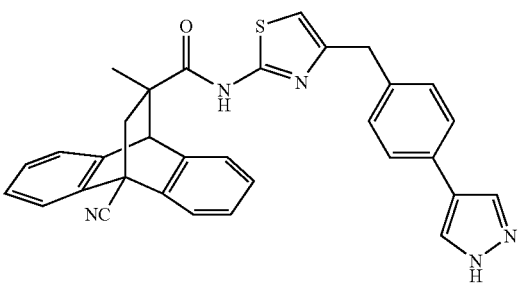

A Smith Process vial was charged with 48 (100 mg, 0.178 mmol), 4-(4,4,5,5-tetramethyl-1,3,2-dioxaborolan-2-yl)-1H-pyrazol (48 mg, 0.25 mmol), tetrakis(triphenylphosphine)palladium(0) (21 mg, 0.018 mmol), 0.2 mL of 2M K$_2$CO$_3$, and 2.5 mL of DMF. The reaction mixture was degassed by bubbling nitrogen through for 15 min, then sealed and exposed to microwave irradiation for 30 min at 150 C. The reaction was cooled, filtered and purified by HPLC to give 48 mg (42%) of 51. MS found: (M+H)$^+$=528.

Example 52

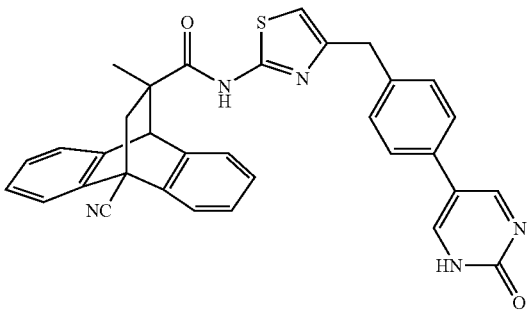

A Smith Process vial was charged with 48 (100 mg, 0.178 mmol), 2-oxo-1,2-dihydropyrimidin-5-ylboronic acid (49 mg, 0.35 mmol), tetrakis(triphenylphosphine)palladium(0) (21 mg, 0.018 mmol), 0.2 mL of 2M K$_2$CO$_3$, and 2.5 mL of DMF. The reaction mixture was degassed by bubbling nitrogen through for 15 min, then sealed and exposed to microwave irradiation for 30 min at 150 C. The reaction was cooled, filtered and purified by HPLC to give 44 mg (44%) of 52. MS found: (M+H)$^+$=556.

Example 53

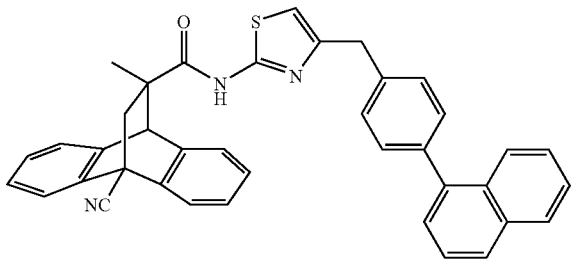

A Smith Process vial was charged with 48 (100 mg, 0.178 mmol), naphthalen-1-ylboronic acid (60 mg, 0.35 mmol), tetrakis(triphenylphosphine)palladium(0) (21 mg, 0.018 mmol), 0.2 mL of 2M $K_2CO_3$, and 2.5 mL of DMF. The reaction mixture was degassed by bubbling nitrogen through for 15 min, then sealed and exposed to microwave irradiation for 30 min at 150 C. The reaction was cooled, filtered and purified by HPLC to give 58 mg (56%) of 53. MS found: $(M+H)^+=588$.

Example 54

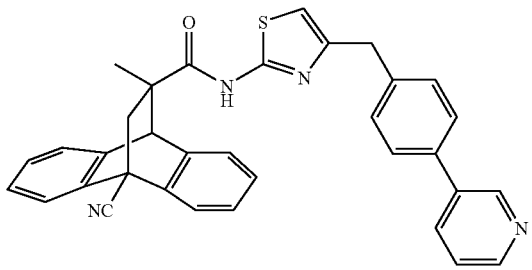

A Smith Process vial was charged with 48 (54 mg, 0.10 mmol), 3-pyridineboronic acid (25 mg, 0.20 mmol), tetrakis(triphenylphosphine)palladium(0) (12 mg, 0.010 mmol), 0.1 mL of 2M $K_2CO_3$, and 2.5 mL of DMF. The reaction mixture was degassed by bubbling nitrogen through for 15 min, then sealed and exposed to microwave irradiation for 30 min at 150 C. The reaction was cooled, filtered and purified by HPLC to give 9 mg (17%) of 54. MS found: $(M+H)^+=539$.

Example 55

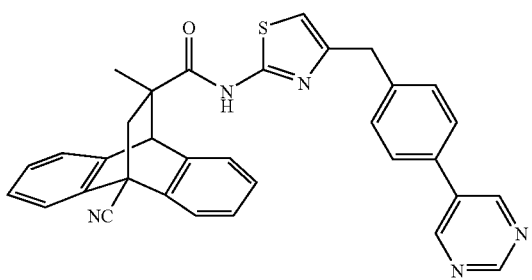

A Smith Process vial was charged with 48 (54 mg, 0.10 mmol), pyrimidin-5-ylboronic acid (25 mg, 0.20 mmol), tetrakis(triphenylphosphine)palladium(0) (12 mg, 0.010 mmol), 0.1 mL of 2M $K_2CO_3$, and 2.5 mL of DMF. The reaction mixture was degassed by bubbling nitrogen through for 15 min, then sealed and exposed to microwave irradiation for 30 min at 150 C. The reaction was cooled, filtered and purified by HPLC to give 18 mg (33%) of 55. MS found: $(M+H)^+=540$.

Example 56

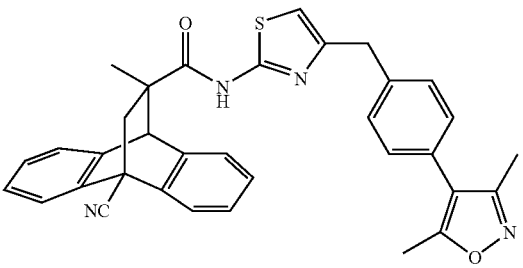

A Smith Process vial was charged with 48 (54 mg, 0.10 mmol), 3,5-dimethyl-4-(4,4,5,5-tetramethyl-1,3,2-dioxaborolan-2-yl)isoxazole (28 mg, 0.20 mmol), tetrakis(triphenylphosphine)palladium(0) (12 mg, 0.010 mmol), 0.1 mL of 2M $K_2CO_3$, and 2.5 mL of DMF. The reaction mixture was degassed by bubbling nitrogen through for 15 min, then sealed and exposed to microwave irradiation for 30 min at 150 C. The reaction was cooled, filtered and purified by HPLC to give 35 mg (63%) of 56. MS found: (M+H)+557.

Example 57

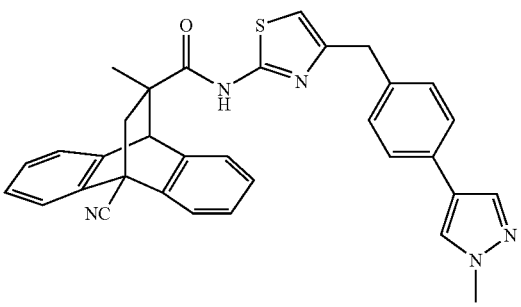

A Smith Process vial was charged with 48 (54 mg, 0.10 mmol), 1-methyl-4-(4,4,5,5-tetramethyl-1,3,2-dioxaborolan-2-yl)-1H-pyrazole (42 mg, 0.20 mmol), tetrakis(triphenylphosphine)palladium(0) (12 mg, 0.010 mmol), 0.1 mL of 2M $K_2CO_3$, and 2.5 mL of DMF. The reaction mixture was degassed by bubbling nitrogen through for 15 min, then sealed and exposed to microwave irradiation for 30 min at 150 C. The reaction was cooled, filtered and purified by HPLC to give 18 mg (33%) of 57. MS found: $(M+H)^+=542$.

Example 58

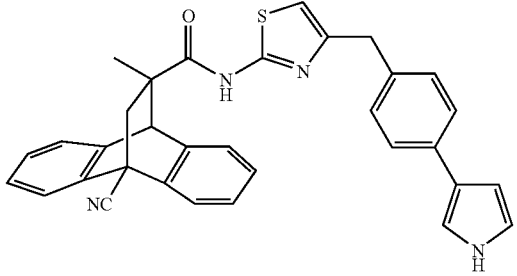

A Smith Process vial was charged with 48 (54 mg, 0.10 mmol), 3-(4,4,5,5-tetramethyl-1,3,2-dioxaborolan-2-yl)-1-(triisopropylsilyl)-1H-pyrrole (53 mg, 0.20 mmol), tetrakis(triphenylphosphine)palladium(0) (12 mg, 0.010 mmol), 0.1 mL of 2M $K_2CO_3$, and 2.5 mL of DMF. The reaction mixture was degassed by bubbling nitrogen through for 15 min, then sealed and exposed to microwave irradiation for 30 min at 150 C. The reaction was cooled, filtered and purified by HPLC to give 17 mg (32%) of 58. MS found: $(M+H)^+=527$.

Example 59

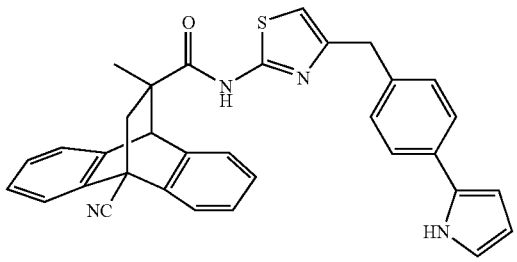

A Smith Process vial was charged with 48 (54 mg, 0.10 mmol), 1-(tert-butoxycarbonyl)-1H-pyrrol-2-ylboronic acid (42 mg, 0.20 mmol), tetrakis(triphenylphosphine)palladium(0) (12 mg, 0.010 mmol), 0.1 mL of 2M $K_2CO_3$, and 2.5 mL of DMF. The reaction mixture was degassed by bubbling nitrogen through for 15 min, then sealed and exposed to microwave irradiation for 30 min at 150 C. The reaction was cooled, filtered and purified by HPLC to give 9 mg (17%) of 59. MS found: $(M+H)^+=527$.

Example 60

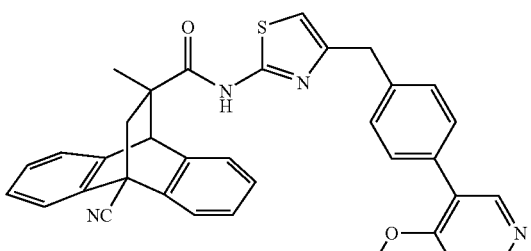

A Smith Process vial was charged with 48 (54 mg, 0.10 mmol), 4-methoxypyridin-3-ylboronic acid (30 mg, 0.20 mmol), tetrakis(triphenylphosphine)palladium(0) (12 mg, 0.010 mmol), 0.1 mL of 2M $K_2CO_3$, and 2.5 mL of DMF. The reaction mixture was degassed by bubbling nitrogen through for 15 min, then sealed and exposed to microwave irradiation for 30 min at 150 C. The reaction was cooled, filtered and purified by HPLC to give 6 mg (10%) of 60. MS found: $(M+H)^+=569$.

Example 61

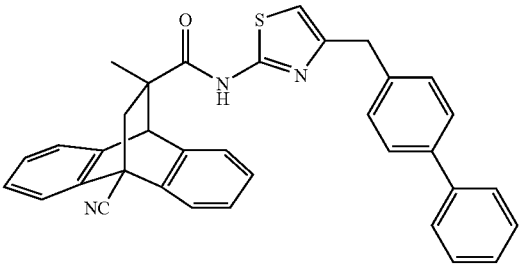

A Smith Process vial was charged with 48 (54 mg, 0.10 mmol), phenylboronic acid (25 mg, 0.20 mmol), tetrakis(triphenylphosphine)palladium(0) (12 mg, 0.010 mmol), 0.1 mL of 2M $K_2CO_3$, and 2.5 mL of DMF. The reaction mixture was degassed by bubbling nitrogen through for 15 min, then sealed and exposed to microwave irradiation for 30 min at 150 C. The reaction was cooled, filtered and purified by HPLC to give 23 mg (43%) of 61. MS found: $(M+H)^+=538$.

Example 62

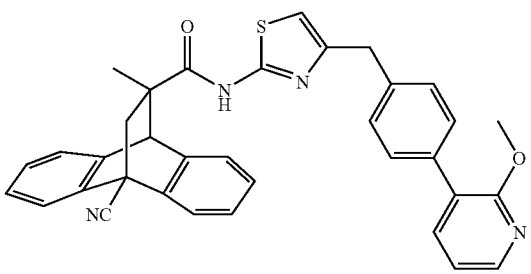

A Smith Process vial was charged with 48 (54 mg, 0.10 mmol), 2-methoxypyridin-3-ylboronic acid (30 mg, 0.20 mmol), tetrakis(triphenylphosphine)palladium(0) (12 mg, 0.010 mmol), 0.1 mL of 2M $K_2CO_3$, and 2.5 mL of DMF. The reaction mixture was degassed by bubbling nitrogen through for 15 min, then sealed and exposed to microwave irradiation for 30 min at 150 C. The reaction was cooled, filtered and purified by HPLC to give 18 mg (33%) of 62. MS found: $(M+H)^+=569$.

Example 63

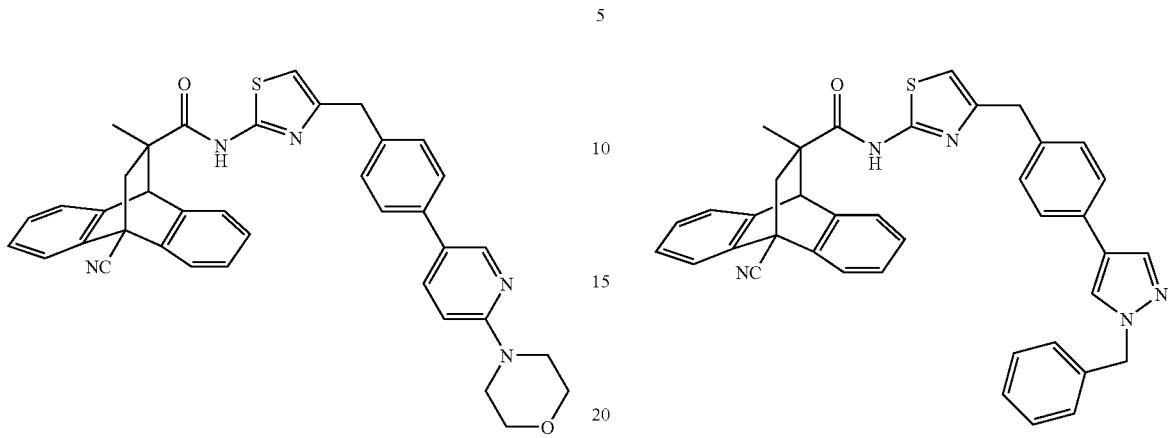

A Smith Process vial was charged with 48 (54 mg, 0.10 mmol), 4-(6-(4,4,5,5-tetramethyl-1,3,2-dioxaborolan-2-yl)pyridin-3-yl)morpholine (58 mg, 0.20 mmol), tetrakis(triphenylphosphine)palladium(0) (12 mg, 0.010 mmol), 0.1 mL of 2M $K_2CO_3$, and 2.5 mL of DMF. The reaction mixture was degassed by bubbling nitrogen through for 15 min, then sealed and exposed to microwave irradiation for 30 min at 150 C. The reaction was cooled, filtered and purified by HPLC to give 30 mg (50%) of 63. MS found: $(M+H)^+=624$.

Example 64

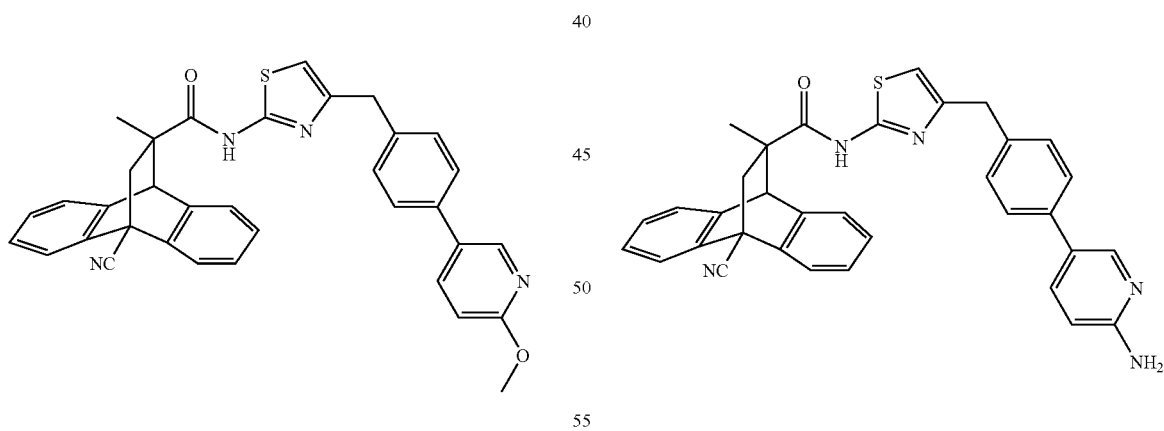

A Smith Process vial was charged with 48 (54 mg, 0.10 mmol), 6-methoxypyridin-3-ylboronic acid (30 mg, 0.20 mmol), tetrakis(triphenylphosphine)palladium(0) (12 mg, 0.010 mmol), 0.1 mL of 2M $K_2CO_3$, and 2.5 mL of DMF. The reaction mixture was degassed by bubbling nitrogen through for 15 min, then sealed and exposed to microwave irradiation for 30 min at 150 C. The reaction was cooled, filtered and purified by HPLC to give 35 mg (51%) of 64. MS found: $(M+H)^+=569$.

Example 65

A Smith Process vial was charged with 48 (54 mg, 0.10 mmol), 1-benzyl-4-(4,4,5,5-tetramethyl-1,3,2-dioxaborolan-2-yl)-1H-pyrazole (57 mg, 0.20 mmol), tetrakis(triphenylphosphine)palladium(0) (12 mg, 0.010 mmol), 0.1 mL of 2M $K_2CO_3$, and 2.5 mL of DMF. The reaction mixture was degassed by bubbling nitrogen through for 15 min, then sealed and exposed to microwave irradiation for 30 min at 150 C. The reaction was cooled, filtered and purified by HPLC to give 26 mg (42%) of 65. MS found: $(M+H)^+=618$.

Example 66

A Smith Process vial was charged with 48 (54 mg, 0.10 mmol), 35-(4,4,5,5-tetramethyl-1,3,2-dioxaborolan-2-yl)pyridin-2-amine (44 mg, 0.20 mmol), tetrakis(triphenylphosphine)palladium(0) (12 mg, 0.010 mmol), 0.1 mL of 2M $K_2CO_3$, and 2.5 mL of DMF. The reaction mixture was degassed by bubbling nitrogen through for 15 min, then sealed and exposed to microwave irradiation for 30 min at 150 C. The reaction was cooled, filtered and purified by HPLC to give 6 mg (9%) of 66. MS found: $(M+H)^+=554$.

Example 67

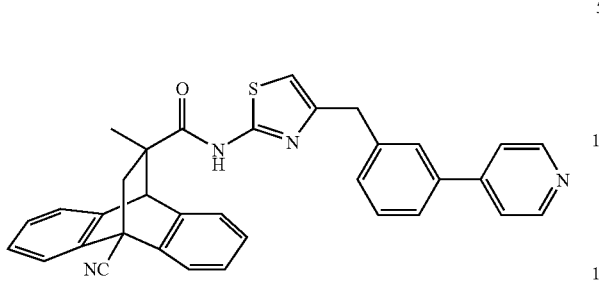

(a) 40b (560 mg, 2.1 mmol) was coupled with Core A (579 mg, 2.0 mmol) using General Coupling Method B. The reaction was diluted with brine, and extracted 2×EtOAc. The EtOAc extracts were dried over MgSO$_4$. The solution was filtered, concentrated by rotary evaporator, and chromatographed on SiO$_2$ using 25% EtOAc in hexanes to give 682 mg (61%) of 67a. MS found: (M+H)$^+$=561.

(b) A Smith Process vial was charged with 67a (54 mg, 0.10 mmol), 4-pyridineboronic acid (25 mg, 0.20 mmol), tetrakis(triphenylphosphine)palladium(0) (12 mg, 0.010 mmol), 0.1 mL of 2M K$_2$CO$_3$, and 2.5 mL of DMF. The reaction mixture was degassed by bubbling nitrogen through for 15 min, then sealed and exposed to microwave irradiation for 30 min at 150 C. The reaction was cooled, filtered and purified by HPLC to give 26 mg (49%) of 67. MS found: (M+H)$^+$=539.

Example 68

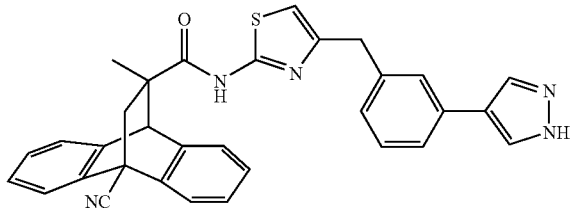

A Smith Process vial was charged with 67a (54 mg, 0.10 mmol), 4-(4,4,5,5-tetramethyl-1,3,2-dioxaborolan-2-yl)-1H-pyrazol (38 mg, 0.20 mmol), tetrakis(triphenylphosphine)palladium(0) (12 mg, 0.010 mmol), 0.1 mL of 2M K$_2$CO$_3$, and 2.5 mL of DMF. The reaction mixture was degassed by bubbling nitrogen through for 15 min, then sealed and exposed to microwave irradiation for 30 min at 150 C. The reaction was cooled, filtered and purified by HPLC to give 26 mg (50%) of 68. MS found: (M+H)$^+$=528.

Example 69

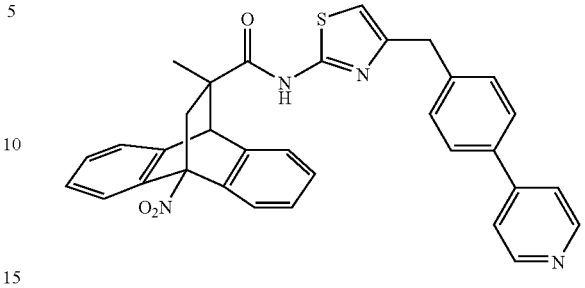

(a) Charged a flask with 37b (8.07 g, 30 mmol), 4-pyridineboronic acid (6.1 g, 50 mmol), tetrakis(triphenylphosphine)palladium(0) (3.5 g, 3.0 mmol), 30 mL of 2M K$_2$CO$_3$, and 200 mL of DMF. The reaction mixture was degassed by bubbling nitrogen through for 15 min then heated at 100 C overnight. The reaction mixture was diluted in EtOAc and extracted 3×1N HCl. The aqueous extracts were basified with 1N NaOH and then allowed to stand in refrigerator for 2 hr. Solid was collected and dried in vacuo to give 5.4 g (68%) of pure 69a. MS found: (M+H)$^+$=268.

(b) 69a (30 mg, 0.11 mmol) was coupled with Core C (50 mg, 0.16 mmol) using General Coupling Method B. The product was chromatographed on SiO$_2$ using 50% hexanes in EtOAC to give 16 mg (29%) of 69. MS found: (M+H)$^+$=559.

Example 70

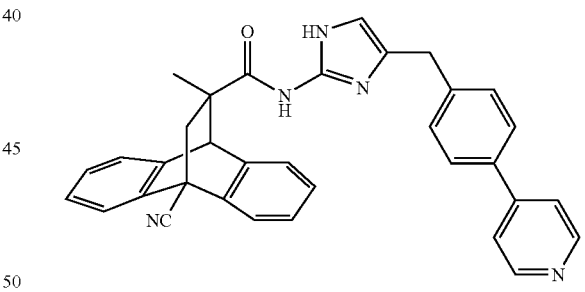

(a) Charged a flask with 38b (85 mg, 0.30 mmol), 4-(4,4,5,5-tetramethyl-1,3,2-dioxaborolan-2-yl)pyridine (92 mg, 0.45 mmol), tetrakis(triphenylphosphine)palladium(0) (35 mg, 0.030 mmol), 0.2 mL of 2M K$_2$CO$_3$, and 3 mL of DMF. The reaction mixture was degassed by bubbling nitrogen through for 15 min, then sealed and exposed to microwave irradiation for 30 min at 150 C. The reaction was cooled, filtered and purified by HPLC to give 53 mg (49%) of 70a. MS found: (M+H)$^+$–251.

(b) 70a (53 mg, 0.15 mmol) was coupled with Core B (50 mg, 0.17 mmol) using General Coupling Method A. The product was purified by HPLC to give 8 mg (1%) of 70. MS found: (M+H)$^+$=522.

Example 71

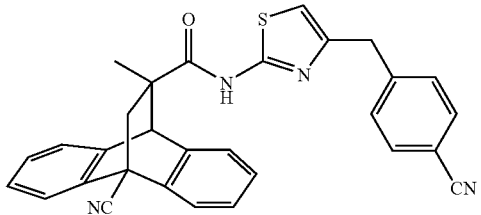

(a) Charged a flask with 37b (3.0 g, 11.1 mmol), zinc cyanide (870 mg, 7.4 mmol), zinc (121 mg, 1.85 mmol), tris(dibenzylideneacetone)dipalladium(0) (257 mg, 0.28 mmol), 1,1'-bis(diphenylphosphino)ferrocene (310 mg, 0.56 mmol), and 50 mL of DMA. The reaction mixture was heated overnight at 150 C. The reaction was diluted with brine, and extracted 2×EtOAC. The EtOAc extracts were dried over $MgSO_4$. The solution was filtered, concentrated by rotary evaporator, and chromatographed on $SiO_2$ using EtOAc to give 1.3 g (54%) of 71a. MS found: $(M+H)^+=216$.

(b) 71a (57 mg, 0.17 mmol) was coupled with Core B (50 mg, 0.17 mmol) using General Coupling Method A. The product was purified by HPLC to give 25 mg (30%) of 71. MS found: $(M+H)^+=487$.

Example 72

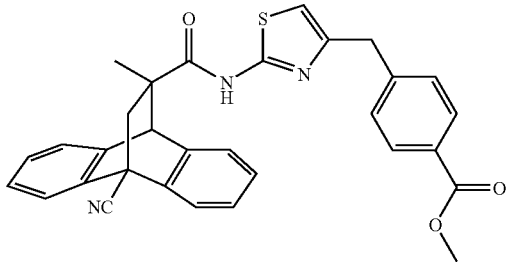

(a) 37b (5.2 g, 19.3 mmol) was heated in 20 mL of acetic anhydride for 2 h at 100 C. The reaction mixture was concentrated by rotary evaporator, and the residue was triturated in EtOAc/hexanes. The resulting solid was collected and dried in vacuo give 3.38 g (49%) of the acetylthiazole 72a. MS found: $(M+H)^+=312$.

(b) Charged a flask with 72a (257 mg, 0.83 mmol), zinc cyanide (58 mg, 0.50 mmol), zinc (7 mg, 0.1 mmol), tris(dibenzylideneacetone)dipalladium(0) (16 mg, 0.017 mmol), 1,1'-bis(diphenylphosphino)ferrocene (19 mg, 0.034 mmol), and 2 mL of DMF. The reaction mixture was heated overnight at 150 C. The reaction was diluted with brine, and extracted 2×EtOAc. The EtOAc extracts were dried over $MgSO_4$. The solution was filtered, concentrated by rotary evaporator, and chromatographed on $SiO_2$ using 50% hexanes in EtOAc to give 93 mg (44%) of 72b. MS found: $(M+H)^+=258$.

(c) 72b (93 mg, 0.36 mmol) was heated at reflux in 10 mL of 6N HCl for 18 hr. The reaction mixture was concentrated by rotary evaporator. The crude residue was dissolved in 10 mL of MeOH and HCl gas was bubbled through for 15 min. The reaction was stirred for 1 hr at rt. The reaction mixture was concentrated by rotary evaporator to give 72c in quantitative yield. MS found: $(M+H)^+=249$.

(d) 72c (102 mg, 0.36 mmol) was coupled with Core B (50 mg, 0.17 mmol) using General Coupling Method A. The product was purified on $SiO_2$ using 66% hexanes in EtOAc to give 177 mg (95%) of 72. MS found: $(M+H)^+=520$.

Example 73

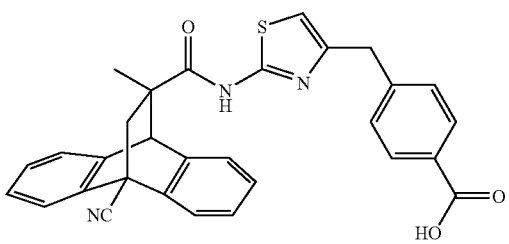

A solution of 72 (177 mg, 0.34 mmol) in 2 mL of MeOH and 1 mL of 1N NaOH was stirred at rt for 12 hr. The reaction mixture was diluted with water and acidified with conc HCl. The resulting solid was collected and dried in vacuo give 152 mg (88%) of 73. MS found: $(M+H)^+=506$.

Example 74

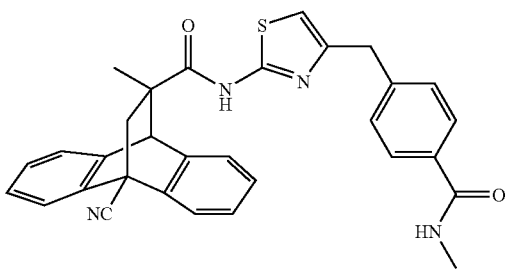

73 (30 mg, 0.060 mmol) was coupled with methylamine hydrochloride (7 mg, 0.10 mmol) using EDC, HOBt, $Et_3N$ conditions similar to those used in General Coupling Method B. The product was purified by HPLC to give 18 mg (58%) of 74. MS found: $(M+H)^+=519$.

Example 75

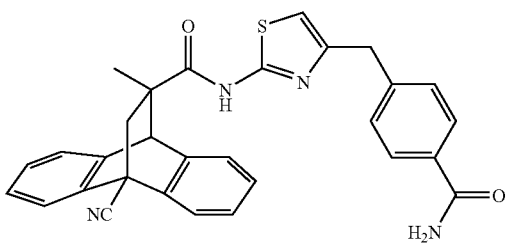

73 (30 mg, 0.060 mmol) was coupled with conc ammonium hydroxide (0.5 mL) using EDC, HOBt, $Et_3N$ conditions similar to those used in General Coupling Method B. The product was purified by HPLC to give 8 mg (27%) of 75. MS found: $(M+H)^+=505$.

Example 76

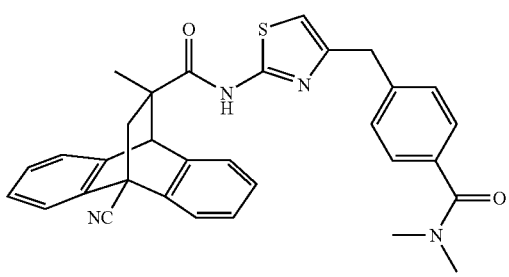

73 (30 mg, 0.060 mmol) was coupled with 2M dimethylamine in THF (0.05 mL, 0.10 mmol) using EDC, HOBt, Et$_3$N conditions similar to those used in General Coupling Method B. The product was purified by HPLC to give 17 mg (53%) of 76. MS found: (M+H)$^+$=533.

Example 77

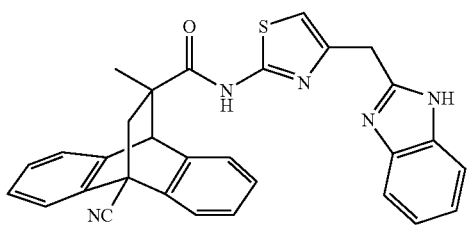

(a) 2-(2-(tert-butoxycarbonyl)thiazol-4-yl)acetic acid (824 mg, 3.2 mmol) which was prepared according to the method of Kim et. al. *Synlett*, 1999, 8, 1239-1240) was coupled with 1,2-phenylenediamine (345 mg, 3.2 mmol) using General Coupling Method B. The product was purified on SiO$_2$ using 33% hexanes in EtOAc to give 335 mg (30%) of 77a. MS found: (M+H)$^+$=349.

(b) 77a (330 mg, 0.95 mmol) was heated in 5 mL of glacial acetic acid for 2 h at 100 C. The reaction mixture was cooled and concentrated by rotary evaporator. The residue was diluted with sat NaHCO$_3$ and extracted 2×EtOAc. The EtOAc extracts were dried over MgSO$_4$, the solution was filtered, and concentrated by rotary evaporator to give 330 mg of 77b. MS found: (M+H)$^+$=331.

(c) 77b (52 mg, 0.16 mmol) was treated with a solution of 1 mL TFA and 1 mL DCM for 1 hr. The reaction mixture was concentrated by rotary evaporator and then coupled with Core A (50 mg, 0.16 mmol) using General Coupling Method B. The product was purified by HPLC to give 39 mg (49%) of 77. MS found: (M+H)$^+$=502.

Example 78

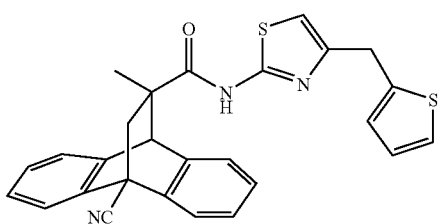

(a) 2-(thiophen-2-yl)acetyl chloride (391 mg, 2.4 mmol) was added to a freshly distilled solution of diazomethane in diethyl ether (~8 mmol, prepared from diazald) at 0 C. The reaction mixture was stirred for 30 min at 0 C then 2 mL of conc HCl was added. After stirred 30 min at 0 C, the reaction was allowed to warm to rt and stirred 1 hr. Quenched excess diazomethane with acetic acid. Diluted with EtOAc and washed with water and sat NaHCO$_3$. The EtOAc extracts were dried over MgSO$_4$ then solution was filtered and concentrated by rotary evaporator to give 78a which was taken to the next step without further purification.

(b) To a solution of 78a in 10 mL of EtOH was added thiourea (228 mg, 3.0 mmol) all at once. The reaction was heated at reflux for 4 hr. The reaction was diluted with water and extracted 2×EtOAC. The EtOAc extracts were dried over MgSO$_4$, filtered, and concentrated by rotary evaporator to give 460 mg (96%) of a 78b. MS found: (M+H)$^+$=197.

(c) 78b (48 mg, 0.25 mmol) was coupled with Core B (70 mg, 0.24 mmol) using General Coupling Method A. The product was purified by HPLC to give 52 mg (46%) of 78. MS found: (M+H)$^+$=468.

Example 79

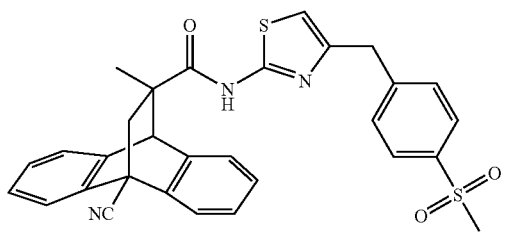

(a) 2-[4-(methylsulfonyl)phenyl]acetic acid (650 mg, 3.0 mmol) was heated at reflux in 5 mL of thionyl chloride for 1 hr. The reaction mixture was cooled and concentrated by rotary evaporator. The crude residue was dissolved in 10 mL of THF and then added to a freshly distilled solution of diazomethane in diethyl ether (~10 mmol, prepared from diazald) at 0 C. The reaction mixture was stirred for 30 min at 0 C then 2 mL of conc HCl was added. After stirring 30 min at 0 C, the reaction was allowed to warm to rt and stirred 1 hr. Quenched excess diazomethane with acetic acid. Diluted with EtOAc and washed with water and sat NaHCO$_3$. The EtOAc extracts were dried over MgSO$_4$ then solution was filtered and concentrated by rotary evaporator to give 79a which was taken to the next step without further purification.

(b) To a solution of 79a in 10 mL of EtOH was added thiourea (228 mg, 3.0 mmol) all at once. The reaction was heated at reflux for 4 hr. The reaction was diluted with water and extracted 2×EtOAC. The EtOAc extracts were dried over MgSO$_4$, filtered, and concentrated by rotary evaporator to give 630 mg (78%) of a 79b. MS found: (M+H)$^+$=269.

(c) 79b (27 mg, 0.10 mmol) was coupled with Core B (30 mg, 0.10 mmol) using General Coupling Method A. The product was purified by HPLC to give 36 mg (67%) of 79. MS found: (M+H)$^+$=540.

Example 80

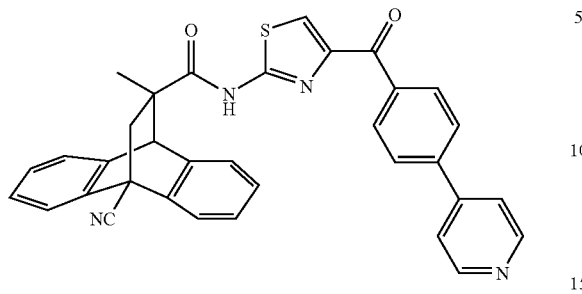

(a) To a solution of 4-bromophenylacetone in 20 mL of pyridine was added selenium dioxide and the reaction mixture was heated at 110 C for 1 hr. The reaction was cooled to 90 C and maintained at this temperature for 12 hr. The reaction mixture was diluted with EtOAc and filtered through a plug of Celite washing well with EtOAc. The filtrate was washed with 1N HCl. The EtOAc layer was separated and then extracted with 2×1N NaOH. The aqueous layer was acidified with conc HCl then extracted 2×EtOAc. The EtOAc extracts were dried over $MgSO_4$ then solution was filtered and concentrated by rotary evaporator to give 1.9 g of 80a.

(b) To a solution of 80a (1.9 g, 8.3 mmol) in 10 mL of DCM was added a solution of 2M oxalyl chloride in DCM (4.5 mL, 9 mmol) followed by 2 drops of DMF. The reaction was stirred for 1 hr. The reaction mixture was concentrated by rotary evaporator. The crude residue was dissolved in 10 mL of THF and then added to a freshly distilled solution of diazomethane in diethyl ether (~20 mmol, prepared from diazald) at 0 C. The reaction mixture was stirred for 30 min at 0 C then 2 mL of conc HCl was added. After stirred 30 min at 0 C, the reaction was allowed to warm to rt and stirred 1 hr. Quenched excess diazomethane with acetic acid. Diluted with EtOAc and washed with water and sat $NaHCO_3$. The EtOAc extracts were dried over $MgSO_4$ then solution was filtered and concentrated by rotary evaporator to give 80b which was taken to the next step without further purification.

(c) To a solution of 80b in 10 mL of EtOH was added thiourea (684 mg, 9.0 mmol) all at once. The reaction was heated at reflux for 4 hr. The reaction was diluted with water and extracted 2×EtOAC. The EtOAc extracts were dried over $MgSO_4$, filtered, and concentrated by rotary evaporator. The product was purified on $SiO_2$ using 50% hexanes in EtOAc to give 410 mg (17%) of 80c. MS found: $(M+H)^+=284$.

(d) 80c (115 mg, 0.41 mmol) was coupled with Core B (122 mg, 0.42 mmol) using General Coupling Method A. The product was purified on $SiO_2$ using 75% hexanes in EtOAc to give 182 mg (80%) of 80d. MS found: $(M+H)^+=555$.

(e) A Smith Process vial was charged with 80d (56 mg, 0.10 mmol), 4-pyridineboronic acid (25 mg, 0.20 mmol), tetrakis(triphenylphosphine)palladium(0) (12 mg, 0.010 mmol), 0.1 mL of 2M $K_2CO_3$, and 2.5 mL of DMF. The reaction mixture was degassed by bubbling nitrogen through for 15 min, then sealed and exposed to microwave irradiation for 30 min at 150 C. The reaction was cooled, filtered and purified by HPLC to give 8 mg (14%) of 80. MS found: $(M+H)^+=553$.

Example 81

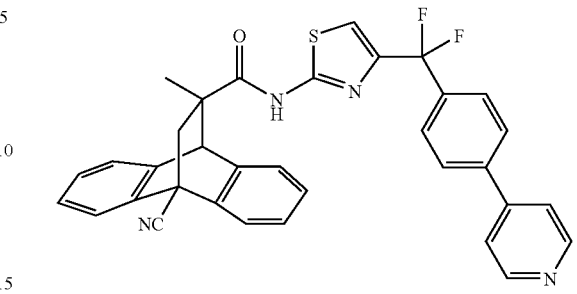

(a) A solution of 80a (3.5 g, 17.6 mmol) in 10 mL of THF was added to a freshly distilled solution of diazomethane in diethyl ether (~20 mmol, prepared from diazald) at 0 C. The reaction was allowed to warm to rt and stirred 1 hr. Quenched excess diazomethane with acetic acid. Diluted with diethyl ether and washed with water and 1N NaOH. The ether extracts were dried over $MgSO_4$ then solution was filtered and concentrated by rotary evaporator to give 1.8 g 81a. MS found: $(M+H)^+=244$.

(b) To a solution of 81a (1.8 g, 7.4 mmol) in 10 mL of DCM was added DeoxoFluor™ (4.0 mL, mmol) all at once. The reaction was stirred at rt for 12 hr. The reaction was diluted with DCM and washed with 1N HCl. The DCM extracts were dried over $MgSO_4$, filtered, and concentrated by rotary evaporator. The crude product was treated with 40 mL of 1:1 1N NaOH/MeOH for 2 hr. The reaction mixture was diluted with water and washed with EtOAc. The aqueous layer was acidified with conc HCl and extracted 2×EtOAc. The EtOAc extracts were dried over $MgSO_4$, filtered, and concentrated by rotary evaporator to give 1.6 g of 81b. MS found: $(M+H)^+=252$.

(c) 81b (1.6 g, 6.37 mmol) was heated at reflux in 20 mL of thionyl chloride for 1 hr. The reaction mixture was cooled and concentrated by rotary evaporator. The crude residue was dissolved in 10 mL of THF and then added to a freshly distilled solution of diazomethane in diethyl ether (~15 mmol, prepared from diazald) at 0 C. The reaction mixture was stirred for 30 min at 0 C then 2 mL of conc HCl was added. After stirred 30 min at 0 C, the reaction was allowed to warm to rt and stirred 1 hr. Quenched excess diazomethane with acetic acid. Diluted with EtOAc and washed with water and sat $NaHCO_3$. The EtOAc extracts were dried over $MgSO_4$ then solution was filtered and concentrated by rotary evaporator to give 81c which was taken to the next step without further purification.

(d) To a solution of 81c in 20 mL of EtOH was added thiourea (532 mg, 7.0 mmol) all at once. The reaction was heated at reflux for 4 hr. The reaction was diluted with water and extracted 2×EtOAC. The EtOAc extracts were dried over $MgSO_4$, filtered, and concentrated by rotary evaporator. To remove unwanted methyl ester the residue was treated with 10 mL of 1:1 1N NaOH/MeOH for 2 hr. The reaction mixture was diluted with water and extracted 2×EtOAC. The EtOAc extracts were dried over $MgSO_4$ then solution was filtered and concentrated by rotary evaporator to give 390 mg (21%) of a 81d. MS found: $(M+H)^+=306$.

(e) 81d (390 mg, 1.28 mmol) was coupled with Core A (430 mg, 1.48 mmol) using General Coupling Method B.

The product was purified on SiO$_2$ using 90% hexanes in EtOAc to give 140 mg (19%) of 81e. MS found: (M+H)$^+$=577.

(f) A Smith Process vial was charged with 81e (140 mg, 0.24 mmol), 4-pyridineboronic acid (122 mg, 0.48 mmol), tetrakis(triphenylphosphine)palladium(0) (28 mg, 0.024 mmol), 0.24 mL of 2M K$_2$CO$_3$, and 2.5 mL of DMF. The reaction mixture was degassed by bubbling nitrogen through for 15 min, then sealed and exposed to microwave irradiation for 30 min at 150 C. The reaction was cooled, filtered and purified by HPLC to give 10 mg (6%) of 81. MS found: (M+H)$^+$=575.

Example 82

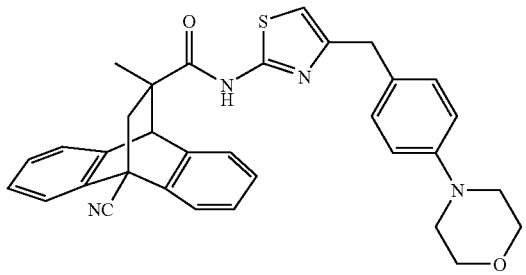

A Smith Process vial was charged with 48 (54 mg, 0.10 mmol), morpholine (35 mg, 0.40 mmol), palladium(II) acetate (2.3 mg, 0.010 mmol), 2-(di-t-butylphsphino)biphenyl (6 mg, 0.02 mmol), 0.1 mL of 2M K$_2$CO$_3$, and 2.5 mL of DMF. The reaction mixture was degassed by bubbling nitrogen through for 15 min, then sealed and exposed to microwave irradiation for 1 hr at 150 C. The reaction was cooled, filtered and purified by HPLC to give 7 mg (13%) of 82. MS found: (M+H)$^+$=547.

Example 83

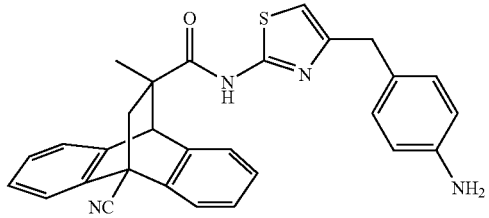

(a) 39b (500 mg, 2.2 mmol) was coupled with Core B (619 mg, 2.12 mmol) using General Coupling Method A. The reaction was diluted with brine, and extracted 2×EtOAC. The EtOAc extracts were dried over MgSO$_4$. The solution was filtered, concentrated by rotary evaporator, and chromatographed on SiO$_2$ using 66% hexanes in EtOAc to give 791 mg (71%) of 83a. MS found: (M+H)$^+$=258.

(b) To a solution of 83a (790 mg, 1.56 mmol) in 20 mL of EtOH was added tin(II) chloride (1.14 g, 6.0 mmol) all at once. The reaction was heated at reflux for 18 hr. The reaction was diluted with EtOAc and washed with 2×dilute aq. KF solution concentrated EtOAc extracts were dried over MgSO$_4$. The solution was filtered, concentrated by rotary evaporator, and 50 mg of the crude residue were purified by HPLC to give 24 mg of 83. MS found: (M+H)$^+$=477.

Example 84

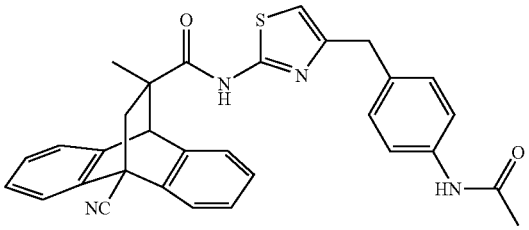

To a solution of 83 (40 mg, 0.3 mmol) in 5 mL of DCM was added 0.5 mL of acetic anhydride. The reaction mixture was heated at reflux for 15 min. The reaction was concentrated by rotary evaporator, and the product was purified by HPLC to give 35 mg (81%) of the desired product 84. MS found: (M+H)$^+$=519.

Example 85

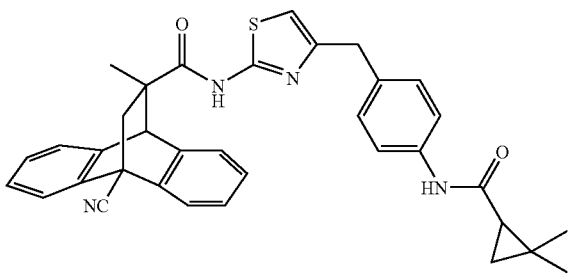

83 (48 mg, 0.10 mmol) was coupled with 2,2-dimethylcyclopropanecarboxylic acid (14 mg, 0.12 mmol) using EDC, HOBt, Et$_3$N conditions similar to those used in General Coupling Method B. The product was purified by HPLC to give 35 mg (61%) of 85. MS found: (M+H)$^+$=573.

Example 86

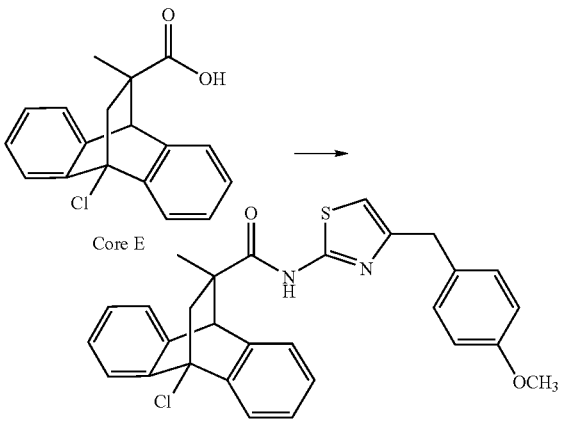

Example 86

Following the general coupling method B, to a solution of the acid, Core E (34 mg, 0.114 mmol) in acetonitrile (2 ml) were added 1-hydroxybenzo-triazole (23 mg, 0.17 mmol), and 1-[3-(dimethylamino)propyl]-3-ethylcarbodiimide hydrochloride (33 mg, 0.17 mmol). After stirring for 10 minutes, (4-(4-methoxybenzyl)thiazol-2-amine (25 mg, 0.114 mmol) was added followed by addition of diisopropylethylamine (44 mg, 0.063 ml, 0.342 mmol). The reaction was heated at 85 C for 16 hr. The product mixture was concentrated and purified by HPLC to give the title compound of Example 86 as a while solid (33.8 mg, 0.068 mmol, 59% yield). LC/MS m/z 501.24 (M+H)$^+$; HPLC (Column: Shimadzu VP-0DS, C-18 Ballistic; 4.6×50 mm,.4.0 mL/min. flow rate, 220 nm detection wavelength; 10-90% aq CH3OH/0.1% H3PO4, 4.0 min. gradient w/1 min. hold, same for compounds described below unless noted) Rt: 4.353 min. 100% purity.

Examples 87 to 91

In a similar manner to Example 86, Examples 87-91 were prepared via the coupling reactions of the appropriate acids (Cores F, G and H) and (4-(4-methoxybenzyl)thiazol-2-amine (in Example 10) or 4-(4-(pyridin-4-yl)benzyl)thiazol-2-amine (in Example 49).

| Example No. | Structure | HPLC Rt Minutes | MS m/z [(M + 1)] | Acid Cores |
|---|---|---|---|---|
| 87 | 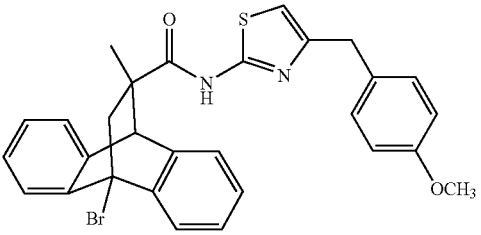 | 4.385 | 545.0 | 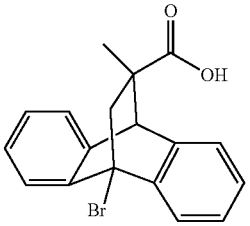<br>Core F |
| 88 | 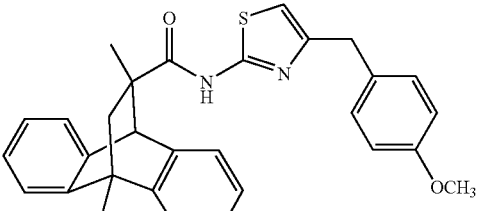 | 4.260 | 481.3 | 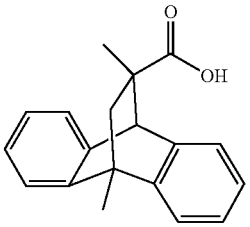<br>Core G |
| 89 | 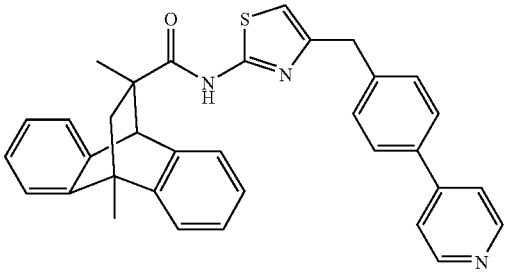 | 3.408 | 528.3 | 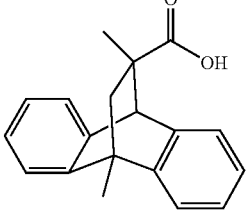<br>Core G |
| 90 | 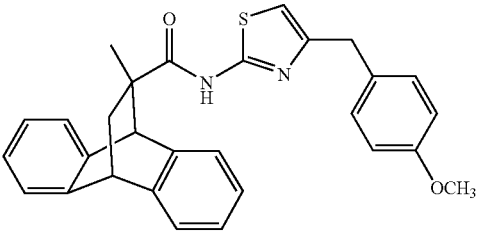 | 4.132 | 467.3 | 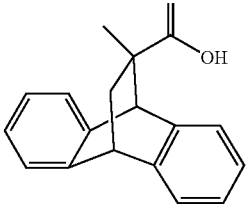<br>Core H |

| Example No. | Structure | HPLC Rt Minutes | MS m/z [(M + 1)] | Acid Cores |
|---|---|---|---|---|
| 91 | 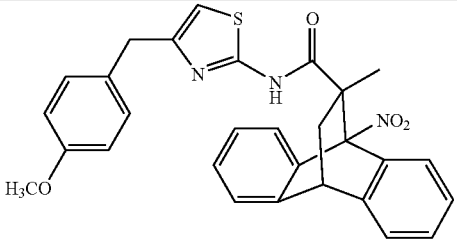 | 4.030 | 512.13 | 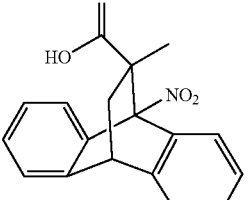 Core J |

Example 92

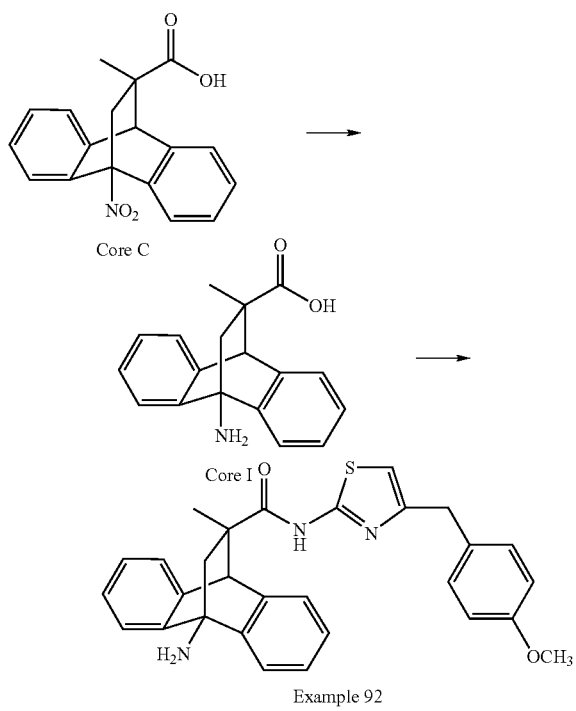

Example 92

To a solution of the acid Core C (250 mg, 0.808 mmol) in ethanol (15 ml) was added zinc dust (423 mg, 6.47 mmol) under nitrogen. The reaction mixture was cooled to 0 C, and 1 ml of concentrated hydrochloric acid was added. The reaction was allowed to warm to room temperature and stirred for 12 hours. The product mixture was concentrated and was purified by HPLC to afford the acid Core I as a white solid (115 mg, 36% yield). LC/MS m/z 280.26 (M+H)$^+$; HPLC Rt: 1.887 min. 100% purity.

Following the general coupling method B, the coupling reaction of the acid Core I (28 mg, 0.007 mmol) and (4-(4-methoxybenzyl)thiazol-2-amine (20 mg, 0.091 mmol) afforded the title compound of Example 92 as a white solid (14 mg, mmol, 34 % yield). LC/MS m/z 482.27 (M+H)$^+$; HPLC Rt: 2.933 min. 99% purity.

Example 93

In a similar manner to Example 91, the title compound of Examples 93 was prepared via the coupling reaction of the acid Core I and 4-(4-(pyridin-4-yl)benzyl)thiazol-2-amine.

| Example No. | Structure | HPLC Rt Minutes | MS m/z [(M + 1)] |
|---|---|---|---|
| 93 | 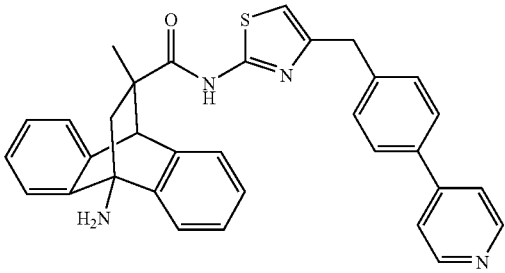 | 2.112 | 529.4 |

Example 94

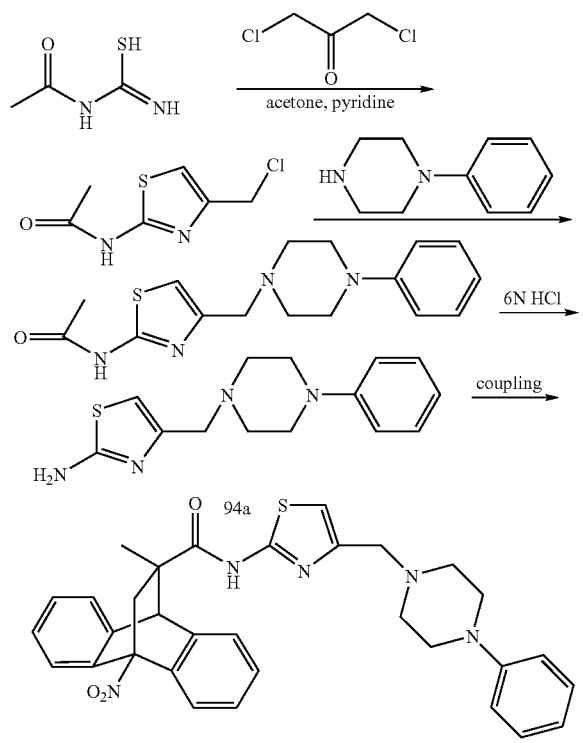

Example 94

(a) Preparation of 4-((4-phenylpiperazin-1-yl)methyl)thiazol-2-amine (94a)

N-(4-(chloromethyl)thiazol-2-yl)acetamide was prepared following a literature procedure (Silberg, A.; Frenkel, Z.; Bull. Soc. Chim. Fr.; 1967; 2235-2238). A suspension of 1-acetylisothiourea (3.55 g, 0.03 mol), 1,3-dichloropropan-2-one (3.8 g, 0.03 mol) and pyridine (1.96 g, 2 ml, 0.025 mol) in acetone (10 ml) was heated at 100 C in an oil bath for 20 minutes. A flocculent white solid formed. After cooling to room temperature, the reaction mixture was filtered to collect the white solid. The filtrate was evaporated, and the resulting residue was taken into water resulted in a white suspension which was stirred for a couple of minutes. The suspension was filtered. The collected solid was washed with water, dried under vacuum and combined with the above-mentioned white solid to give 2.89 g (51% yield) of N-(4-(chloromethyl)thiazol-2-yl)acetamide. LC/MS m/z 191.05, 193.05 (M+H)$^+$); HPLC Rt: 1.71 min.

A microwave seal tube was charged with N-(4-(chloromethyl)thiazol-2-yl)acetamide (20 mg, 0.105 mmol), 1-phenylpiperazine (17 mg, 0.105 mmol) and triethylamine (32 mg, 0.044 ml, 0.315 mmol) in 1 ml ethanol. The reaction mixture was heated at 100 C under microwave irradiation for 5 minutes. The product mixture was concentrated and purified by HPLC to give N-(4-((4-phenylpiperazin-1-yl)methyl)thiazol-2-yl)acetamide as a TFA (trifluoroacetic acid) salt, 20 mg (45% yield). LC/MS m/z 317.29 (M+H)$^+$); HPLC Rt: 1.42 min.

To a solution of N-(4-((4-phenylpiperazin-1-yl)methyl)thiazol-2-yl)acetamide TFA salt (30 mg, 0.07 mmol) in THF (2 ml) was added 6N hydrochloric acid (2 ml). The reaction was heated at reflux for 2.5 hours, and then stirred at room temperature overnight. The reaction mixture was concentrated under vacuum to give the hydrochloride salt of 4-((4-phenylpiperazin-1-yl)methyl)thiazol-2-amine 94a as a tan solid, 20 mg (92% yield). LC/MS m/z 275.24 (M+H)$^+$); HPLC Rt: 0.77 min.

(b) Following the general coupling method B, the coupling reaction of the acid Core C (22 mg, 0.071 mmol) and 4-((4-phenylpiperazin-1-yl)methyl)thiazol-2-amine 94 a (17 mg, 0.055 mmol) afforded the title compound (TFA salt) of Example 93 as a white solid (11 mg, 0.019 mmol, 29% yield). LC/MS m/z 566.18 (M+H)$^+$); HPLC Rt: 3.24 min. 99% purity.

Examples 95 to 97

In a similar manner to 94a, 4-((4-(pyridin-2-yl)piperazin-1-yl)methyl)thiazol-2-amine and 4-(morpholinomethyl)thiazol-2-amine were prepared from N-(4-(chloromethyl)thiazol-2-yl)acetamide. Following the procedure described in Example 86, Examples 95-97 were prepared via the coupling reactions of the appropriate acids (Cores A and C) and 4-((4-(pyridin-2-yl)piperazin-1-yl)methyl)thiazol-2-amine or 4-(morpholinomethyl)thiazol-2-amine.

| Example No. | Structure | HPLC Rt Minutes | MS m/z [(M + 1)] |
|---|---|---|---|
| 95 | 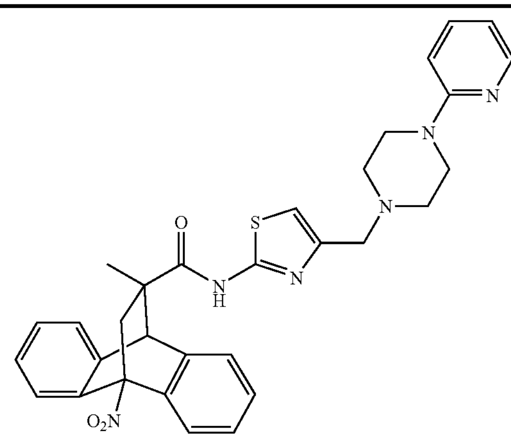 | 2.80 | 567.2 |

-continued

| Example No. | Structure | HPLC Rt Minutes | MS m/z [(M + 1)] |
|---|---|---|---|
| 96 | 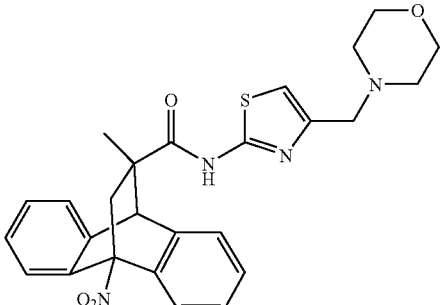 | 2.88 | 491.1 |
| 97 | 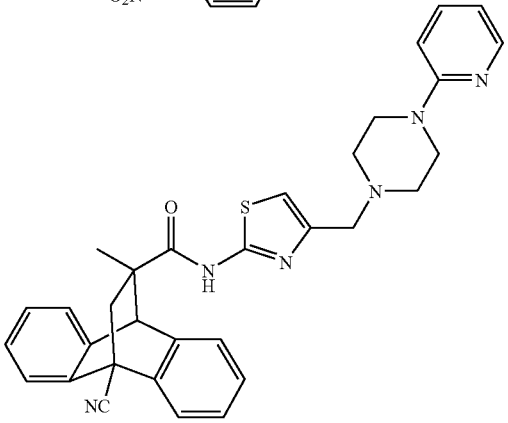 | 2.68 | 547.2 |

Example 98

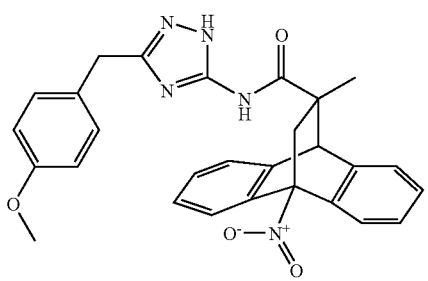

Step a 5-(4-methoxybenzyl)-1H-1,2,4-triazol-3-amine

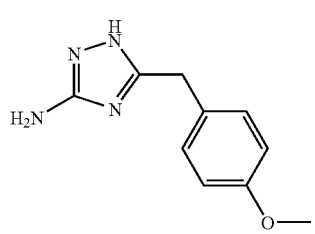

To a stirred mixture of N-aminoguanidine nitrate (5.50 g, 40 mmol) and anhydrous methanol (50 mL) cooled to 0 C was added sodium methoxide solution (25% in methanol, 9.2 mL, 40 mmol) dropwise. The resulting mixture was stirred at 0° C. for 10 min before methyl 2-(4-methoxyphenyl)acetate (1.6 mL, 10 mmol) was added. The mixture was then stirred at 0° C. for 10 min, RT for 10 min, and 75° C. for 27 hr. The reaction mixture was cooled and diluted with 20 mL of water. Methanol was removed under vacuum and the aqueous solution was acidified to pH=3-4 with 3 N aqueous HCl solution. The solid obtained was filtered, washed with water, and recrystalized in ethanol-water to give 1.65 g (81% yield) of 5-(4-methoxybenzyl)-1H-1,2,4-triazol-3-amine as a white solid. (M+H)$^+$=205.22

Step b 3-(4-methoxybenzyl)-1-[(15-methyl-8-nitrotetracyclo[6.6.2.0$^{2,7}$.0$^{9,14}$]hexadeca-2,4,6,9,11,13-hexaen-15-yl)carbonyl]-1H-1,2,4-triazol-5-amine

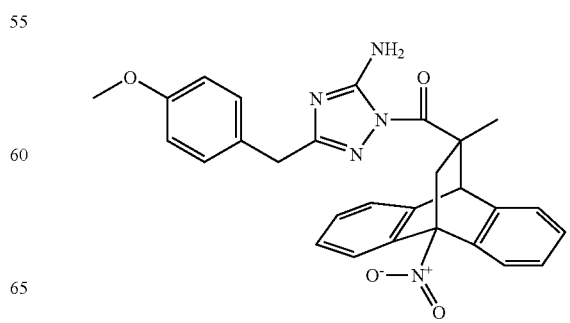

To a stirred solution of 15-methyl-8-nitrotetracyclo[6.6.2.0$^{2,7}$.0$^{9,14}$]hexadeca-2,4,6,9,11,13-hexaene-15-carboxylic acid (25 mg, 0.08 mmol, prepared according to WO04009017), 1-hydroxybenzotriazole (16 mg, 0.12 mmol), and N-ethyl-N,N-diisopropylamine (0.1 mL) in anhydrous acetonitrile (1 mL) was added EDCI (38 mg, 0.2 mmol) at RT under argon. After the mixture was stirred at RT for 5 min, 5-(4-methoxybenzyl)-1H-1,2,4-triazol-3-amine (21 mg, 0.1 mmol) was added. The reaction mixture was stirred at RT overnight and at 80° C. for 1 h. After the solvents were removed, the residue was partitioned between methylene chloride and saturated aqueous sodium bicarbonate solution. The aqueous solution was extracted with methylene chloride. The combined organic solutions were dried (Na$_2$SO$_4$), concentrated and purified by silica gel chromatography to give 35 mg (87% yield) of the title compound as a white solid. (M+H)$^+$=496.20

Step c

N-[3-(4-methoxybenzyl)-1H-1,2,4-triazol-5-yl]-15-methyl-8-nitrotetracyclo[6.6.2.0$^{2,7}$.0$^{9,14}$]hexadeca-2,4,6,9,11,13-hexaene-15-carboxamide To a solution of 3-(4-methoxybenzyl)-1-[(15-methyl-8-nitrotetracyclo[6.6.2.0$^{2,7}$.0$^{9,14}$]hexadeca-2,4,6,9,11,13-hexaen-15-yl)carbonyl]-1H-1,2,4-triazol-5-amine (33 mg, 0.067 mmol) in anhydrous THF (3 mL) was added sodium hydride (60% dispersion in mineral oil, 25 mg, 0.63 mmol) at 0° C. The mixture was stirred at 0° C. for 25 min and RT for 30 min. The reaction mixture was quenched by the addition of saturated aqueous ammonium hydrochloride solution and extracted into ethyl acetate. The ethyl acetate layer was dried (Na$_2$SO$_4$) and concentrated. Silica gel flash chromatography purification afforded 6 mg (18% yield) of Example 98. (M+H)$^+$=496.18. $^1$H-NMR (400 MHz, CD$_3$COCD$_3$): δ 12.09 (s, 1H), 10.46 (s, 1H), 7.54-7.58 (m, 1H), 7.34-7.40 (m, 3H), 7.15-7.27 (m, 6H), 6.87 (d, J=8 Hz, 2H), 5.08 (s, 1H), 3.85 (s, 2H), 3.78 (s, 3H), 3.60 (d, J=12 Hz, 1H), 2.04 (d, J=12 Hz, 1H), 1.28 (s, 3H).

Example 99

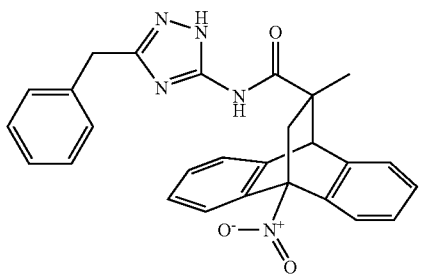

N-(3-benzyl-1H-1,2,4-triazol-5-yl)-15-methyl-8-nitrotetracyclo[6.6.2.0$^{2,7}$.0$^{9,14}$]hexadeca-2,4,6,9,11,13-hexaene-15-carboxamide 3-benzyl-1-[(15-methyl-8-nitrotetracyclo[6.6.2.0$^{2,7}$.0$^{9,14}$]hexadeca-2,4,6,9,11,13-hexaen-15-yl)carbonyl]-1H-1,2,4-triazol-5-amine, prepared according to procedure (b) as in Example 1, (13 mg, 0.028 mmol) was treated with 3-pyridinesulfonic acid (3 mg, 0.019 mmol), dimethylsulfone (66 mg), and heated at 130° C. for 2 hr and at 140° C. for 2 hr under argon. Saturated aqueous sodium bicarbonate solution was added and the mixture was extracted with methylene chloride. The combined methylene chloride solutions were dried and concentrated. Silica gel flash chromatography purification gave 7 mg (54% yield) of Example 99 as a white solid. (M+H)$^+$=466.15. $^1$H-NMR (400 MHz, CD$_3$COCD$_3$): δ 12.08 (s, 1H), 10.36 (s, 1H), 7.39-7.43 (m, 1H), 7.13-7.25 (m, 7H), 7.00-7.12 (m, 5H), 4.92 (s, 1H), 3.78 (s, 2H), 3.46 (d, J=12 Hz, 1H), 1.89 (d, J=12 Hz, 1H), 1.13 (s, 3H).

Example 100

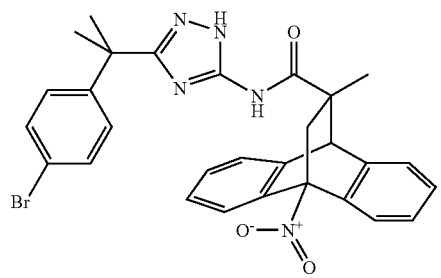

Step a

5-[1-(4-bromophenyl)-1-methylethyl]-1H-1,2,4-triazol-3-amine

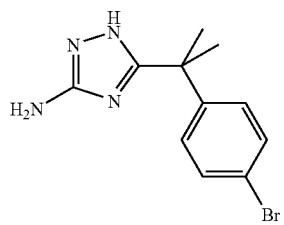

To a stirred mixture of N-aminoguanidine nitrate (2.1 g, 15 mmol) and anhydrous methanol (18 mL) cooled to 0° C. was added sodium methoxide solution (25% in methanol, 3.4 mL, 15 mmol) dropwise. The resulting mixture was stirred at 0° C. for 10 min before methyl 2-(4-bromophenyl)-2-methylpropanoate (1.0 g, 3.9 mmol) was added. The mixture was then stirred at 0° C. for 10 min, RT for 10 min, and 75 ° C. for 6 days. The reaction mixture was cooled and diluted with 20 mL of water. Methanol was removed under vacuum and the aqueous solution was acidified to pH=3-4 with 3 N aqueous HCl solution and extracted with ethyl acetate. The ethyl acetate layer was dried (Na$_2$SO$_4$) and concentrated. Silica gel flash chromatography purification gave 330 mg (31% yield) of the title compound as a yellow solid. (M+H)$^+$=281.14

Step b

3-[1-(4-bromophenyl)-1-methylethyl]-1-[(15-methyl-8-nitrotetracyclo[6.6.2.0$^{2,7}$.0$^{9,14}$]hexadeca-2,4,6,9,11,13-hexaen-15-yl)carbonyl]-1H-1,2,4-triazol-5-amine

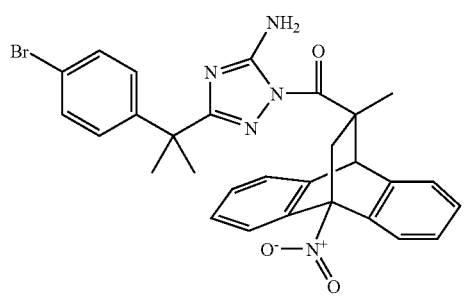

To a stirred solution of 15-methyl-8-nitrotetracyclo[6.6.2.0$^{2,7}$.0$^{9,14}$]hexadeca-2,4,6,9,11,13-hexaene-15-carboxylic acid (31 mg, 0.10 mmol, prepared according to WO04009017), 1-hydroxybenzotriazole (20 mg, 0.15 mmol), and N-ethyl-N,N-diisopropylamine (0.15 mL) in anhydrous acetonitrile (1.5 mL) was added EDCI (39 mg, 0.2 mmol) at RT under argon. After the mixture was stirred at RT for 5 min, 5-[1-(4-bromophenyl)-1-methylethyl]-1H-1,2,4-triazol-3-amine (28 mg, 0.1 mmol) was added. The reaction mixture was stirred at RT for 2 h and at 80° C. for 1 h. After the solvents were removed, the residue was partitioned between methylene chloride and saturated aqueous sodium bicarbonate solution. The aqueous solution was extracted with methylene chloride. The combined organic solutions were dried (Na$_2$SO$_4$), concentrated and purified by silica gel chromatography to give 53 mg (93% yield) of the title compound as a white solid which was used as such for the subsequent step without further purification.

Step c

N-{3-[1-(4-bromophenyl)-1-methylethyl]-1H-1,2,4-triazol-5-yl}-15-methyl-8-nitrotetracyclo[6.6.2.0$^{2,7}$.0$^{9,14}$]hexadeca-2,4,6,9,11,13-hexaene-15-carboxamide 3-[1-(4-bromophenyl)-1-methylethyl]-1-[(15-methyl-8-nitrotetracyclo[6.6.2.0$^{2,7}$.0$^{9,14}$]hexadeca-2,4,6,9,11,13-hexaen-15-yl)carbonyl]-1H-1,2,4-triazol-5-amine (53 mg, 0.093 mmol) was treated with 3-pyridinesulfonic acid (15 mg, 0.093 mmol) and dimethylsulfone (250 mg), and then heated at 145° C. for 2.5 hr and 160° C. for 2 hr under argon. The mixture was dissolved in methanol. HPLC purification (YMC S5 ODS column 20×100 mm, 10-90% aqueous methanol over 10 minutes containing 0.1% trifluoroacetic acid, 20 mL/min, monitoring at 220 nm) gave 18 mg (34% yield) of Example 100 as a white solid. (M+H)$^+$=572.10. $^1$H-NMR (400 MHz, CDCl$_3$): δ 7.40-7.44 (m, 3H), 7.15-7.33 (m, 9H), 4.46 (s, 1H), 3.32 (d, J=12 Hz, 1H), 2.09 (d, J=12 Hz, 1H), 1.73 (d J=8 Hz, 6H), 1.16 (s, 3H).

Example 101

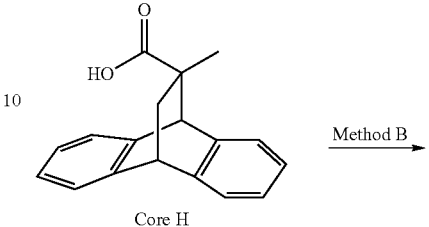

Core H

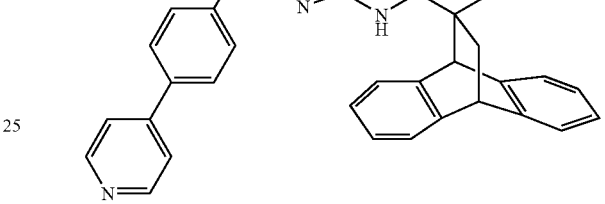

The title compound was prepared from homochiral Core H (S enantiomer) in the same manner as described for the preparation of 69. MS found: (M+H)$^+$=514.

Example 102

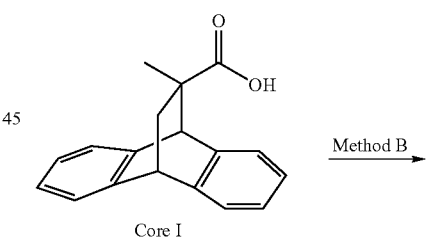

Core I

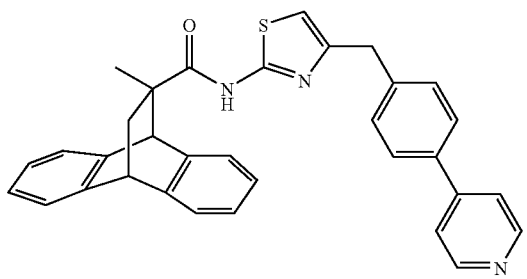

The title compound was prepared from homochiral Core I (R enantiomer) in the same manner as described for the preparation of 69. MS found: (M+H)$^+$=514.

Example 103

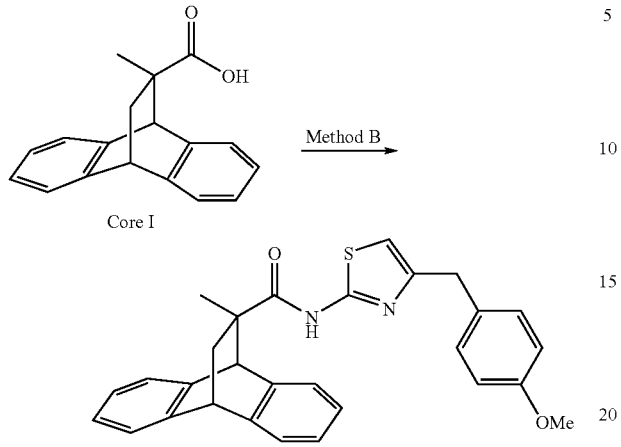

The title compound was prepared from homochiral Core I (R enantiomer) and 10c in the same manner as described for the preparation of 11. MS found: (M+H)$^+$=467.

Example 104

The title compound was prepared from homochiral Core H (S enantiomer) and 10c in the same manner as described for the preparation of 11. MS found: (M+H)$^+$=467.

What is claimed is:

1. A compound having a structure of formula (I):

(I)

or a stereoisomer thereof, or a tautomer thereof, or a pharmaceutically acceptable salt thereof, wherein:

X is selected from N, NH, O, and S;

Y is N, NH, or CR$^6$;

R is hydrogen, cyano, hydroxy, alkyl, alkenyl, alkynyl, alkoxy, aryl, arylalkyl, aryloxy, heteroaryl, cycloheteroalkyl, heteroarylalkyl, cycloheteroalkylalkyl, cycloalkyl, cycloalkylalkyl, cyanoalkyl, hydroxyalkyl, aryloxyalkyl, or hydroxyaryl;

Z is a cycloalkyl, cycloalkenyl, heterocycloalkyl, aryl, or heteroaryl ring;

R$^1$ is hydrogen or C$_{1-4}$alkyl;

R$^2$ is hydrogen, halogen, or hydroxy;

R$^3$ is hydrogen, halogen, hydroxy, alkyl, alkenyl, alkynyl, alkoxy, cyano, nitro, NR$^e$R$^f$, or CHO;

or R$^2$ and R$^3$ combine to form a double bond, wherein the double bond is substituted by hydrogen, aryl, alkyl, alkenyl, alkynyl, alkoxy, amino, substituted amino, alkoxyalkyl, alkylaminoalkyl, dialkylaminoalkyl, heteroaryl, cycloheteroalkyl, heteroarylalkyl, cycloheteroalkylalkyl, cycloalkyl, or cycloalkylalkyl;

R$^4$ and R$^5$ are independently at each occurence hydrogen, alkyl, aryl, cycloalkyl, heteroaryl, or cycloheteroalkyl;

R$^6$ is hydrogen, halogen, hydroxy, alkyl, alkenyl, alkynyl, alkoxy, aryl, aryloxy, heteroaryl, cycloheteroalkyl, heteroarylalkyl, cycloheteroalkylalkyl, cyano, heteroarylaminocarboyl, cycloheteroalkylcarbonyl, cyanoalkyl, alkylaminoalkyl, hydroxyalkyl, hydroxyaryl, aryloxyalkyl, nitro, NR$^e$R$^f$, CHO, CO$_2$alkyl, alkyloxyalkyl, CONR$^e$R$^f$, CH$_2$NR$^e$R$^f$, CO$_2$H, CH$_2$OH, CH$_2$NHC(O)R$^e$R$^f$, NHCOR$^g$, NHCONR$^e$R$^f$, NHSO$_p$R$^g$, SO$_2$NR$^e$R$^f$, NR$^e$SO$_2$NR$^e$R$^f$, or NR$^e$SO$_p$R$^g$;

R$^a$ and R$^b$ are independently selected from hydrogen, halogen, hydroxy, alkyl, alkenyl, alkynyl, alkoxy, aryl, aryloxy, heteroaryl, cycloheteroalkyl, heteroarylalkyl, cycloheteroalkylalkyl, cyano, heteroarylaminocarboyl, cycloheteroalkylcarbonyl, cyanoalkyl, alkylaminoalkyl, hydroxyalkyl, hydroxyaryl, aryloxyalkyl, alkyloxyalkyl, nitro, NR$^e$R$^f$, CHO, CO$_2$alkyl, CONR$^e$R$^f$, CH$_2$NR$^e$R$^f$, CO$_2$H, CH$_2$OH, CH$_2$NR$^e$R$^f$, NHCOR$^g$, NHCONR$^e$R$^f$, and NHSO$_2$R$^g$;

R$^c$ and R$^d$ are independently selected from hydrogen, alkyl, alkenyl, alkynyl, alkoxy, NR$^e$R$^f$, aryl, hydroxy, aryloxy, heteroaryl, cycloheteroalkyl, heteroarylalkyl, cycloheteroalkylalkyl, hydroxyaryl, and aryloxyalkyl;

R$^e$ and R$^f$ are independently at each occurrence selected from hydrogen, aryl, alkyl, alkenyl, alkynyl, alkoxy, amino, substituted amino, alkoxyalkyl, alkylaminoalkyl, dialkylaminoalkyl, heteroaryl, cycloheteroalkyl, heteroarylalkyl, cycloheteroalkylalkyl, cycloalkyl, and cycloalkylalkyl, provided R$^e$ and R$^f$ are not both alkoxy or amino;

or R$^e$ and R$^f$ at each occurrence can be taken together with the nitrogen to which they are attached to form a 5-, 6- or 7-membered heteroaryl or cycloheteroalkyl ring which contains 1, 2 or 3 hetero atoms which can be N, O or S;

R$^g$ and R$^i$ independently at each occurrence are selected from hydrogen, aryl, alkyl, alkenyl, alkynyl, alkoxy, amino, substituted amino, alkoxyalkyl, alkylaminoalkyl, dialkylaminoalkyl, heteroaryl, cycloheteroalkyl, heteroarylalkyl, cycloheteroalkylalkyl, cycloalkyl, and cycloalkylalkyl;

p is 0, 1 or 2;

r is 0, 1 or 2; and s is 0, 1 or 2.

2. A compound as defined in claim 1, or a stereoisomer thereof, or a tautomer thereof, or a pharmaceutically acceptable salt thereof, wherein:

Z is a cycloalkyl, cycloalkenyl, heterocycloalkyl, aryl, or heteroaryl ring where each ring is substituted by 0-4 $R^7$ and 0-1 $R^8$;

$R^6$ is hydrogen, halogen, hydroxy, $C_{1-4}$alkyl, trifluoromethyl, $C_{1-4}$alkoxy, C(O)$NR^eR^f$, nitro, or cyano;

$R^7$ and $R^8$ are independently at each occurrence hydrogen, halogen, hydroxy, alkyl, alkenyl, alkynyl, alkoxy, aryl, aryloxy, heteroaryl, cycloheteroalkyl, heteroarylalkyl, cycloheteroalkylalkyl, cyano, heteroarylaminocarboyl, cycloheteroalkylcarbonyl, cyanoalkyl, alkylaminoalkyl, hydroxyalkyl, hydroxyaryl, aryloxyalkyl, alkoxyalkyl, nitro, oxo, O(CH$_2$)$_z$$R^h$, $NR^eR^f$, CHO, CO$_2$alkyl, CONR$^e$R$^f$, CH$_2$NR$^e$R$^f$, CO$_2$H, CH$_2$OH, CH$_2$NHC(O)R$^e$R$^f$, NR$^g$COR$^i$, NR$^g$CONR$^e$R$^f$, NR$^g$SO$_p$R$^i$, —SO$_2$NR$^e$R$^f$, NR$^g$SO$_2$NR$^e$R$^f$, or NR$^g$SO$_p$R$^i$;

or $R^7$ and $R^8$ located on adjacent atoms can be taken together to form an optionally substituted cycloalkyl, aryl, heteroaryl, or cycloheteroalkyl ring;

$R^h$ is selected from aminocarbonyl, O(CH$_2$)$_z$O(CH$_2$)$_y$$R^i$, alkylamino, heterocycloalkyl, heteroaryl, and aryl; and v, y and z are independently at each occurrence selected from 0, 1 and 2.

3. A compound as defined in claim 1 having the structure

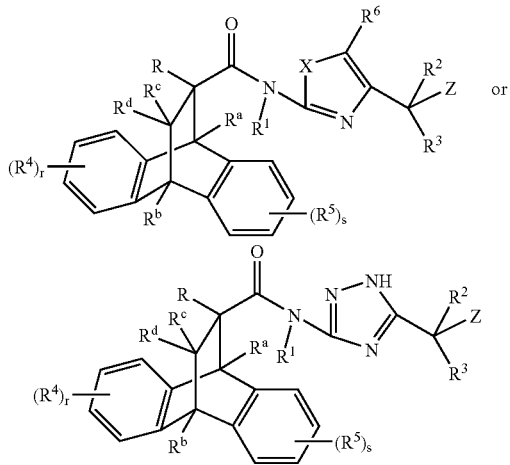

or a stereoisomer thereof, or a tautomer thereof, or a pharmaceutically acceptable salt thereof, wherein:

R is H or alkyl; and $R^c$ and $R^d$ are independently selected from H, halogen, OH, CN, NO$_2$, NH$_2$, CHO, CO$_2$alkyl, CONR$^e$R$^f$ and CH$_2$NR$^e$R$^f$.

4. A compound as defined in claim 3, or a stereoisomer thereof, or a tautomer thereof, or a pharmaceutically acceptable salt thereof, wherein:

R is H or $C_{1-4}$alkyl; and $R^c$ and $R^d$ are both H.

5. A compound as defined in claim 3, or a stereoisomer thereof, or a tautomer thereof, or a pharmaceutically acceptable salt thereof, wherein:

$R^a$ is selected from H and NO$_2$; and $R^b$ is selected from H, CH$_3$, Cl, Br, NH$_2$, CN, and NO$_2$.

6. A compound as defined in claim 3, or a stereoisomer thereof, or a tautomer thereof, or a pharmaceutically acceptable salt thereof, wherein X is NH or S.

7. A compound as defined in claim 3, or a stereoisomer thereof, or a tautomer thereof, or a pharmaceutically acceptable salt thereof, wherein Z is a heterocycloalkyl, aryl, or heteroaryl ring, each ring substituted by 0-4 $R^7$ and 0-1 $R^8$.

8. A compound as defined in claim 7 or a stereoisomer thereof, or a tautomer thereof, or a pharmaceutically acceptable salt thereof, wherein:

Z is a phenyl, naphthyl, pyrimidyl, pyridinyl, pyridazinyl, piperazinyl, thiophenyl, thiazolyl, isoxazolyl, or imidazolyl ring;

$R^6$ is hydrogen;

$R^7$ and $R^8$ are independently at each occurrence:

(a) hydrogen, bromo, chloro, fluoro, $C_{1-4}$alkyl, arylalkyl, OR$^{11}$, oxo, NO$_2$, cyano, NH$_2$, —NHC$_{1-4}$alkyl, —N(C$_{1-4}$alkyl)$_2$, SO$_2$C$_{1-4}$alkyl, NHC(O)C$_{1-4}$alkyl, C(O)N(C$_{1-4}$alkyl)$_2$, C(O)NH(C$_{1-4}$alkyl), C(O)NH$_2$, CO$_2$H, CO$_2$(C$_{1-4}$alkyl), or arylalkyl; or (b) a phenyl, naphthyl, pyrazolyl, pyrimidinyl, pyridinyl, isoxazolyl, indolyl, or morpholinyl ring; each of which is optionally further substituted by 1-3 $R^{13}$; or (c) $R^7$ and $R^8$ located on adjacent atoms can be taken together to form a dioxole or phenyl ring, where each ring is optionally further substituted;

$R^{11}$ at each occurrence is selected from hydrogen, $C_{1-4}$alkyl, (CH$_2$)$_v$C(O)NH$_2$, (CH$_2$)$_v$heteroaryl, (CH$_2$)$_v$O(CH$_2$)$_y$O(CH$_2$)$_z$OR$^{12}$, (CH$_2$)$_v$N(C$_{1-4}$alkyl)$_2$, (CH$_2$)$_v$heterocycloalkyl, and (CH$_2$)$_v$phenyl;

$R^{12}$ is hydrogen or $C_{1-4}$alkyl; and $R^{13}$ is halogen, oxo, NH$_2$, hydroxy, $C_{1-4}$alkyl, $C_{1-4}$alkoxy, —(CH$_2$)aryl, or heterocycloalkyl.

9. The compound as defined in claim 8, or a stereoisomer thereof, or a tautomer thereof, or a pharmaceutically acceptable salt thereof, wherein Z is selected from:

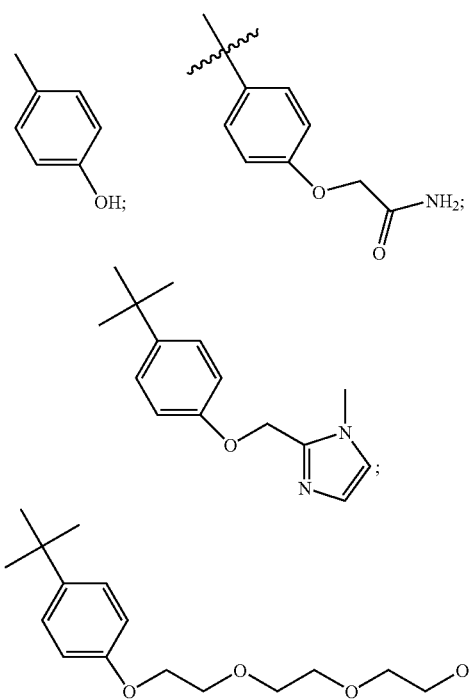

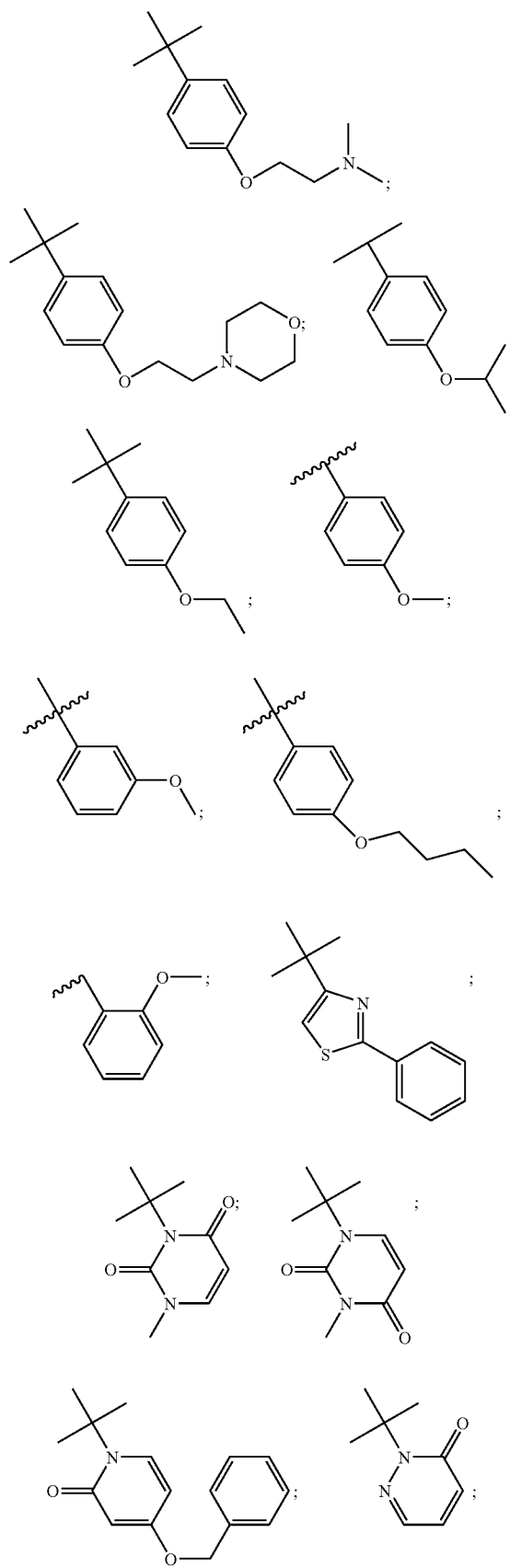
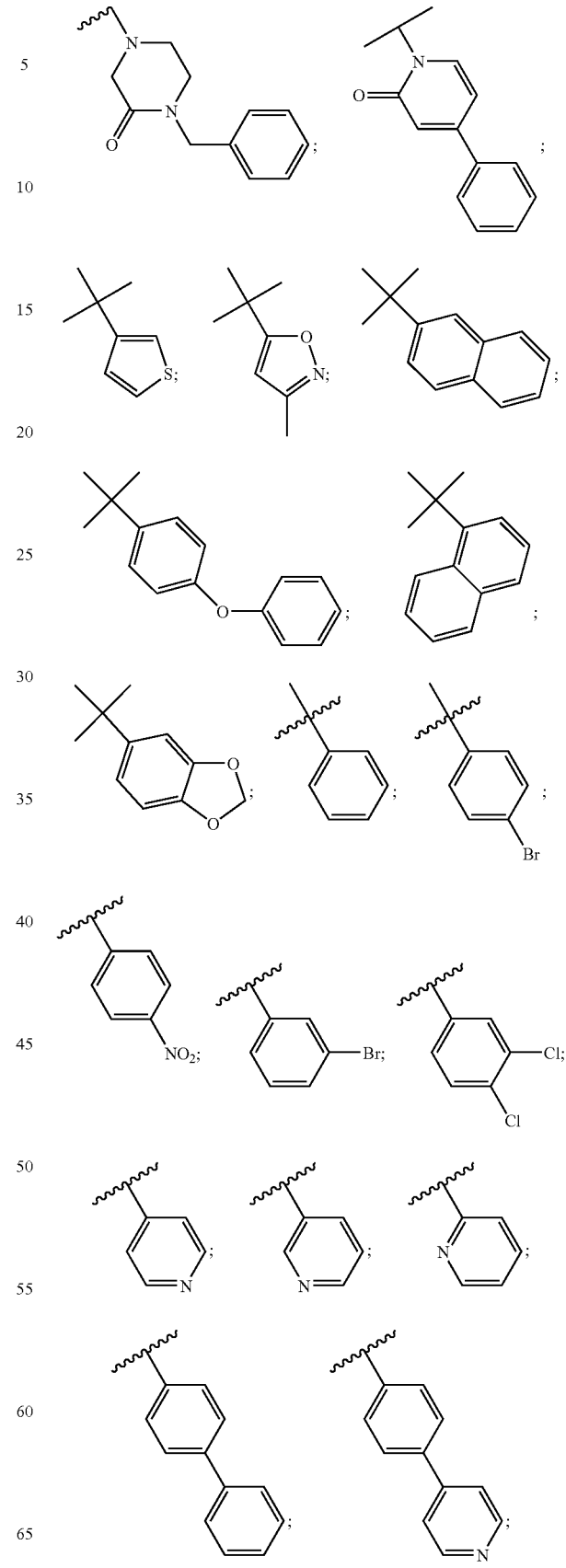

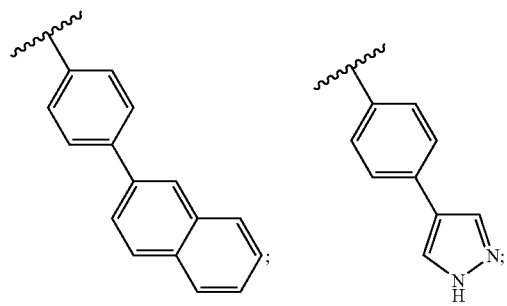
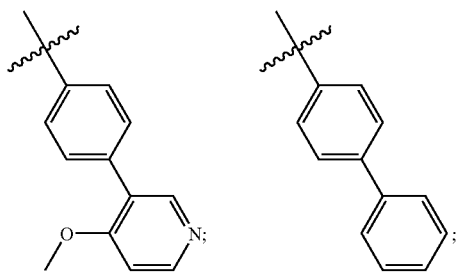
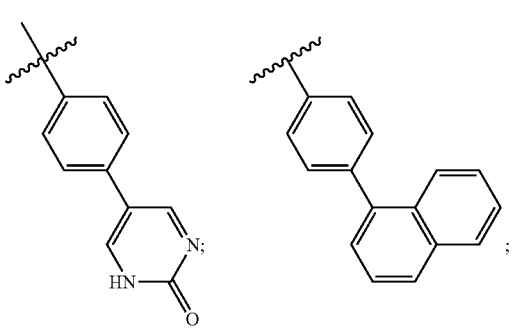
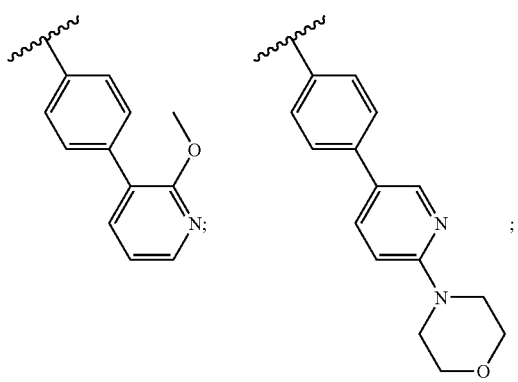
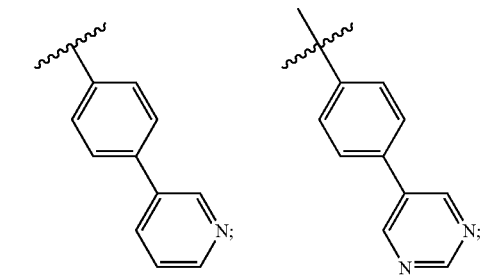
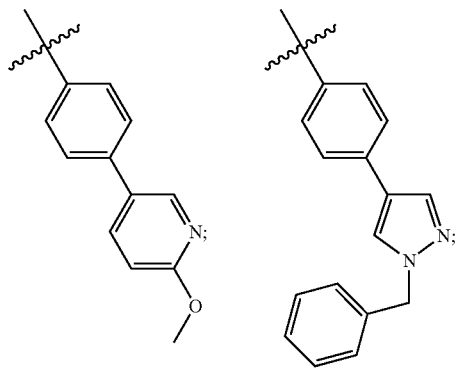
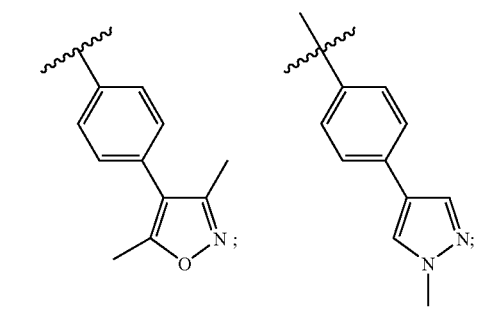
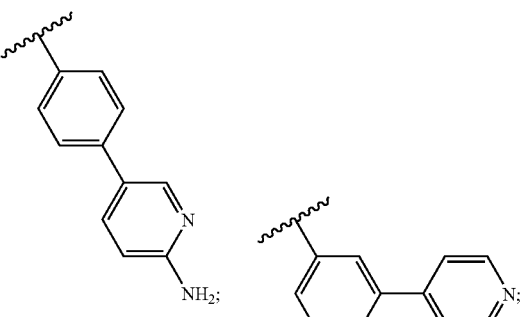
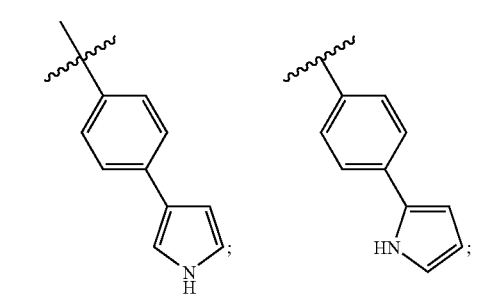
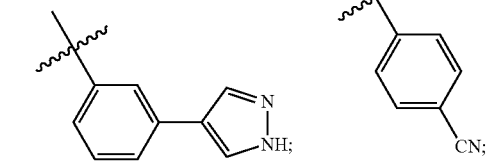

-continued

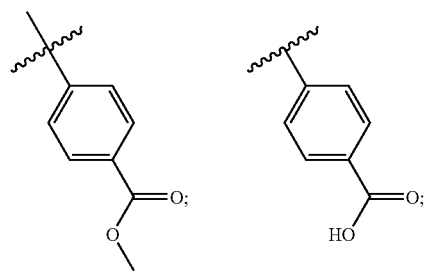
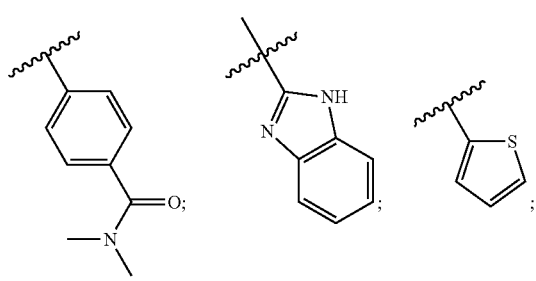
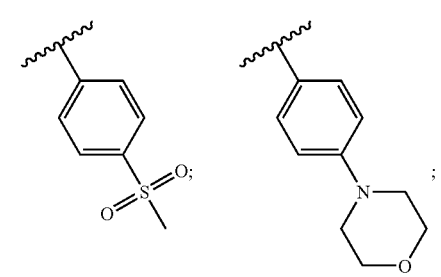
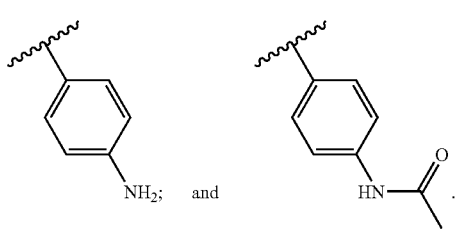

10. A compound as defined in claim 1, or a stereoisomer thereof, or a tautomer thereof, or a pharmaceutically acceptable salt thereof, wherein:

$R^2$ and $R^3$ are independently hydrogen, halogen, or hydroxyl.

11. A compound as defined in claim 6 having the formula:

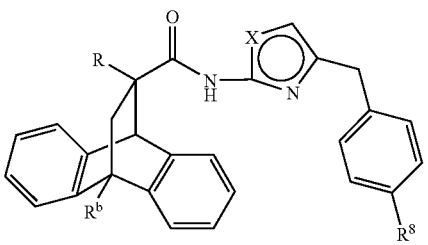

or a stereoisomer thereof, or a tautomer thereof, or a pharmaceutically acceptable salt thereof, wherein:

R is $C_{1-4}$alkyl;

$R^8$ is $C_{1-4}$alkoxy, halogen, pyrimidine, isoxazole, pyrazole, or pyridine, where the $C_{1-4}$alkoxy, halogen, pyrimidine, isoxazole, pyrazole, or pyridine groups are substituted by hydrogen, morpholinyl, $C_{1-4}$alkoxy, or $C_{1-4}$alkyl; and $R^b$ is selected from H, $CH_3$, Cl, Br, and CN.

12. A compound as defined in claim 6, having the formula:

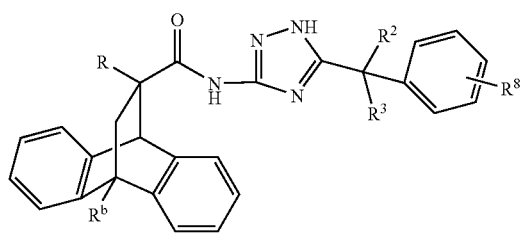

including all stereoisomers thereof, or a pharmaceutically acceptable salt thereof, wherein:

R is $C_{1-4}$alkyl;

$R^2$ and $R^3$ are independently hydrogen, halogen, hydroxy, alkyl, alkenyl, alkynyl, alkoxy, cyano, nitro, $NR^eR^f$, or CHO;

or $R^2$ and $R^3$ combine to form a double bond, wherein the double bond is substituted by hydrogen, aryl, alkyl, alkenyl, alkynyl, alkoxy, amino, substituted amino, alkoxyalkyl, alkylaminoalkyl, dialkylaminoalkyl, heteroaryl, heterocycloalkyl, heteroarylalkyl, heterocycloalkylalkyl, cycloalkyl, or cycloalkylalkyl; and $R^b$ is selected from H, $CH_3$, Cl, Br, $NO_2$, and CN.

13. A compound selected from:
(i)
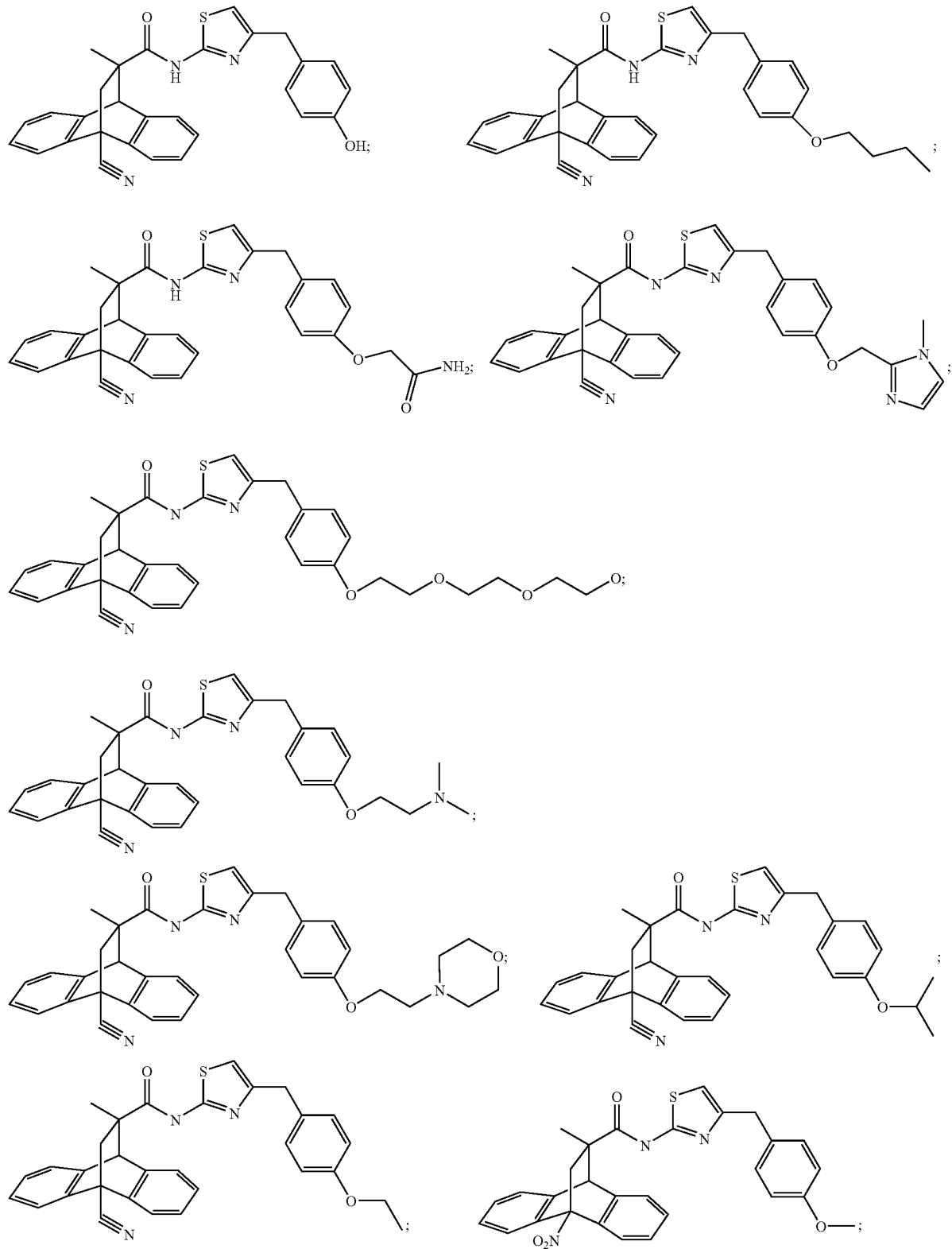

-continued
| 115 | 116 |
|---|---|
| 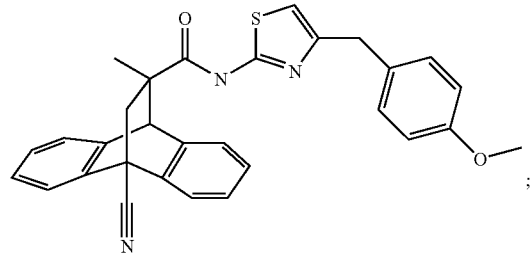 | 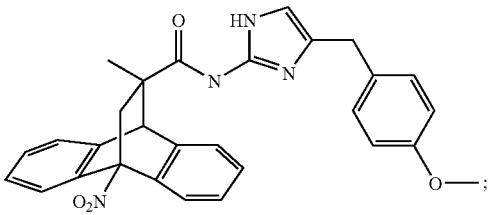 |
| 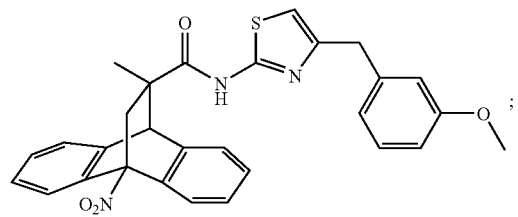 | 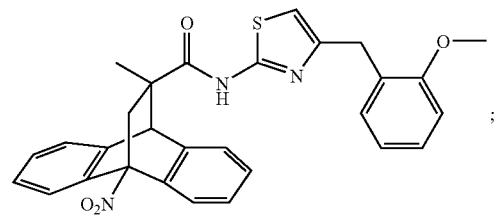 |
| 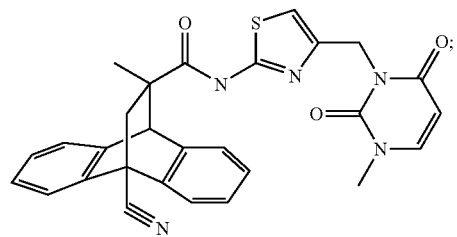 | 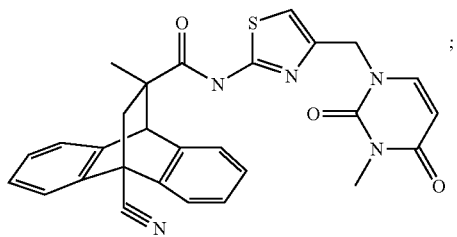 |
| 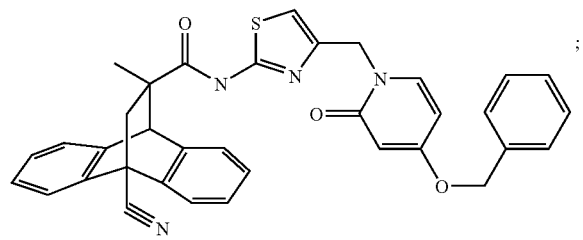 | 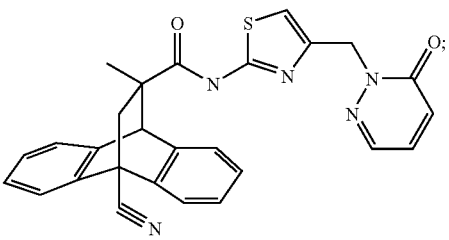 |
| 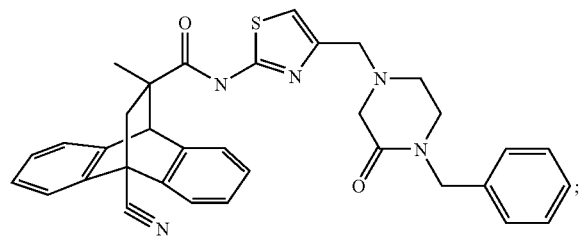 | 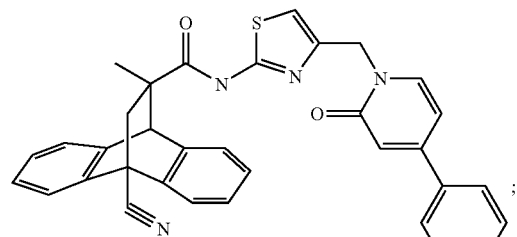 |
| 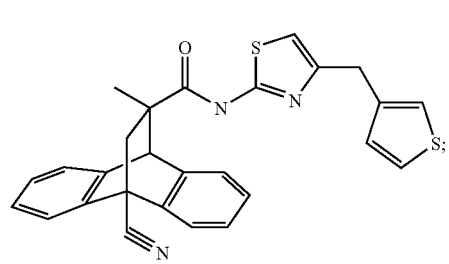 | 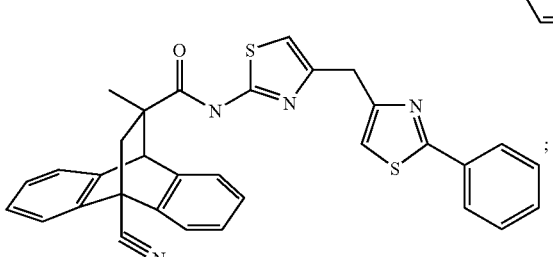 |
| 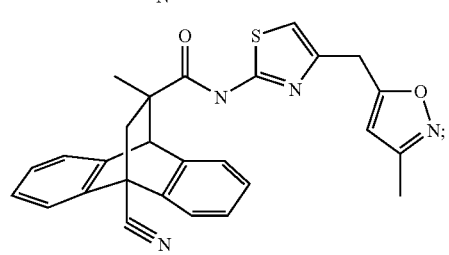 | 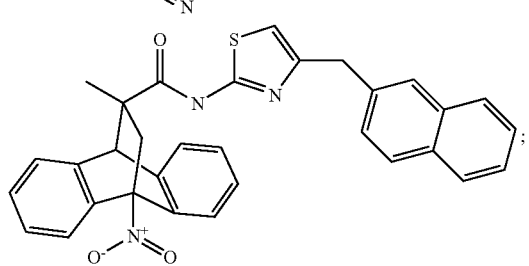 |

-continued
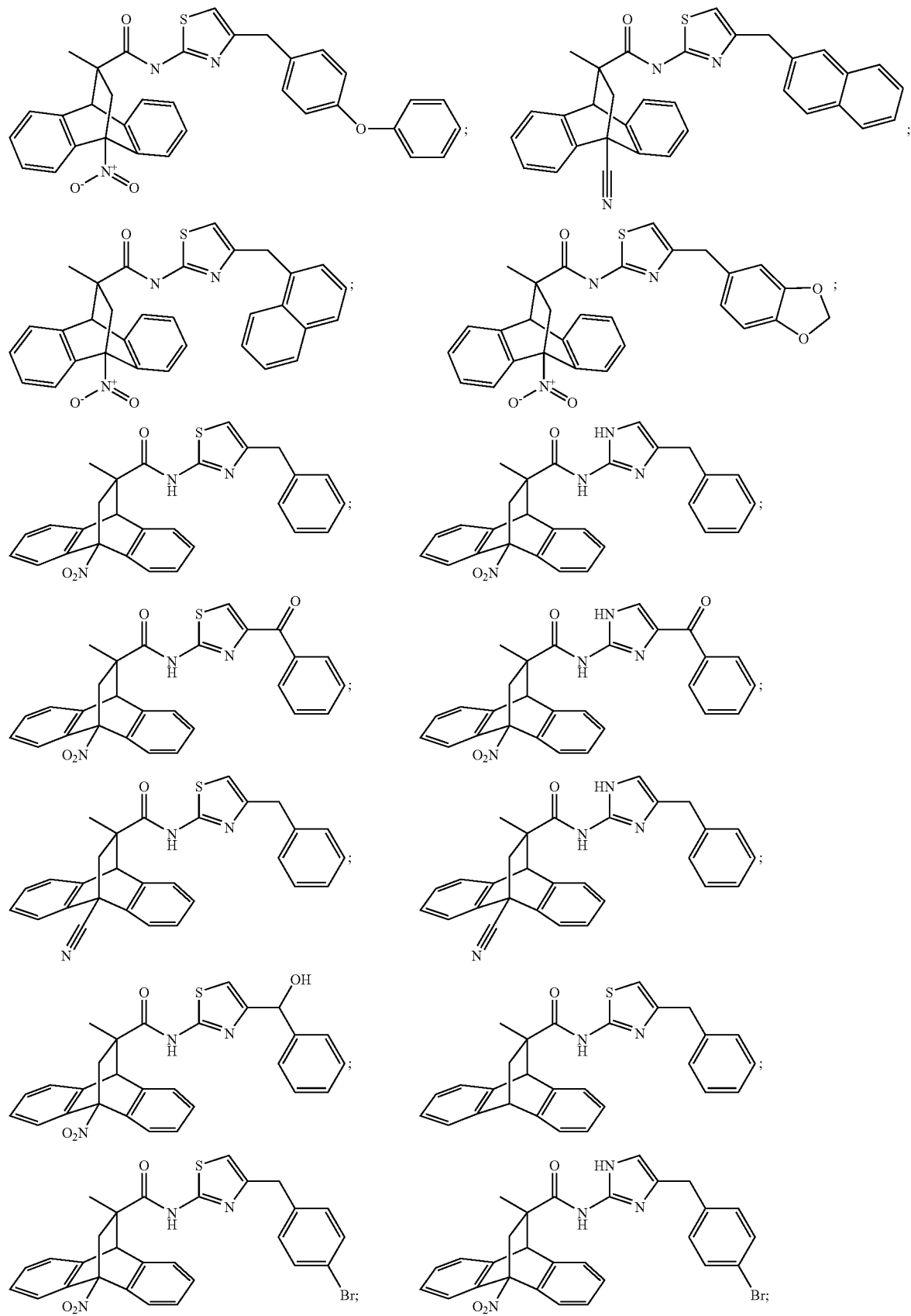

-continued
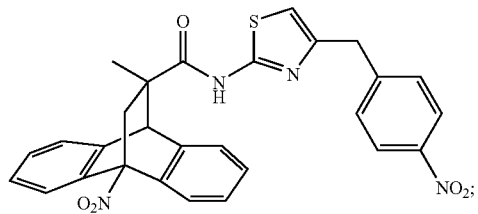
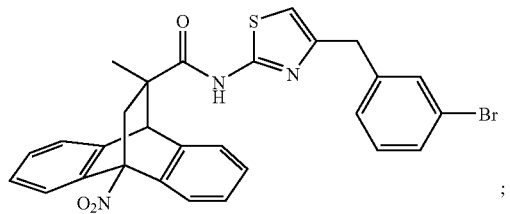
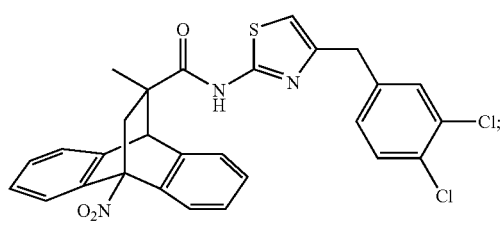
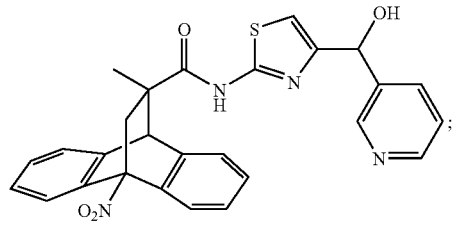
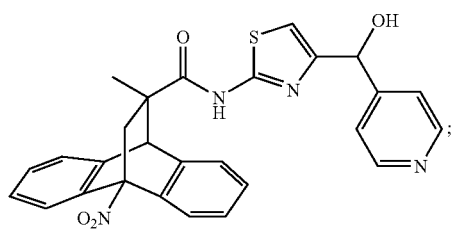
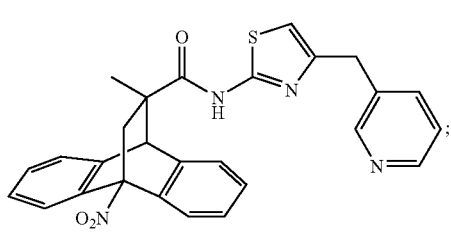
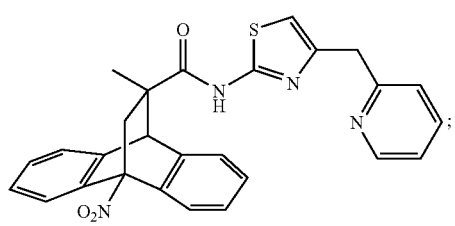
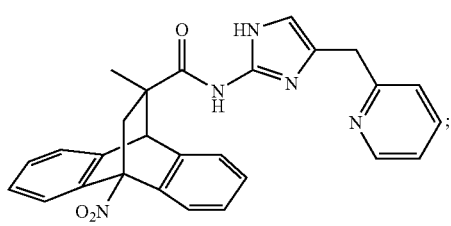
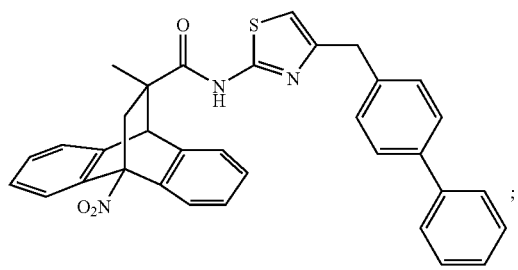
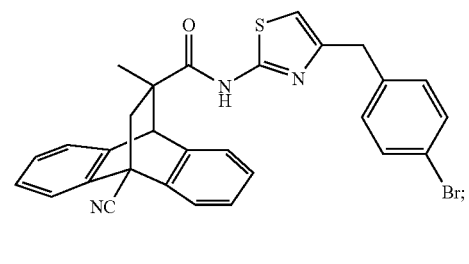
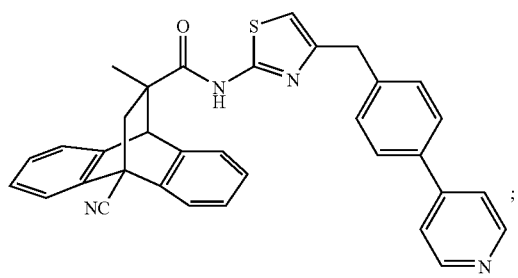
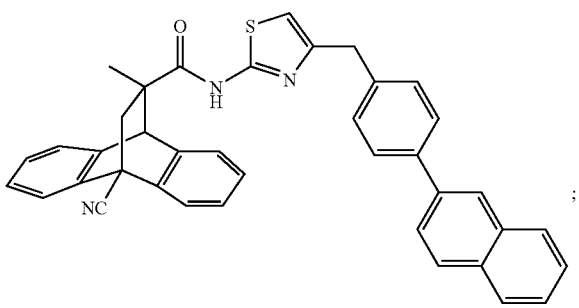

-continued
121
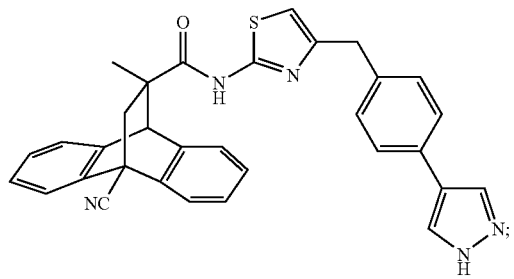
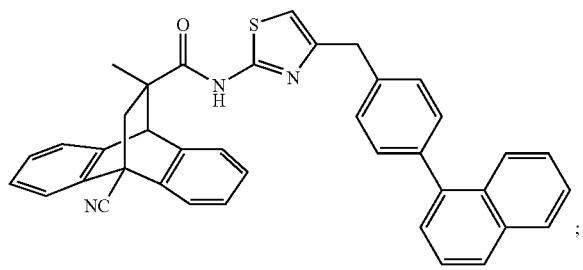
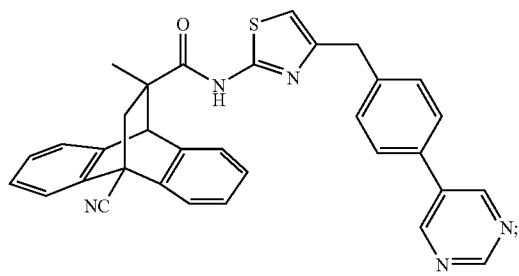
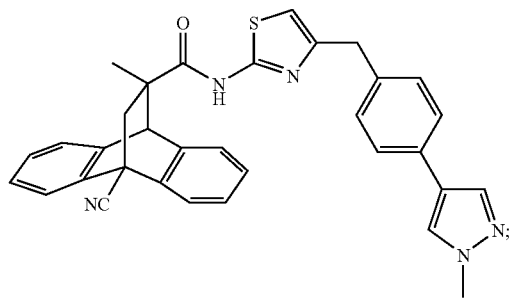
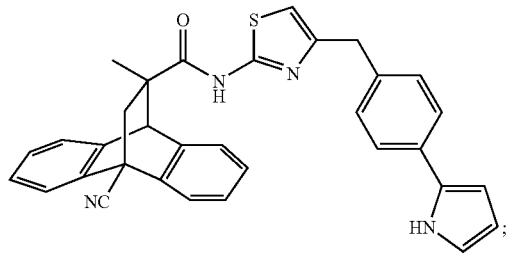
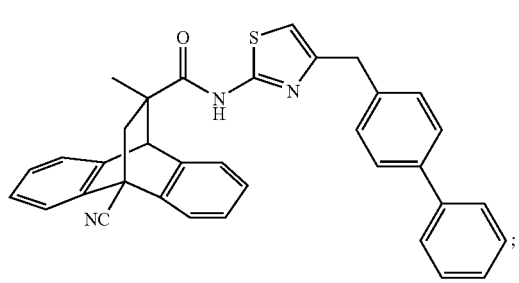
122
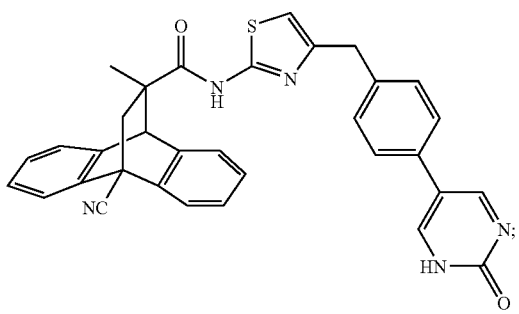
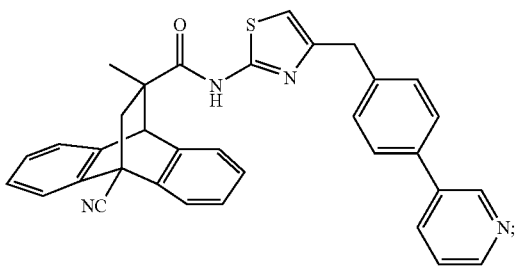
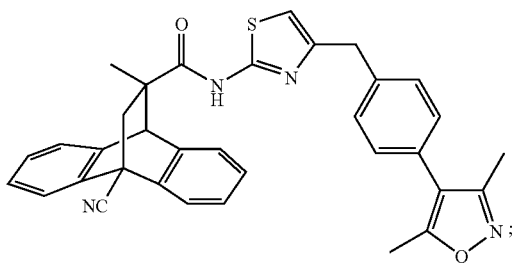
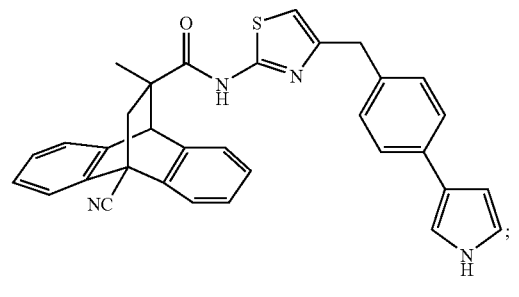
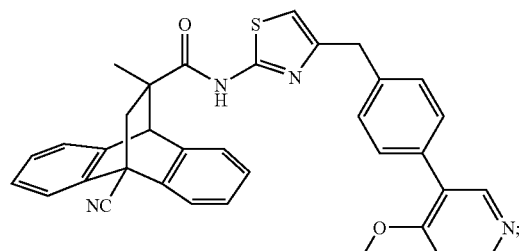
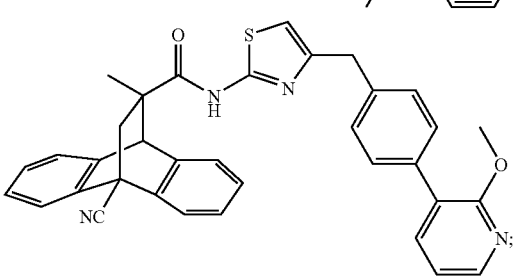

-continued
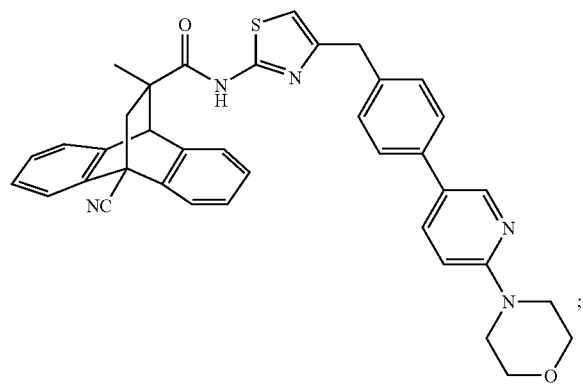
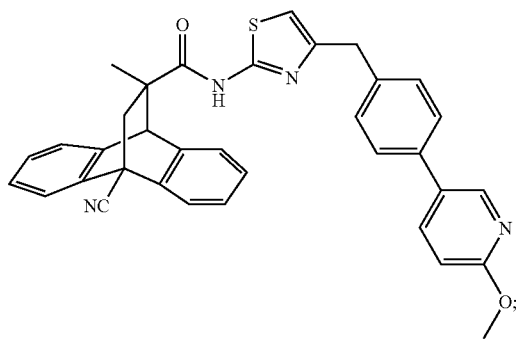
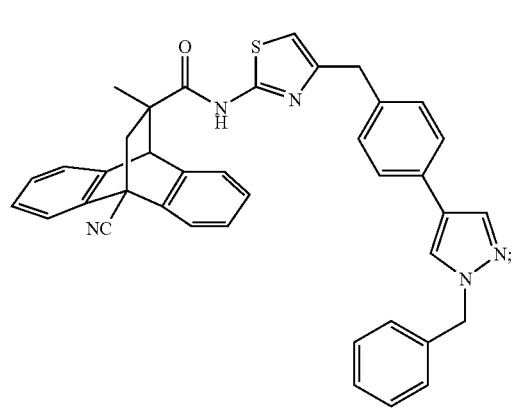
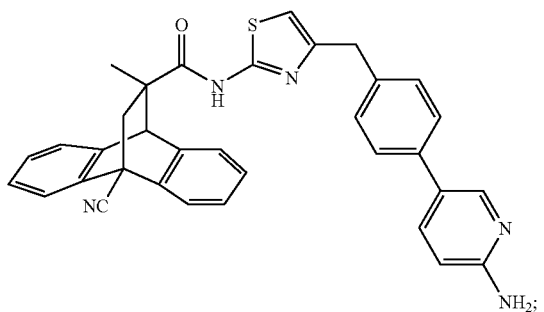
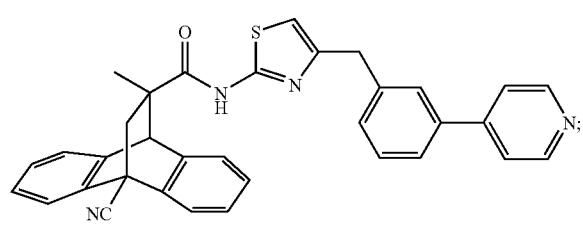
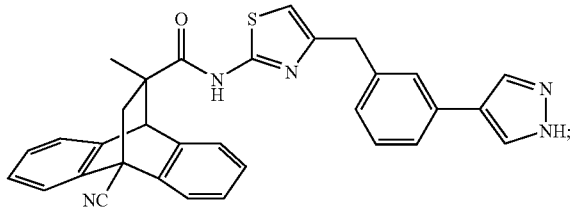
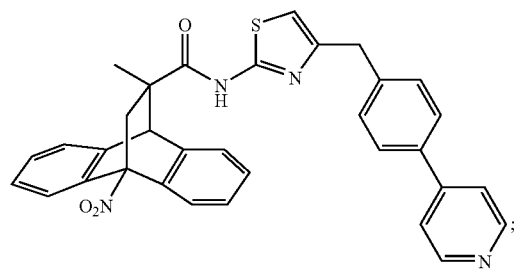
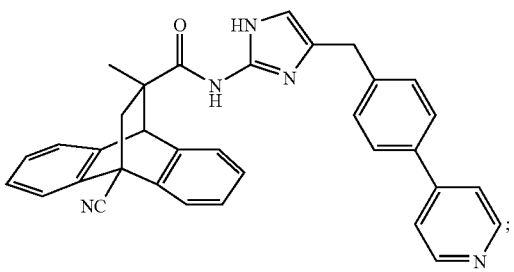
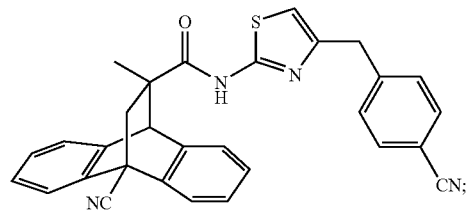
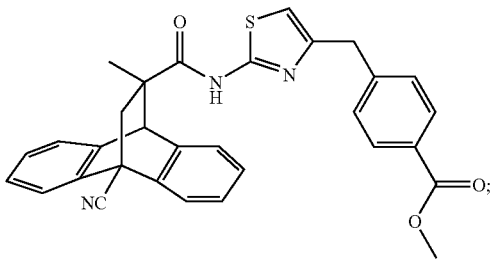

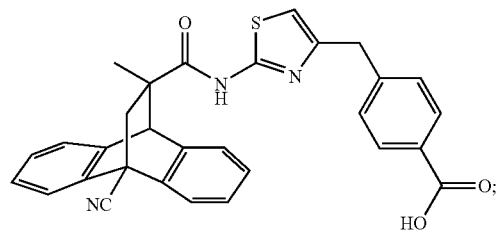
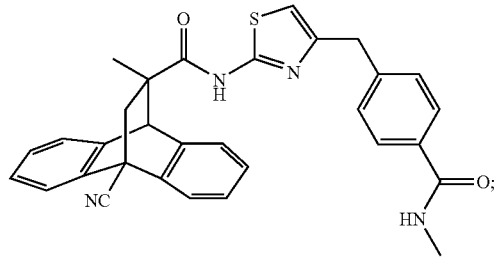
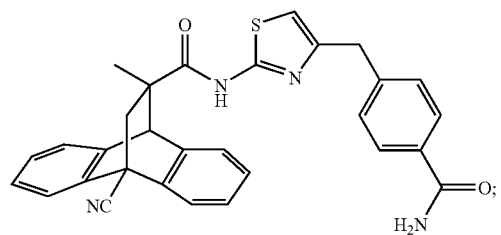
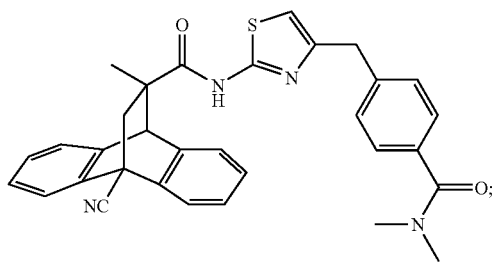
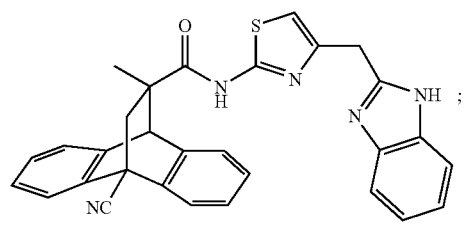
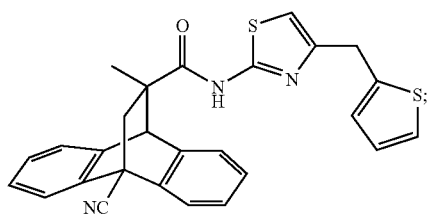
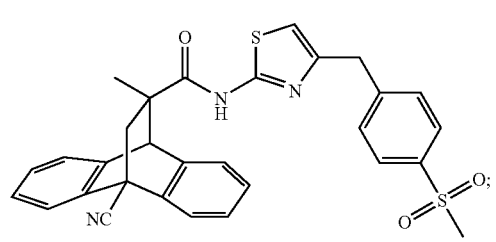
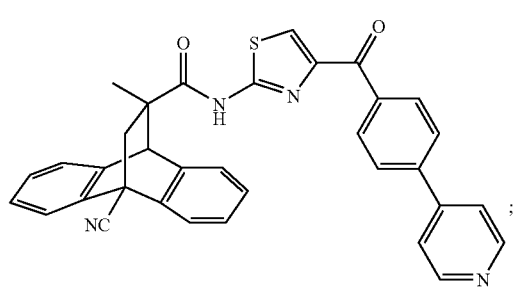
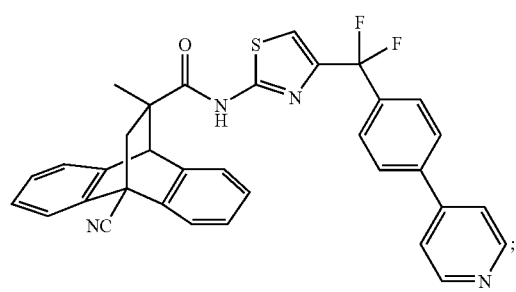
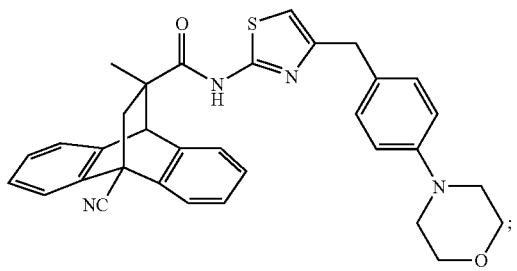
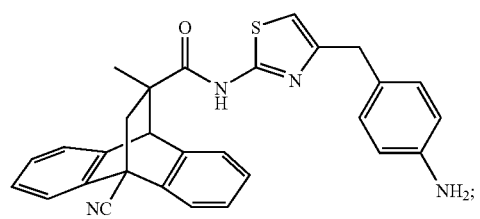
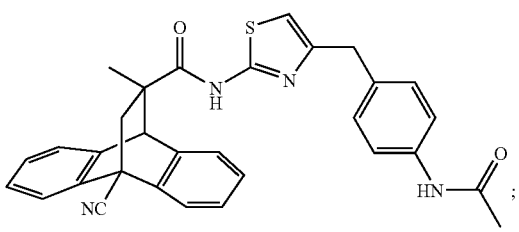

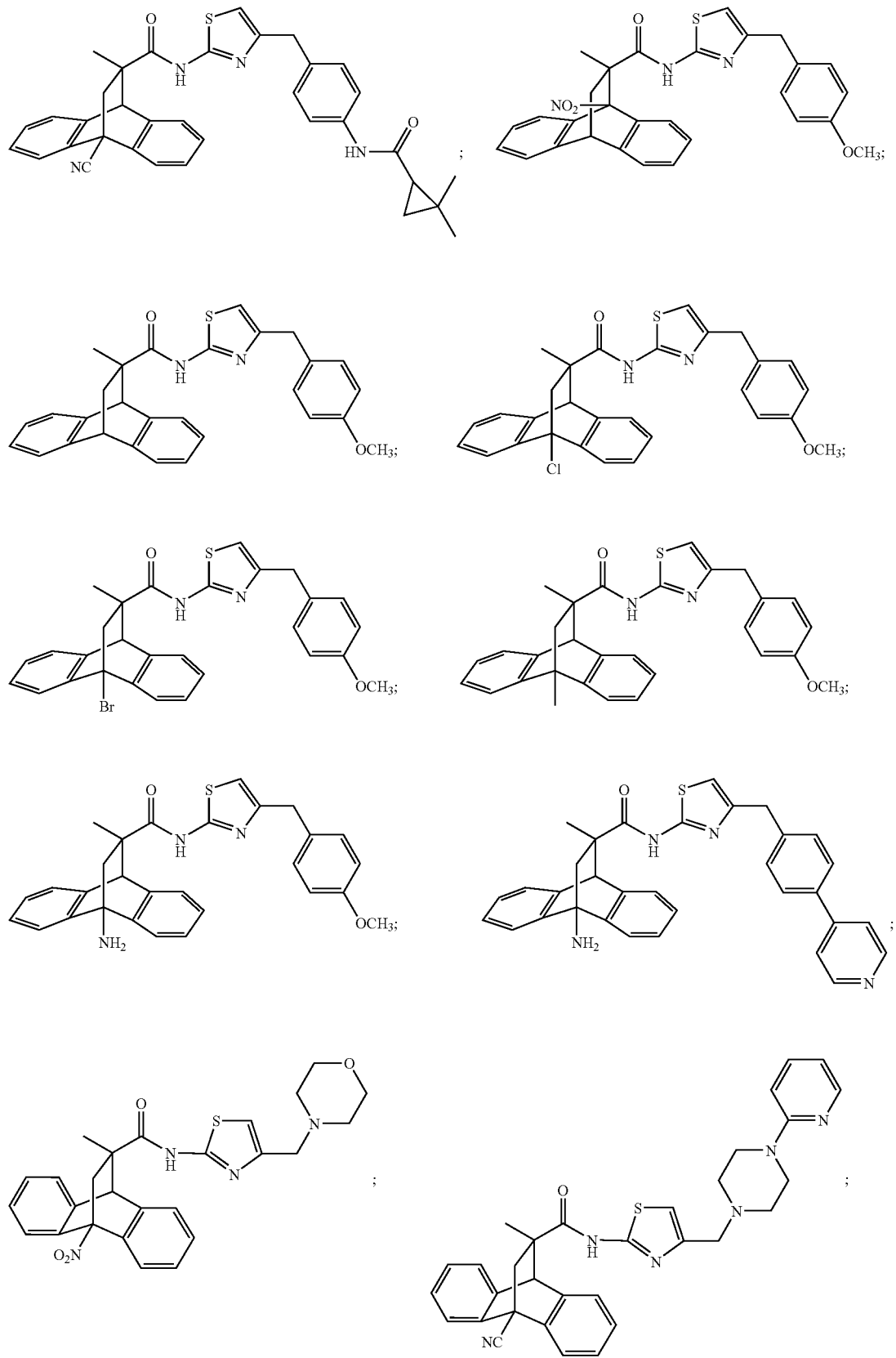

-continued
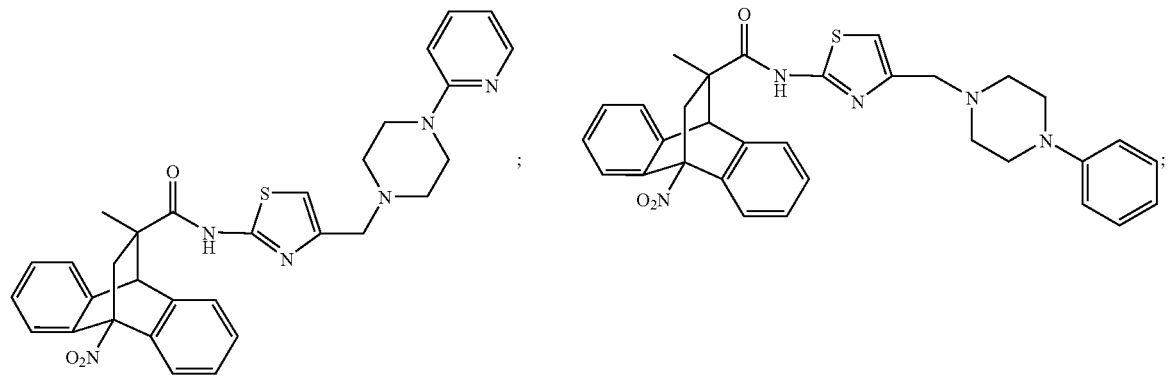
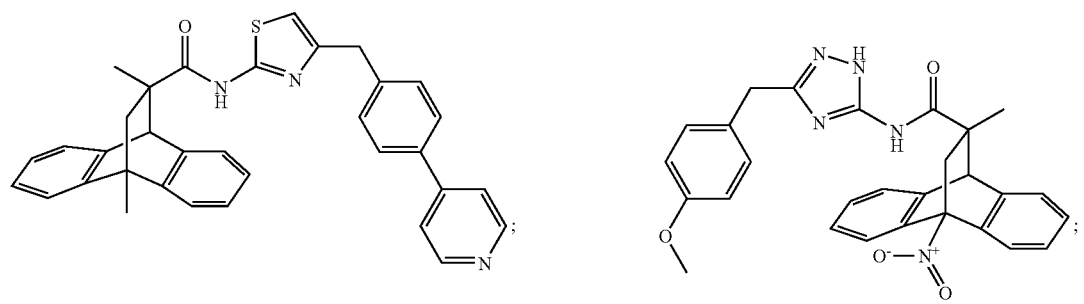
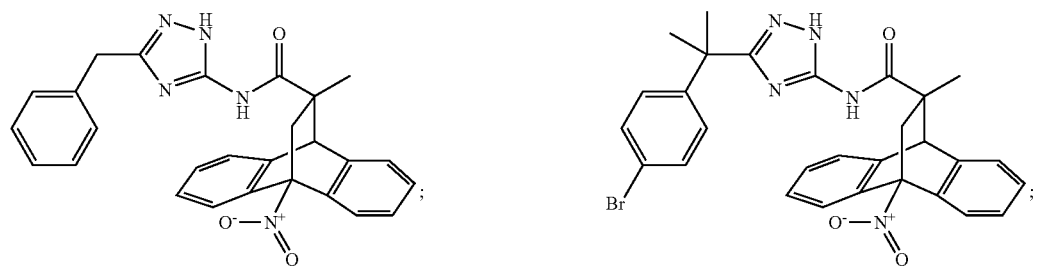
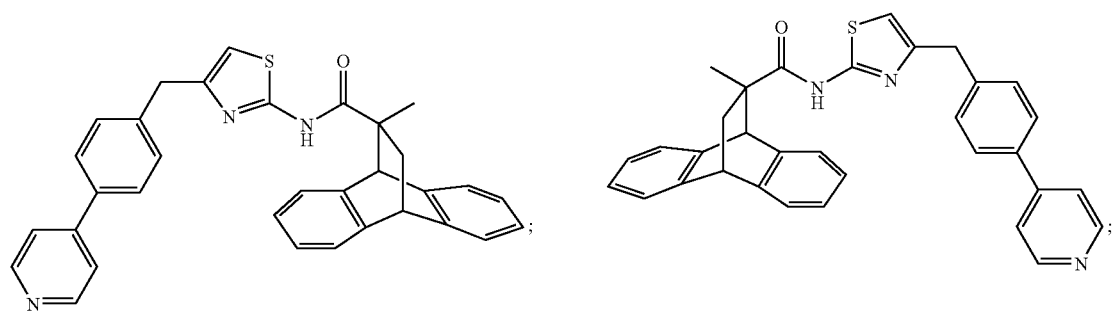

-continued
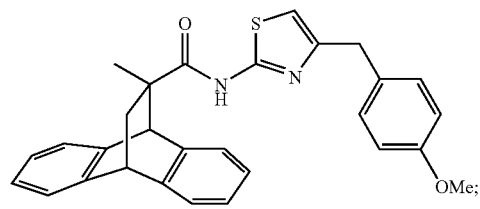 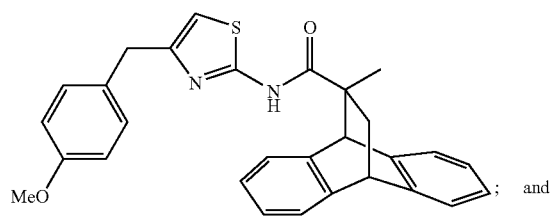; and
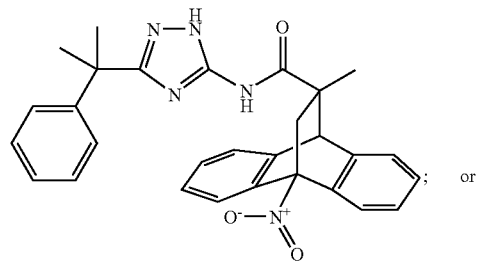; or
(ii) a stereoisomer, tautomer, or a pharmaceutically acceptable salt of (i) thereof.
14. A pharmaceutical composition comprising a compound as defined in claim 1 and a pharmaceutically acceptable carrier therefor.
\* \* \* \* \*